(12) United States Patent  (10) Patent No.: US 7,666,613 B2
Sonderegger  (45) Date of Patent: Feb. 23, 2010

(54) METHOD FOR IDENTIFYING COMPOUNDS TO TREAT SCHIZOPHRENIA USING NEUROTRYPSIN

(75) Inventor: Peter Sonderegger, Zurich (CH)

(73) Assignee: Universitat Zürich, Zürich (CH)

( * ) Notice: Subject to any disclaimer, the term of this patent is extended or adjusted under 35 U.S.C. 154(b) by 0 days.

(21) Appl. No.: 10/843,299

(22) Filed: May 12, 2004

(65) Prior Publication Data

US 2005/0032694 A1 Feb. 10, 2005

(51) Int. Cl.
  *G01N 33/53* (2006.01)
  *G01N 33/566* (2006.01)
  *G01N 33/567* (2006.01)
  *C12P 21/06* (2006.01)

(52) U.S. Cl. .................... 435/7.9; 435/7.1; 435/7.92; 435/69.1; 436/501; 436/503

(58) Field of Classification Search .................. None
See application file for complete search history.

(56) References Cited

U.S. PATENT DOCUMENTS

2002/0160490 A1* 10/2002 Tsuruoka et al. ............ 435/226
2004/0197825 A1* 10/2004 Karicheti et al. ............. 435/7.1
2004/0253606 A1* 12/2004 Aziz et al. ...................... 435/6

OTHER PUBLICATIONS

Proba et al., Biochem et Biophys Acta, 1998, 1396, pp. 143-147.*
Molinari et al., Science, 2002, 298, pp. 1779-1781.*
Poorafshar et al., Eur. J. Biochem., 1999, 261, pp. 244-250.*

* cited by examiner

*Primary Examiner*—Olga N Chernyshev
(74) *Attorney, Agent, or Firm*—Marshall, Gerstein & Borun LLP

(57) ABSTRACT

The present invention relates to neurotrypsin and to pharmaceutical and diagnostic compositions which comprise neurotrypsins and to compositions which effect neurotrypsin levels.

5 Claims, 33 Drawing Sheets

A

B

A

B

C

Abbreviations:

| | |
|---|---|
| H | Brain homogenate |
| S1 | Homogenate supernatant free of nuclear pellet |
| P2' | Crude synaptosomes |
| LP1 | Crude synaptic plasma membranes |
| LP2 | Crude synaptic vesicles |
| SV | Synaptic vesicles, purified with sucrose gradient |
| SPM | synaptic plasma membranes, purified with sucrose step gradient |
| Nt control | P2' of neurotrypsin(Ser711Ala)-overexpressing mouse |

A a  b

B a  b

METHOD FOR IDENTIFYING COMPOUNDS TO TREAT SCHIZOPHRENIA USING NEUROTRYPSIN

TECHNICAL FIELD

The present invention is directed to neurotrypsins and to a pharmaceutical composition which contains these substances or has an influence on these substances.

Schizophrenia: A Major Psychiatric Disease

Schizophrenia is a chronic, severe, and disabling brain disease. Approximately one percent of the world population develops schizophrenia during their lifetime. Individuals who develop schizophrenia experience severe suffering. Approximately 10% commit suicide. Although schizophrenia affects men and women with equal frequency, the disorder often appears earlier in men, usually in the late teens or early twenties, than in women, who are generally affected in the twenties to early thirties. People with schizophrenia often suffer terrifying symptoms such as hearing internal voices not heard by others, or believing that other people are reading their minds, controlling their thoughts, or plotting to harm them. These symptoms may leave them fearful and withdrawn. Their speech and behavior can be so disorganized that they may be incomprehensible or frightening to others. Available treatments can relieve many symptoms, but most people with schizophrenia continue to suffer some symptoms throughout their lives; it has been estimated that no more than one in five individuals recovers completely.

According to estimates provided by the National Institutes of Health of the USA, 3 million people suffer from schizophrenia in a given year alone in the US and the economic costs sum up to over 30 billion dollars. This ranks schizophrenia among the major disorders of the brain and the nervous system and of all human diseases.

| Condition | Total Cases | Costs Per Year |
| --- | --- | --- |
| Hearing Loss | 28 million | $56 billion |
| All Depressive Disorders | 18.8 million | $44 billion |
| Alzheimer's Disease | 4 million | $100 billion |
| Stroke | 4 million | $30 billion |
| Schizophrenia | 3 million | $32.5 billion |
| Parkinson's Disease | 1.5 million | $15 billion |
| Traumatic Head Injury | 1 million | $48.3 billion |
| Multiple Sclerosis | 350,000 | $7 billion |
| Spinal Cord Injury | 250,000 | $10 billion |

No single sign or symptom allows diagnosing schizophrenia. The crucial contributions to the definition of schizophrenia as a distinct illness of the mind were made by Eugen Bleuler (Bleuler, 1911) and Emil Kraepelin (Kraepelin et al., 1919) at the beginning of the past century. These two clinical psychiatrists are considered as the "founding fathers" of schizophrenia. Both recognized that the psychotic symptoms, such as delusions and hallucinations, are not specific to schizophrenia, but occur in many other illnesses, such as affective disorders (major depression and manic-depressive illness) or dementias. Both Kraepelin and Bleuler recognized that the hallmark of schizophrenia is the impairment in the ability to think in a clear, fluent, and logical way. Bleuler coined the name "schizophrenia" for this disturbance, because a "fragmenting of the mind" occurred to him as the fundamental abnormality. In this state, persons with schizophrenia had lost the capacity to link their thought process correctly together so that they were coherent with concepts. He wrote: "of thousands of associative threads that guide out thinking, this disease seems to interrupt quite haphazardly, sometimes single threads, sometimes a whole group, and sometimes whole segments of them".

Current Treatments of Schizophrenia are Insufficient

Current treatment of schizophrenia uses so-called antipsychotic drugs. These medications cannot "cure" the illness, but they can take away many of the symptoms or make them milder. In some cases, they can shorten the course of an episode of the illness as well. There are a number of antipsychotic (neuroleptic) drugs available. These medications affect neurotransmitters that allow communication between nerve cells, e.g. dopamine. The first antipsychotic medications were introduced in the 1950s. Antipsychotic medications have helped many patients with psychosis lead a more normal and fulfilling life by alleviating such symptoms as hallucinations, both visual and auditory, and paranoid thoughts. However, the early antipsychotic medications often have unpleasant side effects, such as muscle stiffness, tremor, and abnormal movements, leading researchers to continue their search for better drugs.

The 1990s saw the development of several new drugs for schizophrenia, called "atypical antipsychotics." Because they have fewer side effects than the older drugs, today they are often used as a first-line treatment. The first atypical antipsychotic, clozapine (Clozaril), was introduced in the United States in 1990. In clinical trials, this medication was found to be more effective than conventional or "typical" antipsychotic medications in individuals with treatment-resistant schizophrenia (schizophrenia that has not responded to other drugs), and the risk of tardive dyskinesia (a movement disorder) was lower. However, because of the potential side effect of a serious blood disorder—agranulocytosis (loss of the white blood cells that fight infection)—patients who are on clozapine must have a blood test every 1 or 2 weeks. The inconvenience and cost of blood tests and the medication itself have made maintenance on clozapine difficult for many people. Clozapine, however, continues to be the drug of choice for treatment-resistant schizophrenia patients. Several other atypical antipsychotics have been developed since clozapine was introduced. The first was risperidone (Risperdal), followed by olanzapine (Zyprexa), quetiapine (Seroquel), and ziprasidone (Geodon). Each has a unique side effect profile, but in general, these medications are better tolerated than the earlier drugs. Currently, all these medications have their place in the treatment of schizophrenia, depending on the patient's symptoms, age, weight, and personal and family medication history.

Antipsychotic medications are often accompanied by side effects, such as drowsiness, rapid heartbeat, and dizziness when changing position. Some patients gain weight while taking medications, while others suffer from a decrease in sexual ability or interest, problems with menstrual periods, sunburn, or skin rashes. Long-term treatment of schizophrenia with one of the older, or "conventional," antipsychotics may cause a person to develop tardive dyskinesia (TD). Tardive dyskinesia is a condition characterized by involuntary movements, most often around the mouth. It may range from mild to severe. In some people, it cannot be reversed, while others recover partially or completely. The risk of developing tardive dyskinesia has been reduced with the newer "atypical" medications.

The currently available treatments of schizophrenia reduce suffering considerably, but approximately ⅔ of the people affected by schizophrenia require public assistance within a few years after onset. The majority of them are unable to return to work or school and have relatively little or no social interactions. Therefore schizophrenia is one of the most important public health problems world-wide, and the costs to society are counted in billions of dollars. Schizophrenia is a brain disease that manifests itself in the activities of the mind. It impairs functions that are considered as specifically human, such as the ability to think creatively and imaginatively, the ability to have social relationships with other human beings, the ability to use language for the expression of ideas with clarity and to express emotions. People affected from schizophrenia are confronted with and scared of intrusive experiences such as hearing voices or the believe of being persecuted by individuals of their environment or by alien external forces.

Pathogenetic Mechanisms of Schizophrenia

Schizophrenia is Caused by Multiple Convergent Factors

Schizophrenia has no single cause nor has a single pathology been identified to underlie schizophrenia. A recent working model composed by Andreasen (Andreasen, 2000) nicely demonstrates the multiple components on different levels ranging from multiple etiological factors via multiple pathophysiological disturbances through disturbed anatomical and functional circuitries in the brain to the impaired functional cognitive processes in the affected brain (FIG. 1).

According to the currently accepted views, schizophrenia has a multifactorial etiology including an accumulation of genetic and non-genetic influences ranging from particular genes providing susceptibility to schizophrenia, exposure to toxins (e.g. radiation, amphetamines), viruses, and other pathogens, injuries to the brain occurring around birth, or later effects derived from particular nutritional components, and psychological experiences that produce somatic effects, such as excessive or particular forms of stress. An often proposed view is the possibility that the phenotype of schizophrenia is produced by the influence of multiple factors that lead to a common final pathophysiological pathway in the brain, that in turn results in a schizophrenic phenotype.

As heterogeneous and multifactorial as the etiologies are the proposed models for the pathology and pathophysiology underlying schizophrenia. However, and very importantly, schizophrenia differs from the classical dementias in the absence of visible neuropathological markers such as plaques, tangles, Lewy bodies or other clearly identifiable pathologies. Very importantly, gliosis, which is considered as a marker of neuronal death in neurodegenerative diseases, has never been found in the brains of individuals affected with schizophrenia.

Reduction in Synapse Number in the Interneuronal Neuropil is the Most Prominent Feature of Cortical Pathology in Schizophrenia The currently most consistent neuropathological finding in brains of schizophrenic patients is a reduction of the number of synapses in the gray matter of the central nervous system, which is reflected by a decrease in the volume of the neuropil (the synaptic area). No evidence for neuronal degeneration is observed. Typically, the number of neurons counted per area of tissue is rather increased, an observation explained by a selective decrease in the number of synapses in the neuropil area between the neurons while the number of neuronal cell somas remained constant. The phenomenon has been reported over the past two decades by several independent studies on post mortem material and has been found most extensive in the prefrontal cortex (Selemon et al., 1998). The literature documenting this observation has been carefully reviewed by Selemon and Goldman-Rakic (Selemon and Goldman-Rakic, 1999). Based on these observations, Selemon and Goldman-Rakic formulated the "Reduced Neuropil Hypothesis" as a circuit-based model of schizophrenia (FIG. 2). In brief, the "Reduced Neuropil Hypothesis" postulates that a reduction of the interneuronal neuropil in the prefrontal cortex has a devastating impact on cortical function by its compromising effects on the cortical circuitry.

The combined occurrence of a reduced total number of synapses, a reduction of the neuropil in conjunction with a constant or increased neuronal cell number was concluded to result from a reduced number of synapses per neuron. Later experimental studies on single neurons fully confirmed this conclusion by the direct observation of a reduced number of synaptic spines on dendrites of prefrontal cortical pyramidal neurons in the post-mortem brains of schizophrenic subjects (Garey et al., 1998; Glantz and Lewis, 2000). An illustration of the decreased dendritic spine density on prefrontal cortical pyramidal neurons in schizophrenia is given in FIG. 3.

Synaptic Pruning: A Normal Developmental Phenomenon With a Peak Activity During Adolescence In the context of these observations found on post mortem brains of schizophrenic subjects, the period of naturally occurring synapse reduction (synapse elimination or synapse pruning) during the adolescence age becomes highly interesting, as the onset of schizophrenia has one major peak during this stage of life. The physiological synapse elimination in the prefrontal cortex, resulting in a marked decline in synaptic density in layer 3 of the frontal cortex during late childhood, has first been described by Huttenlochner (1979). He found that the synaptic density (number of synapses per volume of brain) reaches the highest level at the age of 2-3 years. Then, a steep decline occurs in late childhood and early adolescence. At the age of approximately 20 years, the adult level of synaptic density is established. A further decline occurs only at extreme old age (FIG. 4).

Excessive Synaptic Pruning as a Cause for Schizophrenia (The Feinberg Hypothesis)

In 1982, Feinberg reviewed several lines of evidence suggesting that substantial changes in human brain function occur during adolescence and proposed that a defect in programmed synaptic elimination may result in schizophrenia. Huttenlochner's observation of large scale synapse elimination in puberty was subsequently confirmed in extensive electron microscopic studies on monkeys, and it was shown that the curves of synapse densities were very similar in monkeys and men, if normalized with regard to conceptional age (Zezevic et al., 1989; Bourgeois and Rakic, 1993; Rakic et al., 1994). More recently, in a study with non-human primates, a significant reduction of dendritic spines on layer 3 pyramidal neurons in the prefrontal cortex was found during adolescence in a pattern quite similar to that reported for synapse numbers (Anderson et al., 1993).

The Feinberg hypothesis of excessive synaptic pruning in the prefrontal cortex as a cause for schizophrenia, was carefully evaluated by Keshavan and colleagues (Keshavan et al., 1994) in the light of new neuro-anatomical data, studies of brain metabolism, electrophysiological abnormalities, gender differences in the onset and the severity of schizophrenia. This careful reconsideration provided an interesting overview on the then available observations with regard to various phenomenological aspects and circumstances of schizophrenia. They came to the conclusion that the research in the 1980ies support the maturational changes in the brain that occur in adolescence that have been taken as the basis for the Feinberg hypothesis. In addition, they concluded that a variety of neurobiological findings in schizophrenia suggest an exaggeration of the changes that are normally seen during development, and provide support to Feinberg's predictions (FIG. 5).

A decade later, McGlashan and Hoffman (2000) summarized the essential morphological, developmental, electrophysiological, and metabolic observations in schizophrenia again in the light of the "excessive synaptic pruning" hypothesis and came to the conclusion that "excessive synaptic pruning" or "developmentally reduced synaptic connectivity" (DRSC) is an increasingly attractive pathophysiological model of schizophrenia. In the new formulation the DRSC model posits that schizophrenia arises from critically reduced synaptic connectedness as a result of developmental disturbances of synaptogenesis during gestation and early childhood and/or excessive synaptic pruning during adolescence. The model accounts for the phenomenology of the disorder, the symptomatic states, the onset, neurodevelopmental deficits, window of deterioration, sex differences in clinical presentation, course determined by age of onset, and preservation of the schizophrenic genotype in the population despite diminished phenotypic fecundity.

Computer Simulation Predicts Excessive Synapse Elimination as a Mechanism for the Generation of Hallucinated Voices The disastrous impact of excessive synaptic pruning on the functional competence of the cortical circuitry was tested by computer simulation of a speech perception neural network (Hoffman and McGlashan, 1997; see also Hoffman and Dobscha, 1989). Connections within the working memory component of the network were eliminated on the basis of a "Darwinian rule" in order to model loss of synapses. As a comparison, neuronal cell death, also postulated as being linked to both neurodevelopment and schizophrenia, was simulated. The authors determined whether these alterations at low levels could enhance perceptual capacity and at high levels produce spontaneous speech percepts that simulate hallucinated speech or "voices." They found that eliminating up to 65% of working memory connections improved perceptual ability. Beyond that point, network performance declined and speech hallucinations emerged. Simulating neuronal loss at low levels also improved network performance, but in excess it did not produce hallucinations. In conclusion, the computer simulation model demonstrated perceptual advantages of selective synaptic elimination as well as selective neuronal loss. The model further predicts that psychosis arises from a pathological extension of one of these normal neurodevelopmental processes, namely, synaptic elimination.

Conclusion: Excessive Synaptic Pruning Causes Schizophrenia

According to the Feinberg hypothesis, schizophrenia results from excessive synaptic pruning during late childhood and adolescence. Synaptic pruning (FIG. 6, light gray line) is a normal developmental phenomenon during the maturation of the nervous system. Multiple factors and mechanisms are capable of promoting synaptic pruning. Excessive activity of one or several of these pruning-promoting factors results in excessive synaptic pruning. Excessive synaptic pruning leading to a synaptic density below a certain threshold results in anatomical and functional disruption of neuronal connectivity and communication. Functional disruption of neuronal connectivity results in impaired fundamental and secondary cognitive processes and thus to schizophrenia.

DESCRIPTION OF THE FIGURES

in FIG. 3A) of the CA1 region of the hippocampus of an adult mouse. Neurotrypsin was visualized using preembedding staining with a specific, affinity-purified antibody against the proteolytic domain of neurotrypsin and a peroxidase-conjugated secondary antibody. The neurotrypsin immunoreactivity is found at presynaptic sites of axospinous and axodendritic asymmetric synapses. The immunoperoxidase reaction product is associated with the presynaptic membrane and the active zone of the presynaptic terminal (arrows). (Pre, presynaptic axon terminal; Post, postsynaptic spine).

in FIG. 3A) of the CA1 region of the hippocampus of an adult mouse. The synaptic localization of neurotrypsin was confirmed. Neurotrypsin was visualized using specific, affinity-purified primary antibody against the protease domain and 1.4 nm gold-conjugated secondary antibody, followed by silver intensification. Neurotrypsin accumulates within the presynaptic active zones of the axonal terminals that form asymmetric (arrows) synapses with dendritic spines (sp, A and B) and dendritic shafts (dend, D and E), and symmetric (arrowheads) synapses with neuronal somata (C and F). Scale bar, 0.2 μm.

DETAILED DISCLOSURE

Figure 1:
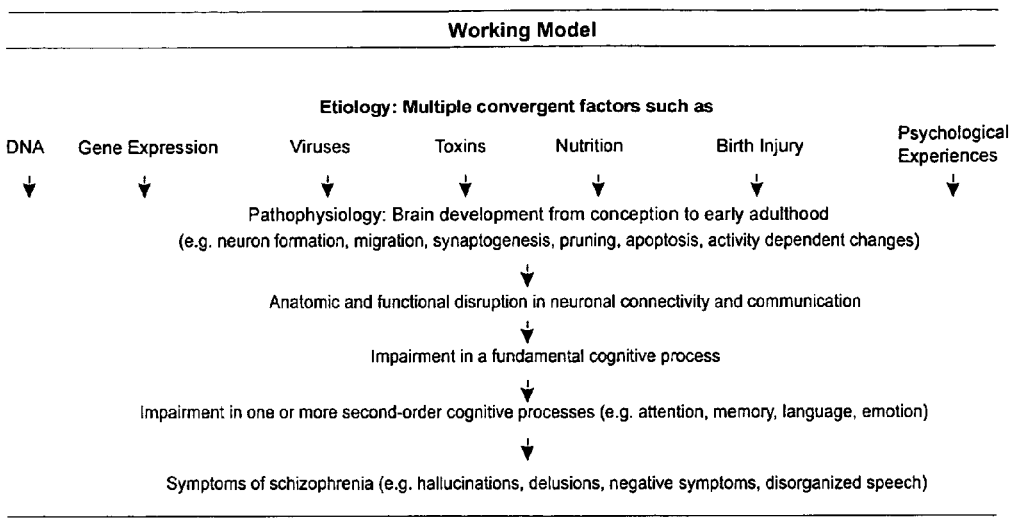
FIG. 1: Working model for the etiology and pathophysiology of schizophrenia according to Andreasen (2000). According to the currently prevalent view, the phenotype of schizophrenia is produced by the influence of multiple factors that lead to a common final pathophysiological pathway in the brain. Characteristic for this common final pathway is that it results in an abnormality in neural connectivity that occurs as the brain develops and modifies itself in response to a variety of internal and external influences. As a common psychopathological feature, individuals with schizophrenia exhibit an impairment in a fundamental cognitive process, which in turn results in impaired second order cognitive processes (e.g. attention, memory, language, emotion). Based on these disturbances, the symptoms of schizophrenia, e.g. hallucinations, delusions, negative symptoms, and disorganized speech appear.
Figure 2:
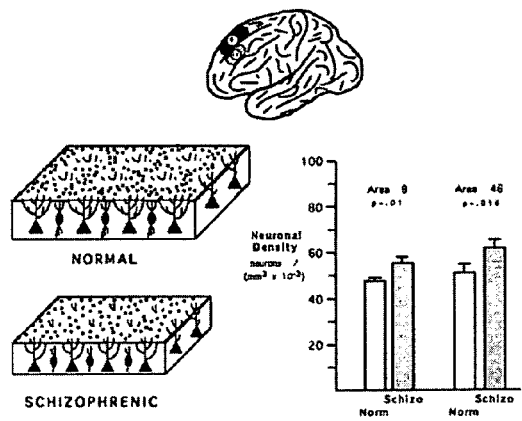
FIG. 2: The reduced neuropil hypothesis. Top center: The approximate locations of prefrontal areas 9 (magnocellular) and 46 are shown on a lateral view of the human brain. Lower right: Neuronal density is elevated in areas 9 and 46 by 17% and 21%, respectively (Selemon et. al., 1998). Lower left: This schematic diagram illustrates the "reduced neuropil hypothesis," i.e., the schizophrenic cortex contains the same number of neurons as the normal cortex; reduced cortical volume is due to a decrease in interneuronal neuropil, dendritic trees, and cortical afferents (stippling on top of boxes).
Figure 3:
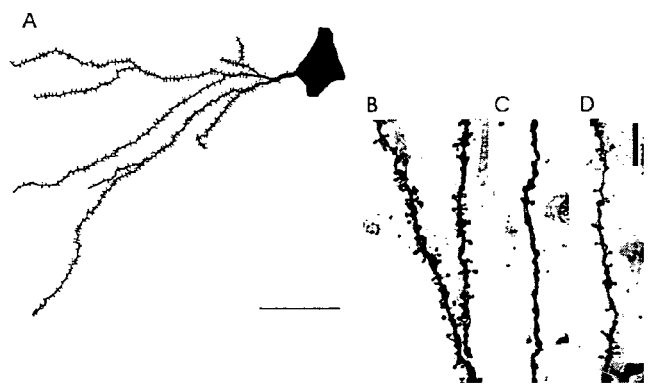
FIG. 3: Decreased dendritic spine density on prefrontal cortical pyramidal neurons in schizophrenia (from Glantz and Lewis, 2000). The density of spines on basilar dendrites of Golgi-impregnated neurons is shown on a pyramidal neuron of layer 3 of the dorsolateral prefrontal cortex (area 46) of a normal (B) and two schizophrenic (C and D) subjects. Panel A shows a reconstruction of the basilar dendrites of a layer 3 pyramidal neuron in a control subject for the orientation of the reader.
Figure 4:
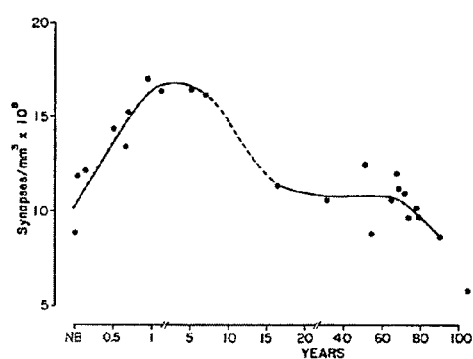
FIG. 4: Physiological synaptic pruning. Synaptic density in layer 3 of the human mid-frontal gyrus is shown as a function of age (taken from Huttenlochner, 1979). Note that the synaptic density (number of synapses per volume of brain) reaches the highest level at the age of 2-3 years. Then, a steep decline occurs in late childhood and early adolescence. At the age of approximately 20 years, the adult level of synaptic density is established. A further decline occurs only at extreme old age.
Figure 5:
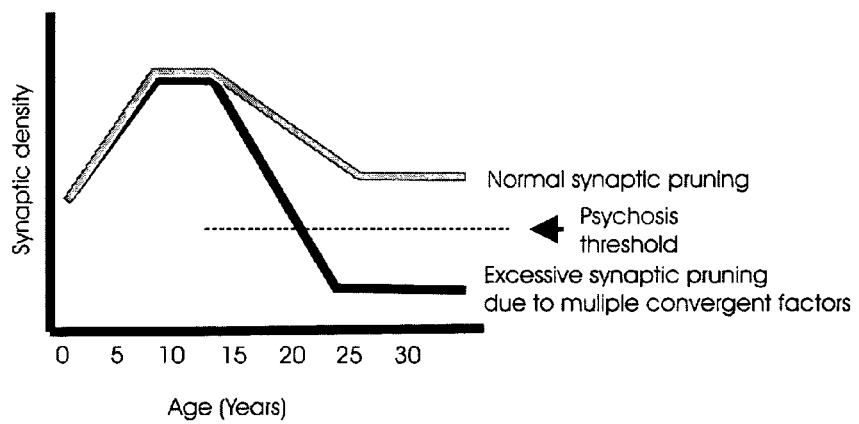
FIG. 5: The "excessive synaptic pruning" hypothesis of schizophrenia. The diagrammatic representation of the synaptic density (light gray line) in healthy humans increases after birth to a maximum at ages 2-3 years. Then, it declines steeply in late childhood and early adolescence and reaches the constant adult level between ages 20-25 years. According to the hypothesis promoted by Feinberg (1982), schizophrenia develops if synaptic pruning during late childhood and adolescence is excessive (black line).

Neurotrypsin is a newly discovered serine protease, which is predominantly expressed in the brain and in the lungs; the expression in the brain takes place nearly exclusively in the neurons.

Neurotrypsin has a previously not yet found domain composition: besides the protease domain, there are found 3 or 4 SRCR (scavenger receptor cysteine-rich) domains and one Kringle domain. It is to be pointed out that the combination of Kringle and SRCR domains has not yet been found in proteins. At the amino terminus of the neurotrypsin protein there is a segment of more than 60 amino acids, which has an extremely high proportion of proline and basic amino acids (arginine and histidine).

The invention is characterized by the characteristics in the independent claims. Preferred embodiments are defined in the dependent claims.

The newly found neurotrypsins neurotrypsin of the human (compound of the formula I), neurotrypsin of the mouse (compound of the formula II) differ structurally very much from the so far known serine proteases.

The serine protease whose protease domain is structurally most closely related with the protease domain of the new compounds, namely plasmin (of the human), has only a 44% amino acid sequence identity.

The proline-rich, basic segment at the amino terminus has a certain resemblance with the basic segments of the netrins and the semaphorins/collapsins. Due to this segment, it is probable that neurotrypsin may be enriched by means of heparin-affinity chromatography.

The neurotrypsins of the human (compound of the formula I) and of the mouse (compound of the formula II) exhibit a very high structural similarity among each other.

The identity of the amino acid sequences of the native proteins of the compounds of the formulas I or II amounts to 81%.

The neurotrypsin of the human (compound of the formula I) has a coding sequence of 2625 nucleotides. The coded peptide of the compound of the formula I has a length of 875 amino acids and contains a signal peptide of 20 amino acids. The neurotrypsin of the mouse (compound of the formula II) has a coding sequence of 2283 nucleotides. The coded protein of the compound of the formula II has a length of 761 amino acids and contains a signal peptide of 21 amino acids. The reason for the greater length of the neurotrypsin of the human consists therein that the human neurotrypsin has 4 SRCR domains, whereas the neurotrypsin of the mouse has only 3 SRCR domains.

The domains which are present in both compounds (compound of the formula I and compound of the formula II) have a high degree of sequence similarity. The corresponding SRCR domains of the compounds of the formulas I and II have an amino acid sequence identity from 81% to 91%. The corresponding Kringle domains have an amino acid sequence identity of 75%. A high degree of similarity consists also in the enzymatically active (i.e. proteolytic) domain (90% amino acid sequence identity).

The protease domains of the neurotrypsins of the human (compound of the formula I; SEQ ID NO: 5) and of the mouse (compound of the formula II; SEQ ID NO: 6) are aligned in the following section, in order to illustrate the high degree of sequence identity.

```
CGLRLLHRRQKRIIGGKNsLRGGwPwQvsLRLKSSHGDGRLLcGATLLss    50
|||||||||||||||.||||:||||.||||:|.||||||||||||||
CGLRLLHRRQKRIIGGNNSLRGAWPWQASLRLRSAHGDGRLLCGATLLSS
CWVLTAAHCFKRYGNSTRSYAVRVGDYHTLVPEEFEEEIGVQQIVIHREY    100
||||||||||||||..|||||||||||||:||||||||||||||:|
CWVLTAAHCFKRYGNNSRSYAVRVGDYHTLVPEEFEQEIGVQQIVIHRNY
RPDRSDYDIALVRLQGPEEQCARFSSHVLPACLPLWRERPQKTASNCYIT    150
||||||||||||||:||||:|.||||||||||||||||||||||.||
RPCRSDYDIALVRLQGPGEQCARLSTHVLPACLPLWRERPQKTASNCHIT
GWGDTGRAYSRTLQQAAIPLLPKRFCEERYKGRFTGRMLCAGNLHEHKRV    200
||||||||||||||||:|||||||||.||||||||||||||||:|..||
GWGDTGRAYSRTLQQAAVPLLPKRFCKERYKGLFTGRMLCAGNLQEDNRV
DSCQGDSGGPLMCERPGESWVVYGVTSWGYGCGVKDSPGVYTKVSAFVPW    250
||||||||||||||:|||||||||||||||||||||.|||||:|.||||
DSCQGDSGGPLMCEKPDESWVVYGVTSWGYGCGVKDTPGVYTRVPAFVPW
IKSVTKL    258
|||||.|
IKSVTSL
```

From the 258 amino acid sequence positions included in the comparison there are 233 amino acids that are identical in both compounds (upper sequence: compound of the formula I; lower sequence: compound of the formula II; identical amino acids are indicated by vertical lines).

The inventive neurotrypsins are unique when compared with the known serine proteases in that they are expressed according to currently available observations in a distinct degree in neurons. A further organ with a strong expression of neurotrypsin is the lungs (see Gschwend et al., *Mol. Cell. Neurosci.* 9:207-219, 1997).

The proteins that are structurally most similar to the compounds of the formulas I or II are serine proteases, such as tissue-type plasminogen activator (tPA), urokinase type plasminogen activator (U PA), plasmin, trypsin, apolipoprotein (a), coagulation factor XI, neuropsin, and acrosin.

In the adult brain, the inventive compounds are expressed predominantly in the cerebral cortex, the hippocampus, and the amygdala. In the adult brain stem and the spinal cord, the inventive compounds are expressed predominantly in the motor neurons. A slightly weaker expression is found in the neurons of the superficial layers of the dorsal horn of the spinal cord. In the adult peripheral nervous system, the inventive compounds are expressed in a subpopulation of the sensory ganglia neurons.

The inventive compounds were found in connection with a study aimed at discovering trypsin-like serine proteases in the nervous system. The first compound that was found and characterized was the compound of the formula II (Gschwend et al., *Mol. Cell. Neurosci.* 9:207-219, 1997). By means of an alignment of the protease domains of 7 known serine proteases (tissue-type plasminogen activator, urokinase-type plasminogen activator, thrombin, plasmin, trypsin, chymotrypsin, and pancreatic elastase) in the proximity of the histidine and the serine of the catalytic triad of the active site, the sequences of the so-called primer oligonucleotides for the polymerase chain reaction were determined.

The primer oligonucleotides were used in a polymerase chain reaction (PCR) together with ss-cDNA from total RNA of the brains of 10 days old mice and resulted in the amplification of a cDNA fragment of a length of approximately 500 base pairs. This cDNA fragment was used successfully for the isolation of further cDNA fragments by screening commercially available cDNA libraries. Together, the isolated cDNA fragments covered the full length of the coding part of the compound of the formula II. By conventional DNA sequencing the complete nucleotide sequence and the amino acid sequence deduced therefrom was obtained.

The compound of the formula I was cloned based on its pronounced similarity with the compound of the formula II. The primer oligonucleotides used were synthesized according to the known sequence of the compound of the formula II.

The cloning of the compound of the formula I was performed by means of two commercially available cDNA libraries from fetal human brain. This procedure for the cloning can also be used for the isolation of the homologous compounds of other species, such as rat, rabbit, guinea pig, cow, sheep, pig, primates, birds, zebra fish (*Brachydanio rerio*), *Drosophila melanogaster*, *Caenorhabditis elegans*, etc.

The coding nucleotide sequences can be used for the production of proteins with the coded amino acid sequences of the compounds of the formulas I or II. A procedure developed in our laboratory allows the production of recombinant proteins in myeloma cells as fusion proteins with an immunoglobulin domain (constant domain of the kappa light chain). The principle of the construction is given in detail by Rader et al. (Rader et al., *Eur. J. Biochem.* 215:133-141, 1993). The fusion protein produced by the myeloma cells was isolated by immunoaffinity chromatography using a monoclonal antibody against the Ig domain of the kappa light chain. With the same expression method, also the native protein of a compound, starting from the coding sequence, can be produced.

The coding sequences of the compounds of the formulas I or II can be used as starting compounds for the discovery and the isolation of alleles of the compounds of the formulas I or II. Both the polymerase chain reaction and the nucleic acid hybridization can be used for this purpose.

The coding sequences of the compounds of the formulas I or II can be used as starting compounds for so-called "site-directed mutagenesis", in order to generate nucleotide sequences coding the coded proteins that are defined by the compounds of the formulas I or II, or parts thereof, but whose nucleotide sequence is degenerated with respect to the compounds of the formulas I or II due to use of alternative codons.

The coding sequences of the compounds of the formulas I or II can be used as starting compounds for the production of sequence variants by means of so-called site-directed mutagenesis.

INDUSTRIAL APPLICABILITY

The coding sequences of the formulas I and II can be used for the production of the coded proteins or parts thereof of the formulas I and II. The production of the coded proteins can be achieved in prokaryotic or eukaryotic expression systems.

The role of neurotrypsin as a regulator of synaptic structure and function is extensively documented in the Examples below. Therefore, neurotrypsin is a target for the development of drugs aimed at modulating synaptic function. Neurotrypsin is indispensable for normal cognitive function of the human brain. Complete inactivity of neurotrypsin in human subjects, due to a truncating deletion in the PRSS12 gene encoding neurotrypsin, causes severe mental retardation. In contrast, excessive levels of neurotrypsin at the synapse cause enhanced long-term potentiation and enhanced neuronal excitability. Therefore, both pharmaceutical drugs that enhance the activity of neurotrypsin and pharmaceutical drugs that reduce the activity of neurotrypsin may be of practical use as regulators of synaptic homeostasis and may counteract cognitive deficits caused by an imbalance of synaptic plasticity.

Many of the currently used pharmaceuticals for the treatment of major psychiatric diseases, such as depression and schizophrenia, are agents that modulate synaptic function. Pharmaceuticals that enhance or reduce the function of neurotrypsin are expected to act in part on the same synaptic functions as drugs commonly used for the treatment of major psychiatric diseases.

The gene expression pattern of the inventive compounds in the brain is extremely interesting, because these molecules are expressed in the adult nervous system predominantly in neurons of those regions that are thought to play an important role in learning and memory functions. Together with the recently found evidence for a role of extracellular proteases in neural plasticity, the expression pattern allows the assumption that the proteolytic activity of neurotrypsin has a role in structural reorganizations in connection with learning and memory operations, for example operations which are involved in the processing and storage of learned behaviors, learned emotions, or memory contents. The inventive compounds may, thus, represent a target for pharmaceutical intervention in malfunctions of the brain.

The gene expression pattern of the inventive compounds in the cerebral cortex (especially layers V and VI) is extremely interesting, because a reduction of the cellular differentiation in the cerebral cortex has been found to be associated with schizophrenia. The inventive compounds may, thus, be a target for pharmaceutical intervention in schizophrenia and related psychiatric diseases.

The coding sequences of the inventive compounds have been found to be increased in the neurons located adjacent to the damaged tissue of a focal ischemic stroke, indicating that the inventive compounds play a role in the tissue reaction in the injured cerebral tissue. The inventive compounds may, thus, represent a target for pharmaceutical intervention after ischemic stroke and other forms of neural tissue damage.

Tissue-type plasminogen activator, a serine protease related to the inventive compounds, has recently been found to be involved in excitotoxicity-mediated neuronal cell death. A similar function is conceivable for the inventive compounds and, thus, the inventive compounds represent a possible target for a pharmacological intervention in diseases in which cell death occurs.

The gene expression pattern of the inventive compounds in the spinal cord and in the sensory ganglia is interesting, because these molecules are expressed in the adult nervous system in neurons of those brain regions that are thought to play a role in the processing of pain, as well as in the pathogenesis of pathological pain. The inventive compounds may, thus, be a target for pharmaceutical intervention in pathological pain.

EXAMPLES

Example 1

CDNA Cloning of the Compound of the Formula II (Neurotrypsin of the Mouse)

Total RNA was isolated from the brains of 10 days old mice (ICR-ZUR) according to the method of Chomczynski and Sacchi (1987). The production of single stranded cDNA was carried out using oligo(dT) primer and a RNA-dependent DNA polymerase (SuperScript RNase H-Reverse Transcriptase; Gibco BRL, Gaithersburg, Md.) according to the instruction of the supplier. For the realization of the polymerase chain reaction one forward primer was synthesized based on the amino acid sequence of the region of the conserved histidine of the catalytic triad and one primer in the backward direction was synthesized based on the amino acid sequence of the region of the conserved serine of the catalytic triad of the serine proteases. The amino acid sequences used for the determination of the oligonucleotide primers were taken from seven known serine proteases. They are presented in the following.

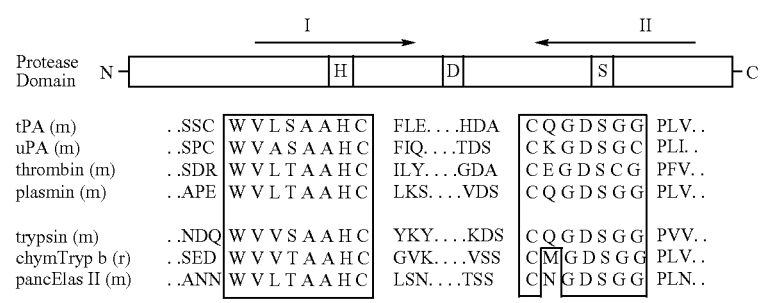

The protease domains of 7 known serine proteases (tissue-type plasminogen activator, urokinase-type plasminogen activator, thrombin, plasmin, trypsin, chymotrypsin, and pancreatic elastase) were aligned in the region of the conserved histidine and serine of the catalytic triad of the active site. The conserved amino acids of these regions were taken as the basis for the determination of the degenerated primers. The primer sequences are given according to the recommendation of the IUB nomenclature (Nomenclature Committee 1985).

The primers used in the PCR contained restriction sites for EcoRI and BamHI at their 5' ends in order to facilitate a subsequent cloning.

In the reading direction (sense primers):

(SEQ ID NO: 23)
5'-GGGGAATTCTGGGT|(C/G)(T/C)|(T/A)(G/C)|GC|GC|CA(T/C)TG-3'

In the counter direction (antisense primers):

(SEQ ID NO: 24)
5'-GGGGGATCCCC|CC|(G/C)(A'T)(A/G)TC|CC(C/T)T(G/Ctr)(G/A)CA-3'.

The polymerase chain reaction was carried out under standard conditions using the DNA polymerase AmpliTaq (Perkin Elmer) according to the recommendations of the producer. The following PCR profile was employed: 93° C. for 3 minutes, followed by 35 cycles of 93° C. for 1 minute, 48° C. for 2 minutes, and 72° C. for 2 minutes. Following the last cycle, the incubation was continued at 72° C. for further 10 minutes.

The amplified fragments had an approximate length of 500 base pairs. They were cut with EcoRI and BamHI and inserted in a Blue Script vector (Bluescript SK(−), Stratagene). The resulting clones were analyzed by DNA sequence determination using the dideoxy chain termination method (Sanger et al., *Proc. Natl. Acad. Sci. USA* 77:2163-2167, 1977) on an automated DNA sequencer (LI-COR, model 4000L; Lincoln, Nebr.) using a commercial sequencing kit (SequiTerm long-read cycle sequencing kit-LC; Epicentre Technologies, Madison, Wis.). The analysis yielded a sequence of 474 base pairs of the catalytic region of the serine protease domain of the compound of the formula II.

The 474 base pair long PCR fragment was used for screening of an oligo(dT)-primed Uni-ZAP-XR cDNA library from the brain of 20 days old mice (Stratagene; cat. no. 937319). At total of 3×106 lambda plaques were screened under high stringent conditions (Sambrook et al., *Molecular Cloning: A Laboratory Manual*, Cold Spring Harbor Laboratory Press, 1989) using a radioactively labeled PCR fragment as a probe and 24 positive clones were found.

From the positive Lambda-Uni-ZAP-XR phagemid clones the corresponding Bluescript plasmid was cut out by in vivo excision according to a standard method recommended by the producer (Stratagene). In order to determine the length of the inserted fragments the corresponding Bluescript plasmid clones were digested with SacI and KpnI. The clones containing the longest fragments were analyzed by DNA sequencing (as described above) and for subsequent data analysis the GCG software (version8.1, Unix; Silicon Graphics, Inc.) was used.

Because none of the clones contained the coding sequence in full length, a second cDNA library was screened. The library used in this screen was an oligo(dT)- and random-primed cDNA library in a Lambda phage (Lambdagut1 0) which was based on mRNA from 15 days old mouse embryos (oligo(dT)- and random-primed Lambda gtIO cDNA library; Clontech, Palo Alto, Calif.; cat. no. ML 3002a). As a probe a radioactively labeled DNA fragment (AvaI/AatII) from the 5' end of the longest clone of the first screen was used and approximately 2×106 plaques were screened. This screen resulted in 14 positive clones. The cDNA fragments were excised with EcoRI and cloned into the Bluescript vector (KS(+); Stratagene). The sequence analysis was carried out as described above.

In this way the nucleotide sequence over the full length cDNA of 2361 and 2376 base pairs, respectively, of the compound of the formula II was obtained. With the described procedure of PCR cloning it is possible to find and isolate also variant forms of the compounds of the formulas I or II, as for example their alleles or their splice variants. The described method of screening of a cDNA library allows also the detection and the isolation of compounds which hybridize under stringent conditions with the coding sequences of the compounds of the formulas I or II.

Example 2

Cloning of the cDNA of the Compound of the Formula I (Neurotrypsin of the Human)

The cloning of the cDNA of the compound of the formula I was carried out basing on the nucleotide sequence of the compound of the formula II. As a first step, a fragment of the compound of the formula I was amplified using the polymerase chain reaction (PCR). As a matrix we used the DNA obtained from a cDNA library from the brain of a human fetus(17'h-18I h week of pregnancy) which is commercially available (Oligo(dT) and random-primed, human fetal brain cDNA library in the Lambda ZAP II vector, cat. no. 936206, Stratagene). The synthetic PCR primers contained restriction sites for HindIII and XhoI at the 5' end in order to facilitate the subsequent cloning.

In the reading direction (sense primers):

(SEQ ID NO: 25)
5'-GGGAAGCTTGG|CA(A/G)TGGGG|AC|(A/G) T|TG (C/T) GA (C/T)-3'

In the counter direction (antisense primers):

(SEQ ID NO: 26)
5'-GGGCTCGAGCCCCA|CCTGTTATGTAA|AGTTG-3'.

The PCR was carried out under standard conditions using the DNA polymerase Amplitaq (Perkin Elmer) according to the recommendations of the producer. The resulting fragment of 1116 base pairs was inserted into the Bluescript vector (Bluescript SK(−), Stratagene). A 600 base pairs long HindIII/StuI fragment, corresponding to the 5' half the 1116 base pairs long PCR fragment, was used for the screening of a Lambda cDNA library from human fetal brain (Human Fetal Brain 5'-STRETCH PLUS cDNA library; Lambda gt10; cat. no. HL 3003 a; Clontech). 2×106 Lambda plaques were screened under high stringent conditions (Sambrook et al., Molecular Cloning: A laboratory manual, Cold Spring Harbor Laboratory Press, 1989) by means of a radioactively labeled PCR fragment, and 23 positive clones were found and isolated.

From the positive Lambda gt10 clones the corresponding cDNA fragments were excised with EcoRI and inserted into a Bluescript vector (Bluescript KS(+), Stratagene). The sequencing was carried out by means of the dideoxy chain termination method (Sanger et al., Proc. Natl. Acad. Sci. USA77 pages 2163-2167, 1977), using a commercial sequencing kit (SequiTherm long-read cycle sequencing kit-LC; Epicentre Technologies, Madison, Wis.) and Bluescript-specific primers.

In an alternative sequencing strategy, the cDNA fragments of the positive Lambda gt10 clones were PCR amplified using Lambda-specific primers. The sequencing was carried out as described above.

The computerized analysis of the sequences was performed by means of the program package GCG (version8.1, Unix; Silicon Graphics Inc.).

In this way the nucleotide sequence over the full length of the cDNA of 3350 base pairs was obtained. With the described procedure for PCR cloning it is possible to find and to isolate also variant forms of the compounds of the formulas I or II, as for example their alleles or their splice variants. The described procedure for the screening of a cDNA library allows also the discovery and the isolation of compounds which hybridize under stringent conditions with the coding sequences of the compounds of the formulas I or II.

Example 3

Visualization of the Coded Sequences of the Compounds of the Formulas I or II by Means of Antibodies The more than 60 amino acids long proline-rich, basic segment at the amino terminus of the coded sequence of the compounds of the formulas I or II is well suited for the production of antibodies by means of synthesizing peptides and using them for immunization. We have selected two peptide sequences with a length of 19 and 13 amino acids from the proline-rich, basic segment at the amino terminus of the coded sequence of the compound of the formula II for the generation of antibodies. The peptides had the following sequences:

Peptide 1: $H_2N$-SRS PLH RPH PSP PRS QX-$CONH_2$ (SEQ ID NO: 27)

Peptide 2: $H_2N$-LPS SRR PPR TPR F-COOH (SEQ ID NO: 28).

The two peptides were synthesized chemically, coupled to a macromolecular carrier (Keyhole Limpet Hemacyanin), and injected into 2 rabbits for immunization. The resulting antisera exhibit a high antibody titer and could successfully be used both for the identification of native neurotrypsin in brain extract of the mouse and for the identification of recombinant neurotrypsin. The employed procedure for the generation of antibodies can also be used for the generation of antibodies against the coded sequence of the compound of the formula I.

The resulting antibodies against the partial sequences of the coded sequences of the compounds of the formulas I or II can be used for the detection and the isolation of variant forms of the compounds of the formulas I or II, as for example alleles or splice variants. Such antibodies can also be used for the detection and isolation of gene technologically generated variants of the compounds of the formulas I or II.

Example 4

Purification of the Coded Sequences of the Compounds of the Formulas I or II

Besides conventional chromatographic methods, as for example ion exchange chromatography, the purification of the coded sequences of the compounds of the formulas I or II can also be achieved using two affinity chromatographic purification procedures. One affinity chromatographic purification procedure is based on the availability of antibodies. By coupling the antibodies on a chromatographic matrix, a purification procedure results, in which a very high degree of purity of the corresponding compound can be achieved in one step.

Another important feature that can be used for the purification of the coded sequences of the compounds of the formulas I or II is the proline-rich, basic segment at the amino terminus. It may be expected that, due to the high density of positive charges, this segment mediates the binding of the coded sequences of the compounds of the formulas I or II to heparin and heparin-like affinity matrices. This principle allows also the isolation, or at least the enrichment, of variant forms of the coded sequences of the compounds of the formulas I or II, as for example their alleles or splice variants. Likewise the heparin affinity chromatography can be used for the isolation, or at least the enrichment, of species-homologous proteins of the compounds of the formulas I or II.

Example 5

Neurotrypsin Messenger RNA is Expressed by Many Neuronal Subpopulations of the Central Nervous System (CNS) and the Peripheral Nervous System (PNS), (Results Revealed by In Situ Hybridization)

In order to determine the expression of neurotrypsin messenger RNA (mRNA) in the brain at cellular resolution, in situ hybridization was performed as described previously (Schaeren-Wiemers, N. and Gerfin-Moser, A., *Histochemistry* 100: 431-440, 1993). The synthesis of riboprobes was performed by in vitro transcription according to standard techniques. To generate sense and antisense riboprobes, full-length cDNA of mouse neurotrypsin (2.3 kb) in the phagemid vector pBluescript (Stratagene) was linearized with restriction enzymes cutting immediately downstream of the cDNA to be transcribed. Using T3 or T7 RNA polymerase and DIG RNA labeling kit (Boeringer), cRNA was synthesized according to the manufacturer's recommendations. cRNA from full length cDNA was subject to partial alkaline hydrolysis in 100 mM sodium carbonate pH 10.2 at 60° C. for 20-40 min to generate ~300 bp fragments. The riboprobes were then mixed with an equal volume of formamide and stored at −70° C. The size of riboprobes was examined by agarose gel electrophoresis. Riboprobes were used at a concentration of approximately 250 ng/ml.

For in situ hybridization, 20 µm cryostat sections were air dried, fixed in 4% paraformaldehyde (in phosphate-buffered saline, pH 7.4) and acetylated with acetic anhydride. After prehybridization in hybridization buffer containing 5×SSC, 50% formamide, 5× Denhardt's solution, 250 µg/ml total yeast RNA, and 500 µg/ml DNA from herring sperm, hybridization was performed at 53° C. overnight in hybridization buffer containing the riboprobe. The slides were then washed in graded concentrations of SSC with a high-stringency step of 0.2×SSC/50% formamide at 53° C. Immunological detection of digoxigenin-labeled hybrids was performed using alkaline phosphatase-conjugated anti-digoxigenin antibody and NBT/BCIP. The color reaction was developed in the dark for 12-24 h.

Figure 13:
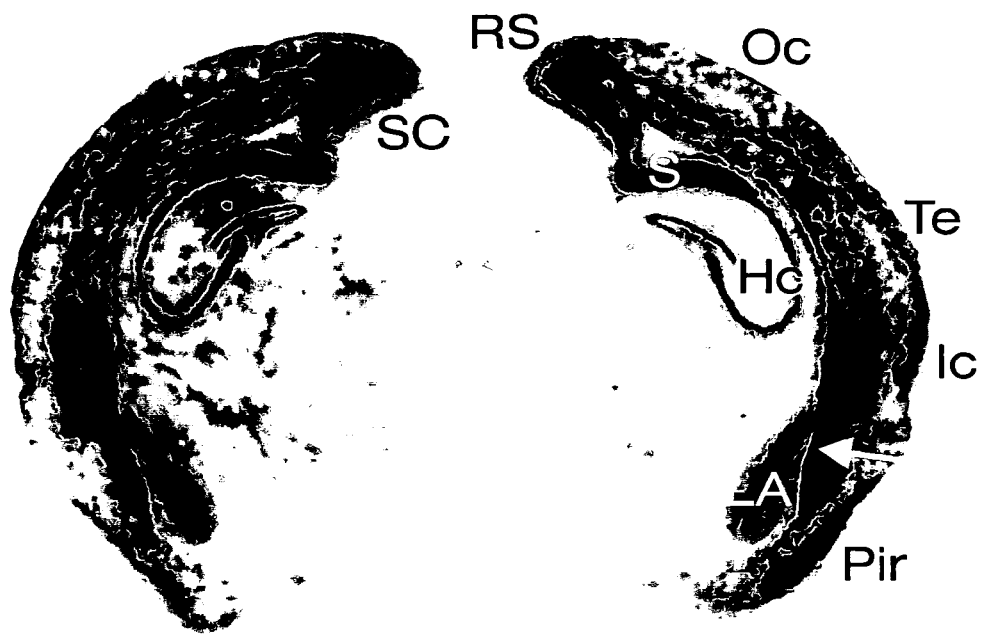
FIG. 13. The mRNA encoding neurotrypsin is shown in a coronal section of the brain of an adult mouse by in situ hybridization using DIG-labeled neurotrypsin antisense cRNA. The coronal section shows the superior colliculus (SC), the thalamus, and the hypothalamus. Labeling is seen in distinct layers throughout the neocortex (Te, temporal cortex; Oc, occipital cortex) with a more widespread labeling in the transition zones between iso- and allocortex (Ic, insular cortex; RS, retrosplenial cortex). In the allocortex, labeling is detected in the piriform cortex (Pir), with a strong labelling in the endopiriform nucleus (arrow), and in the hippocampal formation (S, subiculum; Hc, hippocampus). Strong neurotrypsin expression is also seen in the lateral amygdala (LA).

The in situ hybridization pattern detected in this way on cryosections from adult mice revealed a strong cellular expression of neurotrypsin mRNA in the gray matter of the central and the peripheral nervous system (FIG. 13). In a coronal section of an adult mouse, highest levels of neurotrypsin mRNA were found in the neocortex, the hippocampal formation, and the amygdala. If the detection sensitivity was adjusted in order to detect intermediate and low level expression, expression of neurotrypsin was also observed in the striatum, the thalamus, the hypothalamus, the cerebellum, the pons, the trigeminal ganglion, and the dorsal root ganglia. No neurotrypsin mRNA was detected in non-neural tissues. Control sections, processed with the sense probe, showed no staining. In conclusion, most, if not all, neurons express neurotrypsin mRNA, yet considerable differences in expression levels were found.

Example 6

Neurotrypsin Protein is Located in the Synaptic Areas of Many Regions of the Brain (Results Revealed by Immunocytochemistry at the Light Microscopic Level)

To generate the antigen for immunization, the catalytic domain of human neurotrypsin, containing a His-tag at the C-terminus, was produced in *E. coli*, purified on a Ni-NTA column, and refolded. Portions of 50 µg were used for immunization of a goat (primary immunizations in complete Freund's adjuvant and booster injections in incomplete Freund's adjuvant). From the immune serum, IgG was isolated by affinity chromatography on immobilized protein G. Affinity-purified IgG was obtained by affinity chromatography on the immobilized proteolytic domain of neurotrypsin.

The localization of neurotrypsin at the light microscopic level was achieved by means of standard immunocytochemical visualization methods. In brief, adult (6 to 16 week old) C57BU6 mice of both sexes were deeply anesthetized with metiofane (methoxyflurane, Pitman-Moore Inc.) and perfused through the heart for 15-20 min with fixative composed of 3.5-4% paraformaldehyde (Merck, Switzerland), 0.01-0.02% glutaraldehyde (Merck, Switzerland), and 0.2% picric acid in 0.1 M phosphate buffer, pH 7.4 (PB). The brains were placed into ice-cold PB and sectioned in the coronal plane. Sixty-micrometer-thick vibratome sections were equilibrated in 30% sucrose in PB, rapidly frozen in liquid nitrogen and thawed in PB. The sections were then preincubated in 10% normal rabbit serum (NRbS; Vector Labs, Reactolab, Switzerland) in 0.05 M Tris buffered saline, pH 7.4 (TBS) for 45 min at room temperature.

For immunolabeling, the sections were incubated in primary antibody solution (1:100) in TBS that was supplemented with 2-5% NRbS and 2% bovine serum albumin (BSA, Sigma) for 36-48 hr at 4° C. with constant shaking. The sections were then washed (4×20 min in 1% NRbS in TBS) and incubated with biotinylated anti-goat IgG (1:200, Vector Labs) for 12 hr at 4° C. followed by 3 hr incubation in an avidin-biotin-peroxidase complex (Elite ABC; 1:100, Vector Labs) at room temperature. Antigenic sites were visualized by incubation in 3,3'-diaminobenzidine (Sigma, Switzerland; 0.05% in TB, pH 7.6) in the presence of 0.0048% $H_2O_2$. The reaction was stopped by several washes in TB. The sections were mounted on gelatinized slides, air-dried, dehydrated, and coverslipped in Entelan (Merck, Switzerland). The specificity of the immunolabeling was proven by the absence of staining with preimmune serum and when the primary antibodies were omitted.

Applying this procedure of immunoperoxidase staining to tissue sections of the cerebral cortex (FIG. 14), and the hippocampus (FIG. 15A), we found that neurotrypsin was abundant in synapse-rich regions. At higher magnification, a punctate appearance of the immunostaining in the neuropil of the stratum radiatum of the hippocampal CA1 region was found (FIG. 15B). The punctate immunolabeling in a neuropil region is typical for a protein with a synaptic localization. The same pattern of immunolabeling of neurotrypsin was also observed in the neuropil of other brain regions, including the cerebral cortex, the amygdala, and the caudate putamen.

In conclusion, these results indicate a synaptic localization of neurotrypsin. The synaptic pattern of immunolabeling is found in many regions of the brain. Most prominent immunolabeling for neurotrypsin was found in regions associated with synaptic plasticity.

Example 7

Neurotrypsin Protein is Located in the Presynaptic Membrane and Within the Presynaptic Active Zone of CNS Synapses (Results Revealed by Immuno-electronmicroscopy (Immuno-EM))

To reveal the subcellular localization of neurotrypsin in CNS neurons, we used preembedding peroxidase and immunogold immuno-EM. To prepare brain tissue for immuno-EM, adult (6 to 16 week old) C57BU6 mice of both sexes were deeply anesthetized with metiofane (methoxyflurane, Pitman-Moore Inc., USA) and perfused through the heart for 15-20 min. Mice were first perfused with 0.9% saline for 1 min followed by fixative containing 3.5-4% paraformaldehyde, 0.01-0.02% glutaraldehyde, and 0.2% picric acid made up in 0.1 M phosphate buffer pH 7.4 (PB). Then brains were removed from the skull into cold PB and 70 μm thick coronal sections were cut on a vibratome.

For preembedding immuno-cytochemistry, the sections were cryoprotected in 30% sucrose, quickly frozen in liquid nitrogen, and thawed in PB. After preincubation in 20% normal rabbit serum (NRbS; Vector Labs, USA), sections were incubated in primary antibody diluted in 0.05 mM Tris buffered saline, pH 7.4 (TBS) containing 2% bovine serum albumin (BSA) and 2% NRbS at 4° C. for 2 days. For the immunogold method, the sections were incubated overnight in a 1:40 dilution of rabbit anti-goat IgG coupled to 1.4 nm gold (Nanoprobes Inc. Stony Brook, N.Y.), postfixed in 1% glutaraldehyde in phosphate-buffered saline (PBS) followed by silver enhancement of the gold particles with an HQ Silver kit (Nanoprobes Inc). For the peroxidase reaction, the sections were incubated for 4 hr at RT in biotinylated rabbit anti-goat IgG (Vector Labs) diluted 1:200 in TBS containing 1% NRbS, followed by 2 hr incubation in avidin-biotin-peroxidase complex (ABC kit; Vector Labs) diluted 1:100 in TBS. Antigenic sites were revealed using the standard 3,3'-diaminobenzidine tetrahydrochloride histostaining procedure (0.05% DAB and 0.01% $H_2O_2$ in TB, pH 7.6). The gold-silver and peroxidase-reacted sections were postfixed in 1% osmium tetroxide in PB, stained with 2% uranyl acetate, dehydrated in graded series in ethanol, and flat-embedded on glass slides in Durcupan ACM resin (Fluka) for electron microscopy.

The sections were examined first with a Leica DMR light microscope (LM). Areas of interest were cut from the slide and re-embedded. Serial thin sections were collected on pioloform-coated single-slot copper grids, and examined with a Philips CM100 electron microscope.

Figure 16:
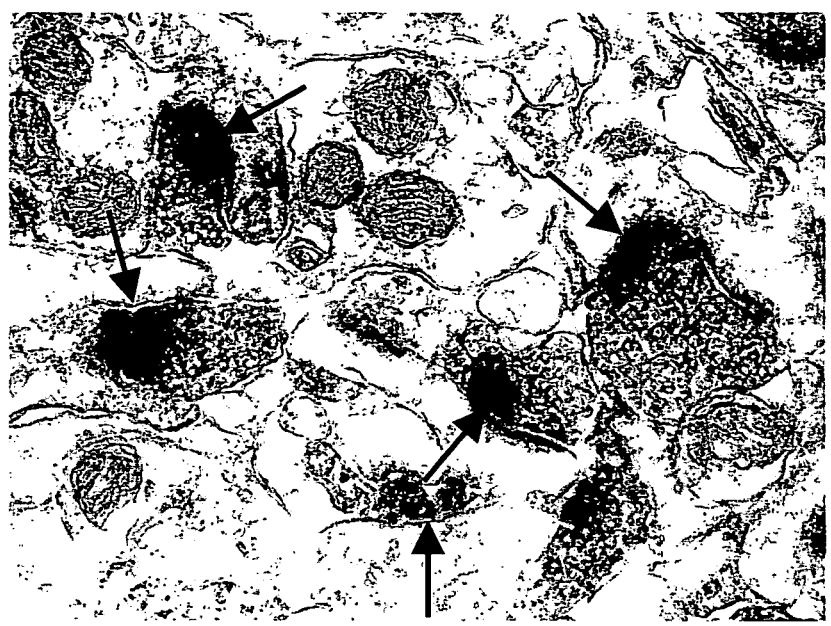
FIG. 16. The localization of neurotrypsin is shown by immuno-electron microscopy of the stratum radiatum (s.r.
Figure 16:
Figure 17:
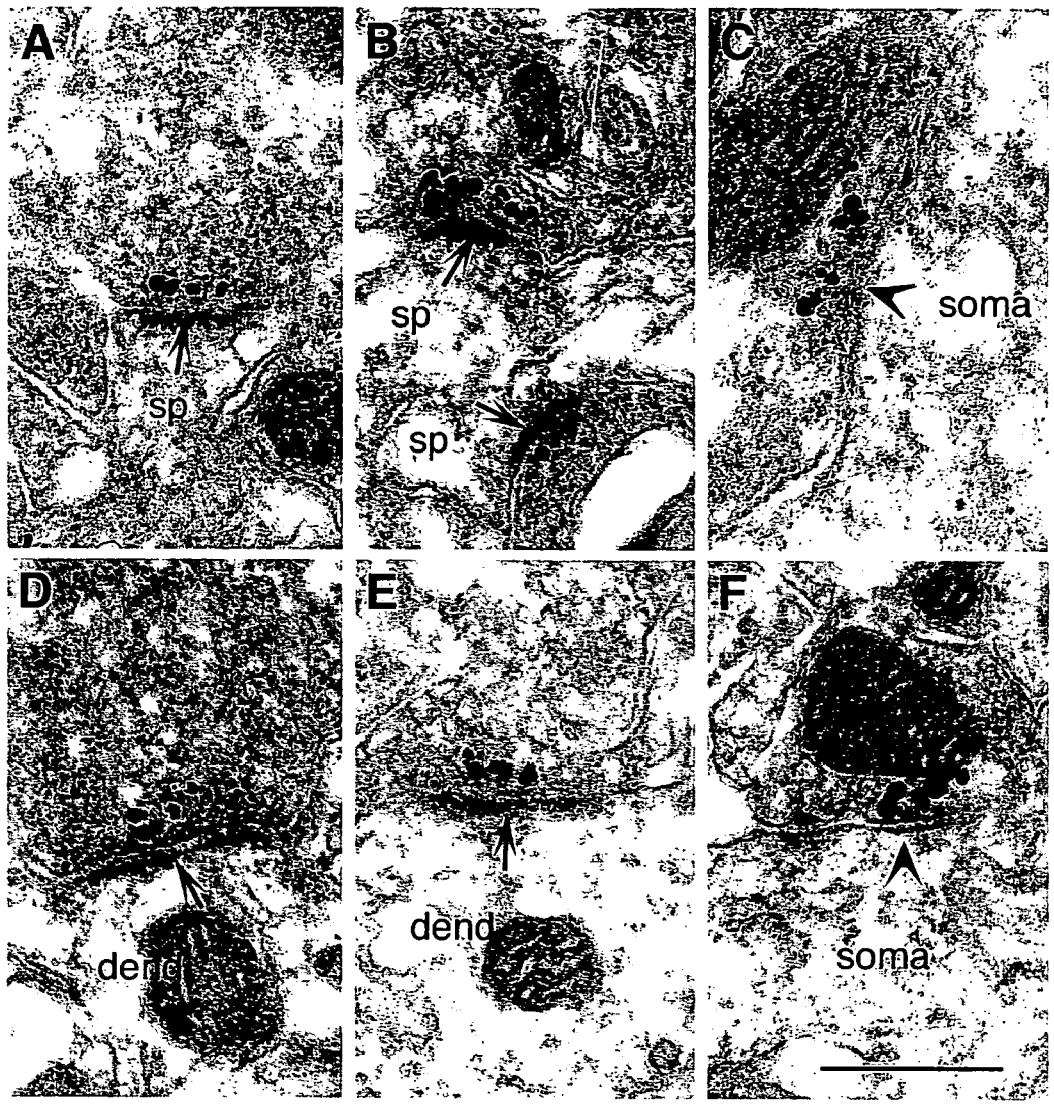
FIG. 17. The localization of neurotrypsin is shown by immunogold-electron microscopy of the stratum radiatum (s.r.
Figure 18:
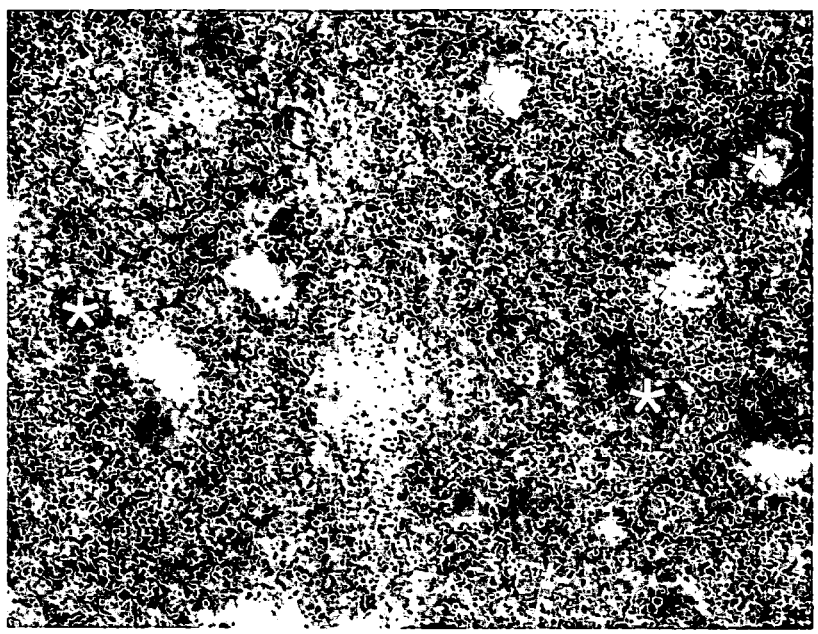
FIG. 18. The synaptic localization of neurotrypsin in the human brain is demonstrated by light- and electron-microscopic immununocytochemical visualization. Neurotrypsin was visualized in adult human cerebral cortex using preembedding immuno-EM staining with a specific, affinity-purified antibody against the proteolytic domain of neurotrypsin. (A) Immunohistochemical visualization of neurotrypsin with peroxidase-conjugated secondary antibody. The strong punctate immunolabeling of the neuropil is typical for a protein with synaptic localization. Neuronal somata (marked by asterisks) were unlabeled. (B) Preembedding immuno-EM localization by immunoperoxidase demonstrates the localization of neurotrypsin at presynaptic sites of axospinous and axodendritic asymmetric synapses in the cerebral cortex. The immunoperoxidase reaction product is associated with the presynaptic membrane and the active zone of the presynaptic terminal (arrows). (C) Immuno-gold localization of neurotrypsin at selected synapses. Note the exclusive labeling of presynaptic terminals in the region lining the synaptic cleft. Scale bars, 0.5 μm.
Figure 18:
Figure 18:

Preembedding immuno-EM with peroxidase-labeled antibodies located neurotrypsin on the presynaptic membrane, in particular in the regions of the presynaptic active zone, of synapses located on dendritic spines, dendritic shafts, and on neuronal somas (FIG. 16, A and B). No immunoreactivity was found in dendritic spines. Both asymmetric (excitatory) synapses with round vesicles and thick postsynaptic densities (PSDs) (Type 1 according to Gray, 1959) and symmetric (inhibitory) synapses with pleomorphic vesicles and thin PSDs (Type 2) exhibited neurotrypsin immunoreactivity. Preembedding immunogold staining of mouse hippocampus confirmed the localization of neurotrypsin in the region of the presynaptic active zone (FIG. 17, A-F). Immunogold-labeling of neurotrypsin was found accumulated within the presynaptic active zone of axon terminals which form asymmetric synapses with dendritic spines (FIG. 18, A and B) and dendritic shafts (FIG. 18, D and E), as well as within active zones of axon terminals which form symmetric synapse with neuronal somata (FIG. 18, C and F).

These results clearly demonstrate that neurotrypsin is a component of the presynaptic membrane in both excitatory and inhibitory synapses of the central nervous system of the mouse.

Example 8

Neurotrypsin Localization in Human Brain is Identical With Neurotrypsin Localization in Mouse Brain (Results Revealed by Immuno-LM and Immuno-EM)

The expression of neurotrypsin in the adult human brain was investigated by immunohistochemistry at the light- and electron-microscopic level. The tissue was fixed in 0.1 M sodium phosphate, pH 7.4, containing 4% paraformaldehyde, 0.025% glutaraldehyde, and 0.2% picric acid. Fifty-micrometer thick sections were cut with a vibratome. Incubations of the primary antibody (0.5-2 μg IgG/ml) were in 0.05 M Tris-Cl, pH 7.4, supplemented with 2-5% normal rabbit serum and 2-3% bovine serum albumin (Sigma), for 36-48 hr at 4° C. For immunoperoxidase localization, the sections were incubated with biotinylated anti-goat IgG (1:200, Vector Labs), followed by incubation with avidin-biotin-peroxidase complex (Elite ABC; 1:100, Vector Labs) and 3,3'-diaminobenzidine (Sigma, Switzerland; 0.05% in Tris-Cl, pH 7.6) in the presence of 0.005% $H_2O_2$. For immunogold localization, the sections were incubated with the anti-goat IgG conjugated to 1.4 nm gold particles (Nanoprobes) for 3 hr at 21° C. and then subjected to silver intensification with the LI Silver kit (Nanoprobes, USA). Finally, the sections were postfixed in 1% osmium tetroxide and 2% uranyl acetate (Fluka, Switzerland), dehydrated, and flat-embedded in Durcupan ACM (Fluka, Switzerland) for light and electron microscopic examinations.

For the specific detection of neurotrypsin, affinity-purified antibodies raised against its proteolytic domain were used. To generate the antigen for immunization, the catalytic domain of human neurotrypsin, containing a His-tag at the C-terminus, was produced in E. coli, purified on a Ni-NTA column, and refolded. Portions of 50 μg were used for immunization of a goat (primary immunizations in complete Freund's adjuvant and booster injections in incomplete Freund's adjuvant). From the immune serum, IgG was isolated by affinity chromatography on immobilized protein G. Affinity-purified IgG was obtained by affinity chromatography on the immobilized proteolytic domain of neurotrypsin.

Figure 19:
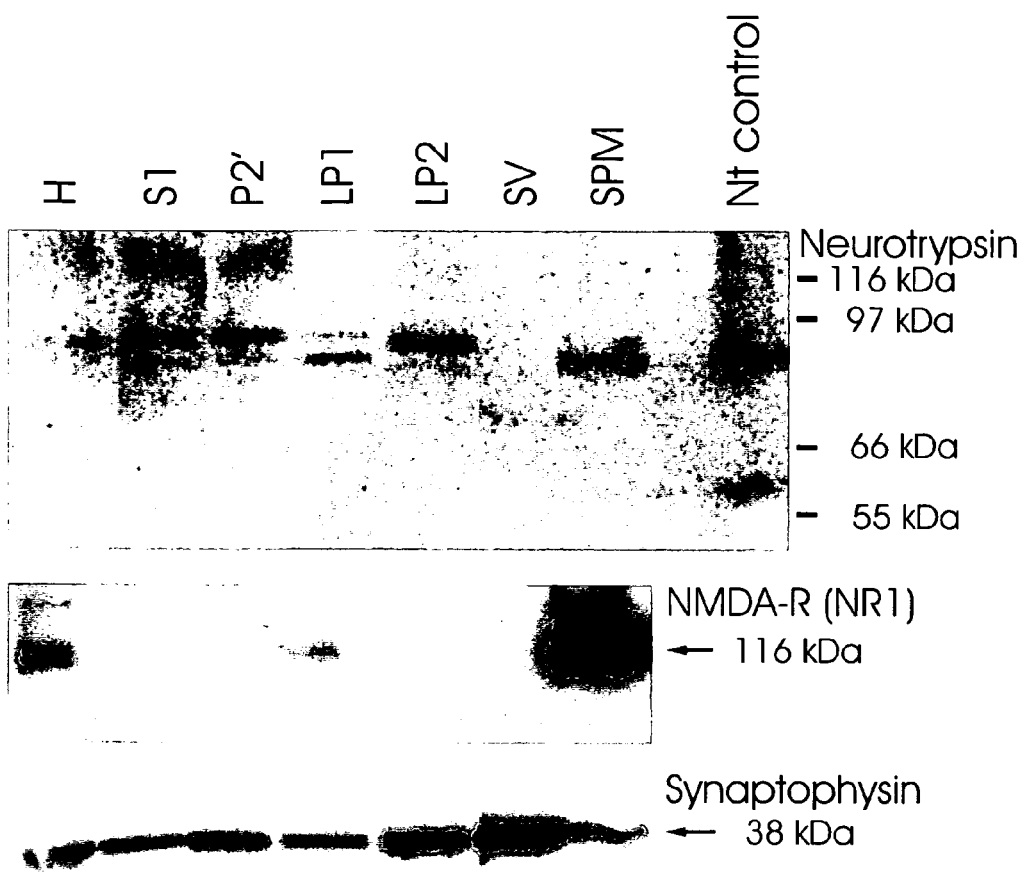
FIG. 19. The localization of neurotrypsin in synaptosomes and synaptic membranes is shown by differential centrifugation of brain homogenate. Starting with brain homogenate of wild-type mice, synaptosomes, synaptic membranes, and synaptic vesicles were isolated by differential centrifugation following established protocols. The presence of neurotrypsin in the subcellular fractions was determined by Western blotting, using a specific antibody against the proline-rich basic domain of neurotrypsin. In order to control for the correct tissue fractionation, synaptophysin, a component of the presynaptic vesicles, and NR1 (a subunit of the NMDA-type glutamate receptor), a component of the postsynaptic membrane, were tested on the same fractions. Note the enrichment of the synaptic membrane marker NR1 along the purification process, cumulating in the synaptic membrane (SPM) fraction, i.e. from the brain homogenate (H), via the homogenate supernatant free of nuclear pellet (S1), to the crude synaptosomes (P2'), to the crude synaptic plasma membranes (LP1), to the purified synaptic plasma membrane (SPM). Note also the enrichment of the synaptic vesicle marker synaptophysin along the purification process, cumulating in the synaptic vesicle (SV) fraction, i.e. from the brain homogenate (H), via the homogenate supernatant free of nuclear pellet (S1), to the crude synaptosomes (P2'), to the crude synaptic vesicles (LP2), to the purified synaptic vesicles (SV). The minor band of synaptophysin in the synaptic membrane fraction is in accordance with the expectations, because approximately 10% of the synaptophysin is located in the presynaptic membrane, due to the constant fusion of synaptic vesicles into the presynaptic membrane. The double band observed in the initial fractions (S1, P2', LP1, and LP2) indicates a processing of neurotrypsin along its secretory pathway. In the plasma membrane fraction, almost all neurotrypsin was present in the lower molecular weight form, indicating that the lower molecular weight form represents the mature form of neurotrypsin. H, brain homogenate; S1, brain homogenate supernatant free of nuclear pellet; P2', crude synaptosomes; LP1, crude synaptic plasma membrane; LP2, crude synaptic vesicles; SV, synaptic vesicles, purified with sucrose gradient; SPM, synaptic plasma membrane purified with sucrose step gradient; Nt control, P2' fraction of neurotrypsin(Serine711 Alanine)-overexpressing mouse.

At the light-microscopic level we found a high density of neurotrypsin-immunoreactive synaptic boutons in the cortical neuropil (FIG. 19A). A more detailed examination at the electron-microscopic level using peroxidase-conjugated secondary antibodies revealed strong neurotrypsin immunoreactivity in the presynaptic nerve ending of cortical synapses, with the most prominent immunoreactivity over the presynaptic membrane lining the synaptic cleft, in particular in the area of the presynaptic active zone (FIG. 19B). With gold-labeled secondary antibodies, the neurotrypsin immunoreactivity was most prominent within the presynaptic active zone (FIG. 19C). Thus, neurotrypsin is a presynaptic protein in the adult human CNS.

Example 9

Neurotrypsin is Enriched in Purified Synaptic Membranes (Results Revealed by Subcellular Fractionation and Immunochemical Detection)

To investigate the localization of neurotrypsin by an independent method, the presence of neurotrypsin in so-called synaptosomes and synaptic membranes was determined. Synaptosomes are membrane-bounded structures that are generated by subcellular fractionation. They are composed of the presynaptic terminal, including the presynaptic surface membrane, the synaptic vesicles, the synaptic mitochondria, the presynaptic cytosol, and the presynaptic cytomatrix, as well as the postsynaptic membranes, including the postsynaptic density (PSD) and the cytoplasmic area beneath the postsynaptic membrane. Thus, synaptosomes are essentially isolated synapses. To generate synaptosomes, fresh brain tissue from mice is disrupted by shearing forces, and distinct subcellular organelles and structures are isolated by differential centrifugation. This part was carried out according to the well-established and robust protocol described by Huttner and colleagues (Huttner, W. B. et al. *J. Cell Biol.* 96:1374-1388, 1983). In the second part of the procedure, the preparation and isolation of synaptic membranes out of synaptosomes, we followed the protocol worked out by Jones and Matus (Jones, D. H. and Matus, A. I., *Biochim. Biophys. Acta* 356: 276-287, 1974). Because the hypotonic disruption of synaptosomes results in the release of the presynaptic content including the synaptic vesicles, we also added a centrifugation step, in order to obtain a cleaner sample of synaptic vesicles.

The preparatory steps for the isolation of synaptosomes, synaptic membranes, and synaptic vesicles are described in detail below:

Preparation of Synaptosomes From Mouse Cerebral Cortex

The brains of 20 mice were dissected and put into ice-cold buffered sucrose. The cerebral cortices of 20 brains were pooled and their total weight was determined. The pooled brains were homogenized in 50 ml of buffered sucrose (composed of 320 mM sucrose in 4 mM Hepes-NaOH, pH 7.3) in a glass-Teflon homogenizer (12 strokes, 900 rpm). This process was repeated with another 20 mouse brains. The two homogenates were then pooled and 40 ml of buffered sucrose was added to a final homogenate of approximately 150 ml. The homogenate was centrifuged for 10 min at 800 g. The supernatant (S1) was removed and kept on ice; the pellet (P1) was resuspended in 50 ml buffered sucrose. The resuspended P1 was centrifuged again for 10 minutes at 800 g. The resulting supernatant S1' was combined with the supernatant S1 and centrifuged for 15 min at 9,200 g. The supernatant (S2) was discarded and the pellet (P2) was resuspended by gently vortexing. The resuspension of P2 was done very carefully only with the upper whiter part of the pellet. This upper part of the pellet is distinct from the lower part by a brighter color. The lower (and darker) portion of the pellet consists mainly of mitochondria and was discarded.

The suspension was adjusted to 120 ml of buffered sucrose, and centrifuged for 15 min at 10,500 rpm (10,200 g). The supernatant (S2') was removed. The pellet (P2') was resuspended in 13 ml of buffered sucrose (crude synaptosomal fraction), and the suspension was transferred into a glass-Teflon homogenizer. The upper part of the pellet represents the synaptosomes, which were then lysed by adding 117 ml of ice-cold water. The whole suspension was immediately subjected to homogenization (8 strokes, 3,000 rpm). The resulting P2' lysate (L) was poured rapidly into a beaker containing 1 ml of 1 M HEPES-NaOH buffer (pH 7.4). This suspension was stirred for 30 minutes on a magnetic stirrer, while being kept ice-cold. Subsequently the suspension was centrifuged for 20 min at 25,0000 g (16,500 rpm using the SS-34 rotor). The supernatant (LS1, lysate supernatant) was collected for preparing synaptic vesicles. The lysate pellet (LP1) was taken for preparing synaptic membranes. This procedure is based on the method worked out by Huttner and colleagues (Huttner, W. B. et al. *J. Cell Biol.* 96:1374-1388, 1983).

Preparation of Synaptic Plasma Membranes (SPM) from the LP1 (Plasma Membrane Enriched) Fraction.

The LP1 fraction was resuspended in 4 ml of 7.5 mM HEPES-NaOH, pH 7.2, and 8 ml of 48% (w/w) sucrose (composed of 48% w/w sucrose in 7.5 mM HEPES-NaOH, pH 7.2) was added to obtain a volume of 12 ml and the final concentration of 34% (w/w) sucrose. This cushion of 34% (w/w) sucrose solution was overlayed with a solution of 28.5% sucrose (composed of 28.5% w/w sucrose in 7.5 mM HEPES-NaOH, pH 7.2). On top of this, approximately 2 ml of 10% sucrose solution (composed of 10% w/w sucrose in 7.5 mM HEPES-NaOH, pH 7.2) were overlayed. This step gradient was centrifuged in a 13 ml tube for 110 min in a Beckman SW41 rotor at 22'100 rpm (60'000 gav). At the end of this centrifugation, the synaptic membranes form a band at the 28.5%/34% sucrose interface. This band was collected from the sucrose density gradient by introducing a needle through the side of the centrifuge tube. The synaptic membranes were diluted with 10 ml of 7.5 mM HEPES-NaOH pH 7.2. followed by centrifugation for 30 min in a Beckman SW41 rotor at 29'000 rpm (100'000 gmax). The pellet containing the synaptic membranes was resuspended in 1 ml of 7.5 mM HEPES-NaOH pH 7.2.

This procedure was initially developed and published by Jones and Matus (Jones, D. H. and Matus, A. I., *Biochim. Biophys. Acta* 356: 276-287, 1974). For a description of the method in form of a protocol see the book chapter by Phelan and Gordon-Weeks (Pheland, P., and Gordon-Weeks, P. R.: Isolation of synaptosomes, growth cones, and their subcellular components. In: *Neurochemistry, a practical approach,* $2^{nd}$ edition, 1997, Chapter 1, Edited by A. J. Turner and H. S. Bachelard. IRL Press at Oxford University Press).

Preparation of Synaptic Vesicles (SV) from LS1.

The supernatant (LS1) was transferred into 12 10-ml polycarbonate tubes, and centrifuged at 4° C. for 2 hr at 50,000 rpm (165,000 g) in a Beckman Ti50 rotor. The resulting supernatant (LS2) was discarded and the pellet (LP2) collected. The pellet (LP2) was resuspended in a total volume of 4 ml of 40 mM sucrose. The suspension was subjected to 10 up-and-down strokes in a glass-Teflon homogenizer at 1,200 rpm. Subsequently, the supernatant was forced 5 times back and forth through a 25-gauge needle attached to a 10-ml syringe. This suspension was then layered on top of a linear continuous gradient (generated in a 38.5-ml polyclear thin-wall centrifuge tube from a 800 mM sucrose and a 50 mM sucrose solution), and centrifuged for 5 hr in a Kontron TST 28.38 rotor at 22,500 rpm. Fractions were collected from the sucrose density gradient by introducing a needle through the side of the centrifuge tube. The fractions corresponding to the 200-400 mM sucrose regions (enriched in synaptic vesicles and synapsin I, SG-V) were pooled.

In summary, the preparation of the synaptic membranes consisted in six major steps:
1) homogenization of rat cerebral cortex;
2) differential centrifugation of the homogenate to obtain a crude synaptosomal fraction (P2'); 3) hypoosmotic lysis of the synaptosomes to release synaptic vesicles and cytoplasmic components from the synaptic surface membranes (immediately after hypoosmotic lysis, this fraction is termed "crude synaptosomal lysate";
4) differential centrifugation of the crude synaptosomal lysate to obtain a crude synaptic vesicle fraction and a crude synaptic membrane fraction;
5) purification of the synaptic vesicles by continuous sucrose density gradient centrifugation; and
6) purification of the synaptic membrane fraction from the crude synaptic membrane fraction by centrifugation on a sucrose step gradient.

Homogenization and subsequent steps were carried out in low ionic strength media because neurotrypsin was released into the supernatant at moderate and high ionic strength.

The aim of the primary subfractionation of the brain homogenate was to remove small vesicles other than the vesicles contained in nerve endings. Upon osmotic lysis of the P2' fraction, both the small vesicles released into the medium from the synaptosomes and the larger synaptic membranes originating from the surface membranes of the synaptosomes can readily be separated.

Figure 20:
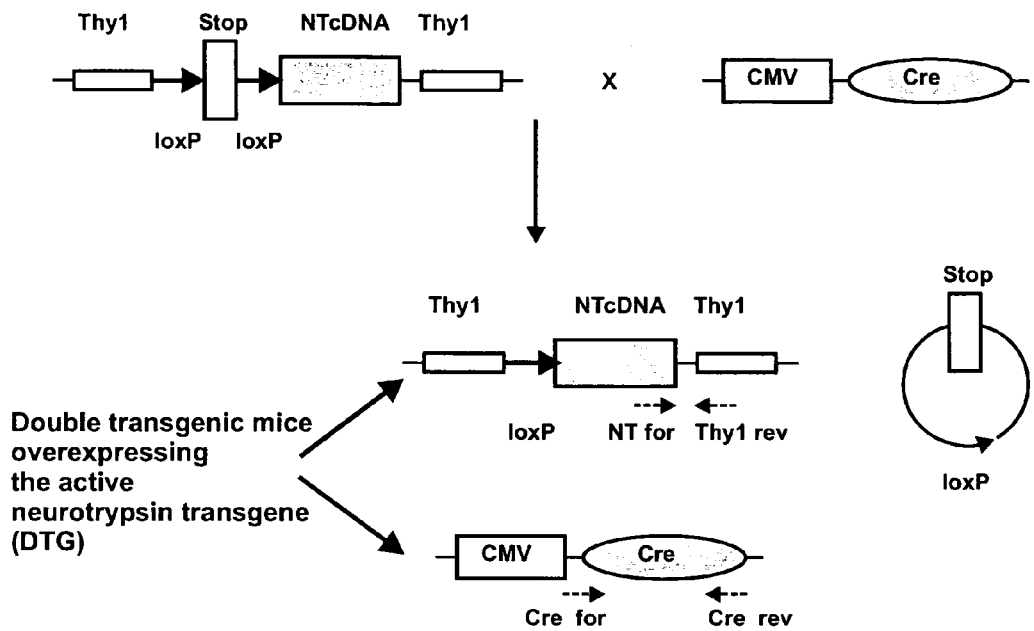
FIG. 20. Transgenic constructs and the generation of neurotrypsin-overexpressing mice. On the upper left the figure the construct for the conditional overexpression of neurotrypsin is shown. Conditional overexpression indicates that the transgene is inserted into the mouse genome in an inactive form. In this conditional transgene, the coding part of the neurotrypsin cDNA was incorporated into the Thy1 gene and, thus, put under the control of the Thy1 promoter. In the graph, the first box marked by Thy1 indicates the transcription-regulating promoter at the 5' end of the Thy-1 gene. The second box marked by Thy1 indicates the 3' terminal sequences of the Thy1 gene. Between the Thy-1 promoter and the cDNA encoding neurotrypsin, a stop codon flanked by two IoxP sequences was inserted. Transcription from the Thy-1 promoter of this transgene, thus, stops before reaching the coding sequence of neurotrypsin. The inactive transgene can be converted into an active transgene by Cre recombinase. Cre recombinase promotes recombination at the IoxP sites and, thus, excision of the transcriptional stop sequence. On the upper right side, the construct for expression of Cre-recombinase under the control of the cytomegalovirus (CMV) promoter is shown. Therefore, activation of the inactive transgene can be obtained by crossing the mice containing the inactive Thy1-neurotrypsin (inact.Nt) transgene with the mice containing the CMV-Cre transgene. If a heterozygous inact.Nt mouse is crossed with a heterozygous CMV-Cre mouse, the double-transgenic mice among the offspring express the Thy1-neurotrypsin transgene in the activated form. The expressed Cre-recombinase deletes the transcriptional stop sequence by promoting recombination at the IoxP sequences. One IoxP sequence remains within the activated Thy1-neurotrypsin transgene. The removed segment composed of the other IoxP sequence and the transcriptional stop sequence is shown on the right. The mice were genotyped with the PCR method. The dashed arrows mark the region of the oligonucleotide primers used in the PCR.

To examine the subcellular distribution of neurotrypsin, proteins from subcellular fractions were separated by SDS-polyacrylamide gel electrophoresis, transferred to nitrocellulose, and reacted with an antibody against neurotrypsin (Western blotting). FIG. 20 shows the results of Western blots obtained when equal amounts of protein from the various subcellular fractions were analyzed for the presence of neurotrypsin. It can be seen that, on Western blots of subcellular fractions, neurotrypsin occurs as two bands with apparent molecular weight of 90 kD and 85 kD. Both bands were recognized by the polyclonal antiserum SZ177 against the proline-rich basic domain of neurotrypsin, and increased following the purification steps. The same enrichment of neurotrypsin immunoreactivity was demonstrated when detected with polyclonal antibody G73 that recognizes the C-terminal protease domain of neurotrypsin. Interestingly, from 90 kD and 85 kD species enriched in the synaptosomes (P2'), only the 85 kD form is found in the synaptic plasma membranes. This could indicate a processing step of neurotrypsin associated with its translocation from intracellular secretory vesicles to the synaptic plasma membrane.

In order to control for the correct tissue fractionation, synaptophysin, a component of the presynaptic vesicles, and NR1 (a subunit of the NMDA-type glutamate receptor), a component of the postsynaptic membrane, were tested on the same fractions. In accordance with the expectations for a successful preparation of synaptic plasma membranes, the synaptic membrane marker NR1 was enriched along the purification process, cumulating in the synaptic membrane (SPM) fraction. Purification proceeded from the brain homogenate (H), via the homogenate supernatant (free of nuclear pellet) (S1), to the crude synaptosomes (P2'), to the crude synaptic plasma membranes (LP1), to the purified synaptic plasma membrane (SPM). Likewise, the synaptic vesicle marker synaptophysin was enriched along the purification process, cumulating in the synaptic vesicle (SV) fraction, i.e. from the brain homogenate (H), via the homogenate supernatant (free of nuclear pellet) (S1), to the crude synaptosomes (P2'), to the crude synaptic vesicles (LP2), to the purified synaptic vesicles (SV). The minor band of synaptophysin in the synaptic membrane fraction is in accordance with the expectations, because approximately 10% of synaptophysin is located in the presynaptic membrane, due to the constant fusion of synaptic vesicles with the presynaptic membrane.

In summary, these results indicate that both neurotrypsin is localized in the synapse, and primarily associated with synaptic plasma membranes. The majority of the synaptic vesicles do not contain neurotrypsin. However, the presence of neurotrypsin in the crude synaptic vesicle fraction (LP2) indicates the presence of neurotrypsin in a minor population of vesicles, comprised in the crude vesicular fraction, but lost in the final purification of the presynaptic vesicles. These results are in accordance with the localization of neurotrypsin in the presynaptic membrane by immuno-EM (Experiments 3 and 4).

Example 10

Overexpression of Neurotrypsin in Neurons Using Transgenic Mice Technology

The overexpression of a gene in a transgenic mouse is used widely to study the function of a protein in vivo. For the first series of experiments, neurotrypsin was overexpressed under the control of the promoter of the Thy-1 gene. The Thy-1 gene is expressed in the nervous system of the mouse relatively late (postnatal day 4-10, depending on the location). Therefore, the expression of neurotrypsin under the control of the Thy-1 promoter (Gordon J. W. et al., *Cell* 50: 445-452, 1987) ensures that the earlier developmental stages are not perturbed by the presence of excessive amounts of neurotrypsin. This point is essential. Neurotrypsin is expressed in some regions of the developing nervous system relatively early and, thus, it could play a role in early developmental functions, such as cell migration, axon outgrowth, and synapse formation (Wolfer, D. P. et al., *Molec. Cell. Neurosci.* 18: 407433, 2001). By using a late onset promoter, we intended to prevent perturbations of early stages of neurogenesis in the transgenic animals. However, depending on the aim of an investigation, other promoters may be used as well.

The construct of the first generation transgene was based on an expression vector for Thy-1 in which the translated region of Thy-1 had been substituted by a XhoI linker (Gordon, J. W. et al., *Cell* 50: 445-452, 1987). The full-length cDNA of neurotrypsin was inserted into the Thy-1 expression vector at the XhoI linker site by a blunt-end ligation and the orientation controlled by means of a restriction enzyme digestion and nucleotide sequence analysis. The plasmid is rescued and the fragment to be used for the injection into the pronucleus of fertilized mouse oocytes was cut out by digestion at the two flanking PvuI sites. The injection fragment was separated by electrophoresis in a 1% agarose gel, the band purified with a QIAEXII-kit, and the DNA eluted from the QIAEX particles with injection buffer. The generation of transgenic mice was achieved by pronuclear injection following standard protocol. The litters were screened for the presence of the transgene by polymerase chain reaction (PCR) and Southern blotting.

We found that transgenic mice that overexpressed the neurotrypsin protein in CNS neurons died shortly after birth. To overcome this problem, we generated a second generation of transgenic mice. These mice bore a conditional transgene that was inactive as long as it had not been activated. To generate an inactive, but activatable, transgene, a removable transcriptional stop sequence was introduced before the neurotrypsin-cDNA. This sequence causes transcription to come to a halt. To make the stop sequence removable, an approach based on the Cre/IoxP recombination system was chosen (Sauer B. et al., *Proc. Natl. Acad. Sci.* (*USA*) 85: 5166-5170, 1988). The Cre (Cre-recombinase) protein is encoded by the *Escherichia coli* bacteriophage P1, and efficiently promotes both intra- and intermolecular recombination of DNA in *E. coli*. Recombination occurs at a specific site called IoxP (Hamilton, D. L. and Abremski, K., *J. Mol. Biol.* 178: 481-486, 1984). This characteristic feature of the Cre recombinase allows deletion and insertion of specifically denoted strings of DNA between the IoxP sequences. It can be used to generate specific functional mutations in vivo. This construct was then inserted between the regulatory subunits of the Thy-1 gene (Chen S. et al., *Cell* 51: 7-19, 1987).

Figure 21:
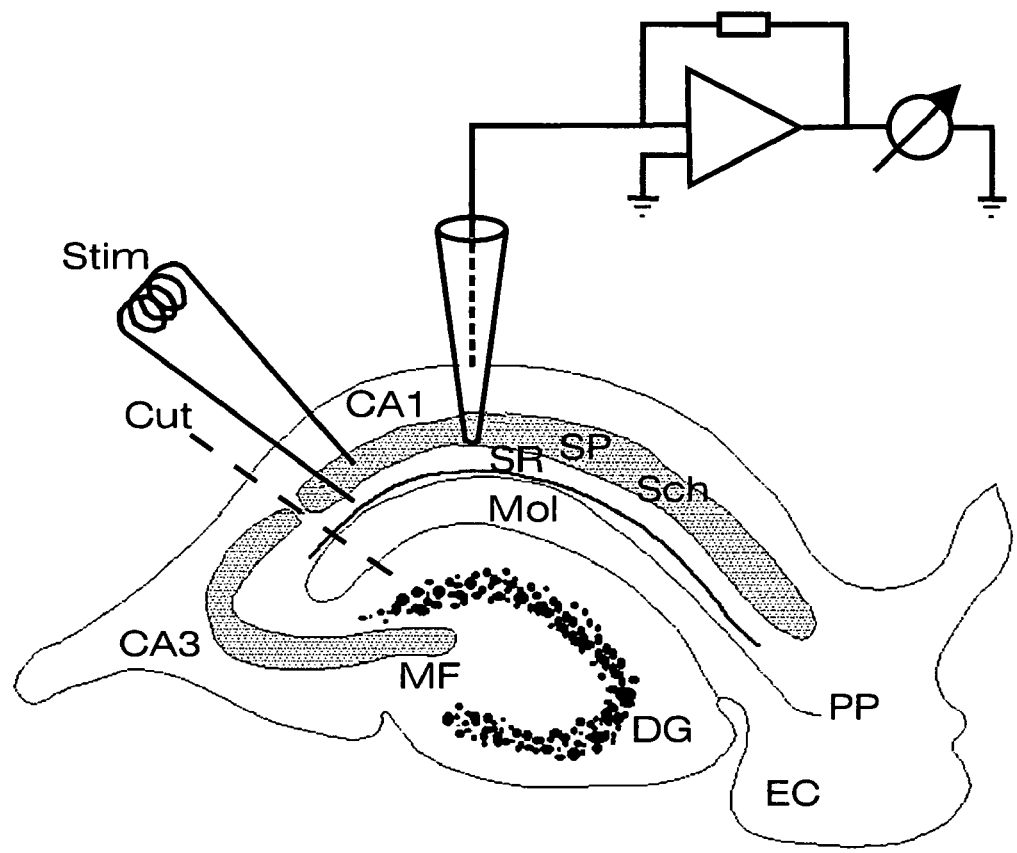
FIG. 21. Schematic representation of a hippocampal slice and the electrode positions used in electrophysiological recordings. The electrophysiological investigations were performed on the Schaffer collateral pathway of the hippocampus. Positions of the stimulating (Stim) and recording electrodes and the cut introduced between the CA1 and the CA3. (DG, dentate gyrus; EC, entorhinal cortex; MF, mossy fibers; Mol, stratum moleculare; PP, perforant path; Sch, Schaffer collaterals; SP, stratum pyramidale; SR, stratum radiatum. The actual recordings took place at the border between the stratum radiatum and the stratum lacunosum-moleculare.

Transfected heterozygous mice with this gene construct were crossed with heterozygous mice carrying Cre-recombinase DNA attached to a cytomegalovirus (CMV) promoter to receive double transgenic (neurotrypsin-overexpressing) mice (see FIG. 21). This promoter is continuously active in vivo and the expressed Cre-recombinase promotes recombination at the two IoxP sequences. This procedure removes the transcriptional stop sequence from the inactive transgene and allows transcription of the neurotrypsin cDNA. The transgenic mice were genotyped by PCR and Southern blot hybridization. The DNA for the PCR was extracted from the tail of the mice.

The position of the PCR primers was chosen so that the detection of the native murine neurotrypsin gene was prevented. The 3'-primer corresponded to a DNA sequence inside Thy-1.2 and the 5'-primer to a sequence inside the neurotrypsin cDNA. This DNA fragment is unique to the neurotrypsin transgene. The primers for detection of the Cre insert were both equivalent to DNA sequences derived from inside the Cre gene, because Cre usually does not exist in mice. By this procedure, three mouse lines overexpressing the human neurotrypsin and four lines overexpressing the mouse neurotrypsin were raised. The expression of the transgene was verified at the mRNA level by Northern blotting and in situ hybridization and at the protein level by Western blotting. A typical overexpression was in the order of 2- to 3-fold.

In order to control for the dependence of the neurotrypsin-mediated alterations on the catalytic function of neurotrypsin, transgenic mice overexpressing an inactive form of neurotrypsin under the same (Thy-1) promoter were generated. Inactive neurotrypsin can readily be generated by mutating the essential active site serine 711 to an alanine. Because in all serine proteases, the active site serine is involved in a covalent intermediate of the proteolytic reaction, its mutation results in a complete loss of catalytic function. The transgenic mice overexpressing the inactive form of neurotrypsin were healthy and did not exhibit any abnormalities.

By the same method, transgenic animals expressing full-length neurotrypsin, as well as other truncated forms of neurotrypsin or mutated forms of neurotrypsin (point mutations or deletion mutations) may be generated. Instead of the Thy-1 promoter, other promoters may be used, including promoters driving transgene expression in particular subpopulations of neurons, such as the promoter of the Purkinje cell-specific L7 protein or the promoter of the limbic system-specific protease neuropsin. Alternatively, transgene expression may be put under the control of inducible promoters.

Example 11

Figure 22:
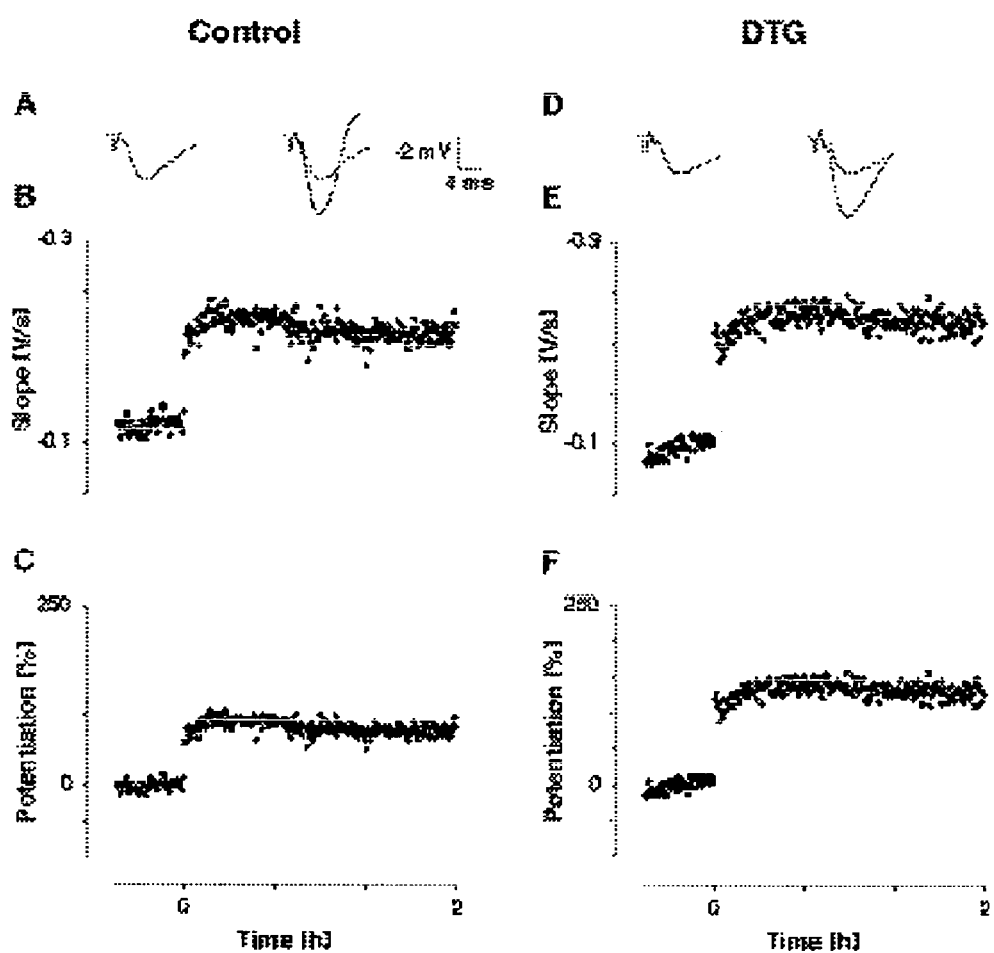
FIG. 22. fEPSP-peak time courses of a typical LTP induction in hippocampal slices of control and neurotrypsin-overexpressing mice. (A) Means of the raw fEPSP from a hippocampal control slice before and after induction of LTP: The first trace corresponds to 60 stimulations during baseline recording, the second to 240 stimulations after the induction of LTP. The dashed line in the second trace represents the baseline trace. (B) The fEPSP was evoked and recorded every 30 seconds, and the peak amplitudes represented by the middle third of the initial fEPSP slopes were displayed with respect to time. LTP induction was at time zero. (C) Normalized fEPSP amplitudes: The absolute fEPSP amplitudes were normalized to the mean of the 60 baseline recordings before time zero and expressed as percentage of potentiation. The mean of the baseline recordings was set to zero % potentiation. (D) Means of the fEPSP from a hippocampal slice of a neurotrypsin-overexpressing mouse: The fiber volley, which is somewhat larger here than in the control experiment, can be discerned easily. The dashed line in the second trace represents the baseline trace. (E) Recording of the fEPSP amplitudes from a hippocampal slice of a neurotrypsin-overexpressing mouse. F: Normalized fEPSP amplitudes. In this hippocampal slice of the neurotrypsin-overexpressing mouse (DTG), the fEPSP reached and maintained a higher percentage of potentiation than in the slice of the control mouse.

Increased Levels of Neurotrypsin in CNS Neurons Result in Enhanced Long-term Potentiation Long-term potentiation (LTP) is due to an increase in synaptic efficacy after an induction paradigm. It is considered a cellular correlate of memory and learning. We induced and measured LTP in the CA1 region of hippocampal slices. An illustration of the position of the electrodes for stimulation and recording is given in FIG. 22. In essence, LTP in other CNS regions, such as the neocortex or the amygdala could also be measured. We restricted our investigation to the hippocampus, since LTP in this area is well-defined and—understood, and accessible to extracellular recordings of field potentials (fEPSPs).

Hippocampal slices were prepared from 17 to 32 day old neurotrypsin-overexpressing and wildtype mice, which were sacrificed by decapitation using a guillotine. The methods for killing and tissue preparation had been approved by the local veterinary authorities and the animal ethics committee. The brains were quickly removed and cooled in ice-cold artificial cerebrospinal fluid (ACSF), which was constantly aerated with 5% $CO_2$ and 95% $O_2$ (oxycarbon). Both hemispheres were glued on the cut surfaces with cyanoacrylic glue (Loctile 406, Koenig AG, Dietlikon, Switzerland) onto a horizontal stage of a tissue slicer (Vibratome® 1000, TPI, Evergreen, Mo., USA) and parasagittal slices cut at a thickness of 300-400 µm in ice-cold ACSF. The tissue other than the hippocampus and neocortex was removed from the slices, which were then incubated for 1 hr at 34° C. and stored at room temperature for later use.

One of the slices was then transferred to an interface chamber (Haas, H. L. et al., *J. Neurosci. Methods* 1: 323-325, 1979) and laid out on lens cleaning tissue (Whatman International Ltd, Maidstone, England). Recordings commenced 20 minutes later at 35±1° C. in the humidified chamber gassed with oxycarbon fEPSPs were evoked in the Schaffer collaterals using bipolar twisted pair electrodes made from insulated 25 µm diameter tungsten wire (Goodfellow, Huntingdon, England) connected to a Isolator-11 constant-current stimulator (Axon Instruments, Union City, USA). Stimulus currents were adjusted to evoke a fEPSP of about one third of the maximal slope and were typically <100 µA at 20-50 µs duration. The fEPSPs were recorded with patch-electrodes pulled from borosilicate glass (2 mm OD, 1 mm ID, Hilgenberg, Malsfeld, Germany) on a P97 puller (Sutter, Novato, USA) to a resistance of 1-2 MΩ when filled with 2 M NaCl using an Axoclamp 2B amplifier (Axon Instruments, Union City, USA). Recordings were amplified $10^4$ times after a sample-and-hold step, filtered at 10 kHz using an 8-pole Bessel filter (Design JCSMR, ANU, Australia), and digitized at 20 kHz using a TL-1 interface running PClamp 6 software (Axon Instruments, Union City, USA) on a Pentium II computer.

fEPSPs were evoked in the Schaffer collaterals at 0.03 Hz. CA3 was routinely cut off. Long-term potentiation was induced after a control period of 30 minutes with a "saturating" paradigm consisting of 4 bursts of tetani at 100 Hz for 1 s separated by 20 s. The fEPSP was monitored for at least 2 hr after induction.

Data were transferred to a Macintosh (Apple computer), and analyzed using custom-made software written for IGOR Pro 4.0 (Wavemetrics, Lake Oswego, USA). The slope of the EPSP was measured at the steepest part, typically within the middle third of the voltage deflection (Moser, E. I. et al., *Science* 259:1324-1326, 1993). The slope was estimated by fitting a line to the data points within this interval of 0.3-1.2 ms. Slopes were then normalized to control values and expressed as a percentage increase where 0 represents no change.

Data from different experiments were pooled according to the genetic make-up of the animals into either the wildtype or neurotrypsin-overexpressing group. The average and standard deviation time courses were calculated for the two groups. Significance ($p<0.05$) was assessed using Student t-test.

22 fEPSP experiments with hippocampal slices from 12 wild-type litter mates and 31 with slices from 16 neurotrypsin-overexpressing mice were obtained. Two examples of typical experiments are shown from a wild-type (FIG. 23, A-C) and neurotrypsin-overexpressing (FIG. 23, D-E) mouse. In A and D, the time courses of the average fEPSPs are illustrated above the corresponding recording periods; the dotted lines indicate the recording during control conditions. Each dot in the two time courses represents the slope of the fEPSPs recorded every 30 seconds. In B and E, the absolute values of the slope are given, and in C and F, the same values are normalized to control values.

FIGS. 23C and F show the control period, during which there was a slight but not significant run-up of the control response, which was somewhat stronger in slices of neurotrypsin-overexpressing mice. LTP was induced at time zero with the 3 distinct phases associated with LTP: first, the induction phase. It coincides with the time of the tetani and is not illustrated, because no sensible value for the EPSP slope can be measured. Second, LTP expression is marked by an immediate increase in fEPSP slope to a value of about 100% after which, as shown in FIG. 23E, it decays (post-tetanic potentiation, PTP) and rebounds to larger values afterwards.

Figure 24:
FIG. 24. Demonstration of the reverberating activity observed in the hippocampus of neurotrypsin-overexpressing mice. (A) Means from fEPSP traces from a slice of a neurotrypsin-overexpressing mouse a) The trace was obtained from 60 baseline recordings b) The trace was obtained from 240 recordings after induction of LTP. (B) Means from fEPSP traces from a control slice a) The trace was obtained from 60 baseline recordings b) The trace was obtained from 240 recordings after induction of LTP. The dashed lines in Ab and Bb represent the previous trace, taken from Aa and Ba, respectively.
Figure 24:
Figure 24:
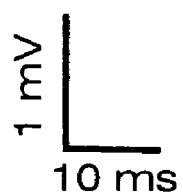
Figure 24:
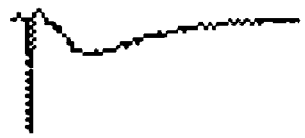
Figure 24:

The neurotrypsin-overexpressing mice showed a significant and persistent increase in slope during the first hr after PTP had ceased. Third, maintenance of LTP was expressed during the whole time of recording but got smaller with time, more so in the wild-type littermates than in the neurotrypsin-overexpressing mice. Two normalized average time courses (wild-type and neurotrypsin-overexpressing) were calculated from all valid experiments, and are illustrated in FIG. 24. It shows a greater degree of LTP in the neurotrypsin-overexpressing than in the wild-type mice. Significance based on a t-test is indicated by a dot above the appropriate point in time. The increase in LTP at two hr of recording was 122±20% and 83±12% for neurotrypsin-overexpressing and wildtype mice, respectively. This result indicates that in transgenic animals, synaptic efficacy is increased by 68±15% compared with wild-type littermates.

In the present study, synaptic efficacy at the CA3-CA1 synapses in acute slices of hippocampus was assessed using an electrophysiological assay (change in fEPSP). The main finding is, that after a saturating induction paradigm (Baranes, D. et al., *Neuron* 21:813-825, 1998), LTP is significantly increased in neurotrypsin-overexpressing mice when compared with the wild-type litter mates (122±20 vs. 83±12%). The amount of LTP in wild-type mice, with the genetic background of C57BL/6J inbred mice, is consistent with results obtained in experiments characterizing LTP in different strains of inbred mice (Nguyen, P. V. et al., *J. Neurophysiol* 84: 2484, 2000; Nguyen, P. V. et al., *J. Neurosci.* 20: 6077-6086, 2000). This characteristic of neurotrypsin-overexpressing mice is indicative that, indeed, the action of neurotrypsin is at the synapse. These results are also in line with other studies, in which extracellular proteases were implicated in increased LTP (Baranes, D. et al., *Neuron* 21: 813-825,1998; Madani, R. et al., *EMBO J.* 3007-3012,1999).

Example 12

Increased Levels of Neurotrypsin in CNS Neurons Result in Reduced Cell Capacitance in Postsynaptic Targets (Results Revealed by Electrophysiological Recordings)

Figure 25:
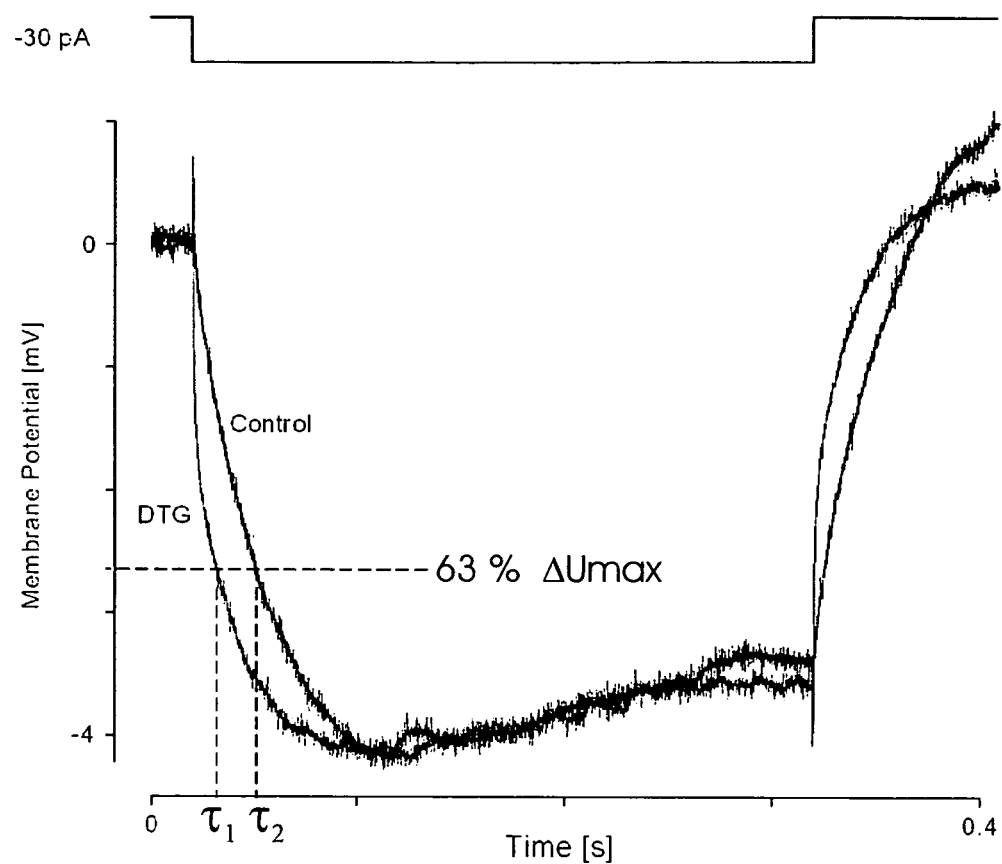
FIG. 25. Charging curve of pyramidal cells in the CA1 region of the hippocampus. A current clamped at 0.03 nA was injected 0.3 seconds in the soma of pyramidal CA1 cells of the hippocampus through the patch pipette and the resultant change in the membrane potential was measured during 0.3 seconds. Displayed by the dashed lines is the 63% level of the maximum voltage change and the corresponding time.

When evoking fEPSPs, reverberating activity could be observed in hippocampal slices of neurotrypsin-overexpressing mice at much lower stimulus intensities than in slices of control litter mates: Multiple negative-positive going voltage deflections were observed, particularly after induction of LTP, i.e. after an increase in synaptic efficacy. As shown in FIG. 25, the mean fEPSP traces from a hippocampal slice of a neurotrypsin-overexpressing mouse exhibited reverberations after induction of LTP, a noticeable difference compared to control conditions where there was a less complex response. These reverberations persisted even if CA3 was cut off, and therefore must have been produced in CA1/entorhinal cortex alone. This observation led us to investigate changes in excitability at the single cell level.

Whole-cell patch clamp recordings of CA1 pyramidal cells were done in a submerged chamber with hippocampal slices prepared the same way as described in the previous example. Individual neurons were visualized with an Axioscope microscope (2F, Zeiss, Jena, Germany) fit with differential interference contrast optics using infrared illumination (Stuart, G. J. et al., *Pflügers Archives* 423: 511-518,1993). The chamber contained ACSF oxygenated by oxycarbon as superfusate (2 ml/min). The chamber was maintained at 35-36° C., which is near physiological temperature. Patch-pipettes (3-5 MΩ) were pulled on a P97 puller (Sutter, Novato, USA) and filled with (in mM) 115 K-gluconate, 20 KCl, 10 HEPES, 10 phosphocreatine, 4 ATP-Mg, 0.3 GTP and 13.4 biocytin titrated to pH 7.2 with KOH. Biocytin was used as a marker for subsequent histological processing (see also next experiment).

We obtained basic electrophysiological properties of the action potential (AP), input resistance ($R_i$) and whole-cell capacitance ($C_m$) of the cell recorded. To determine height, width at half maximal amplitude (half width) and threshold current of action potentials, short current steps (5 ms) were injected into the cell soma and the resultant voltage deflection was measured. The current was increased in steps of 10 pA and the current, which produced APs 50% of the time, was defined as the threshold current. The membrane potential at which a regenerative action potential was initiated was also measured.

The results are summarized in Table 1. The resting potential ($V_m$) was measured when breaking into the CA1 pyramidal cells, which were chosen according to their appearance on the TV monitor. On average, $V_m$ was −69±1 in transgenic and −67±1 mV for wild-type animals; both values were not significantly different. The following parameters associated with action potentials were also not different: half width and voltage threshold. However, action potential height (105±2 versus 110±2 mV; p=0.05) and threshold current (−0.40±0.04 versus −0.29±0.02 nA; p=0.005) differed significantly, indicating that a smaller current can produce action potentials in transgenic than in wild-type mice. The increased height might suggest that the charging of the membrane is faster in transgenic animals than in wild-type mice and thereby producing a slightly bigger action potential (due to shorter inactivation time).

TABLE 1

Comparison of the basic electrophysiological properties of the pyramidal cells of the hippocampal CA1 region of control and neurotrypsin-overexpressing (DTG) mice

|  | Control | DTG | P |
| --- | --- | --- | --- |
| AP height [mV] | 105 ± 2 | 110 ± 2 | 0.05 |
|  | (n = 21) | (n = 29) |  |
| AP half width [ms] | 1.0 ± 0.1 | 1.1 ± 0.1 | 0.5 |
|  | (n = 21) | (n = 29) |  |
| AP threshold voltage [mV] | −50 ± 1 | −50 ± 0.1 | 0.25 |
|  | (n = 21) | (n = 29) |  |
| AP threshold current [nA] | −0.40 ± 0.04 | −0.29 ± 0.02 | 0.005 |
|  | (n = 21) | (n = 29) |  |
| $R_i$ [MΩ] | 150 ± 11 | 147 ± 7 | 1.0 |
|  | (n = 20) | (n = 26) |  |
| $\tau_m$ | 24.2 ± 2.0 | 18.1 ± 1.4 | 0.0005 |
|  | (n = 20) | (n = 26) |  |
| $C_w$ [pF] | 176.1 ± 17.7 | 125.8 ± 9.5 | 0.0005 |
|  | (n = 20) | (n = 26) |  |
| $V_m$ [mV] | −69 ± 1 | −67 ± 1 | 0.75 |
|  | (n = 21) | (n = 29) |  |

Figure 26:
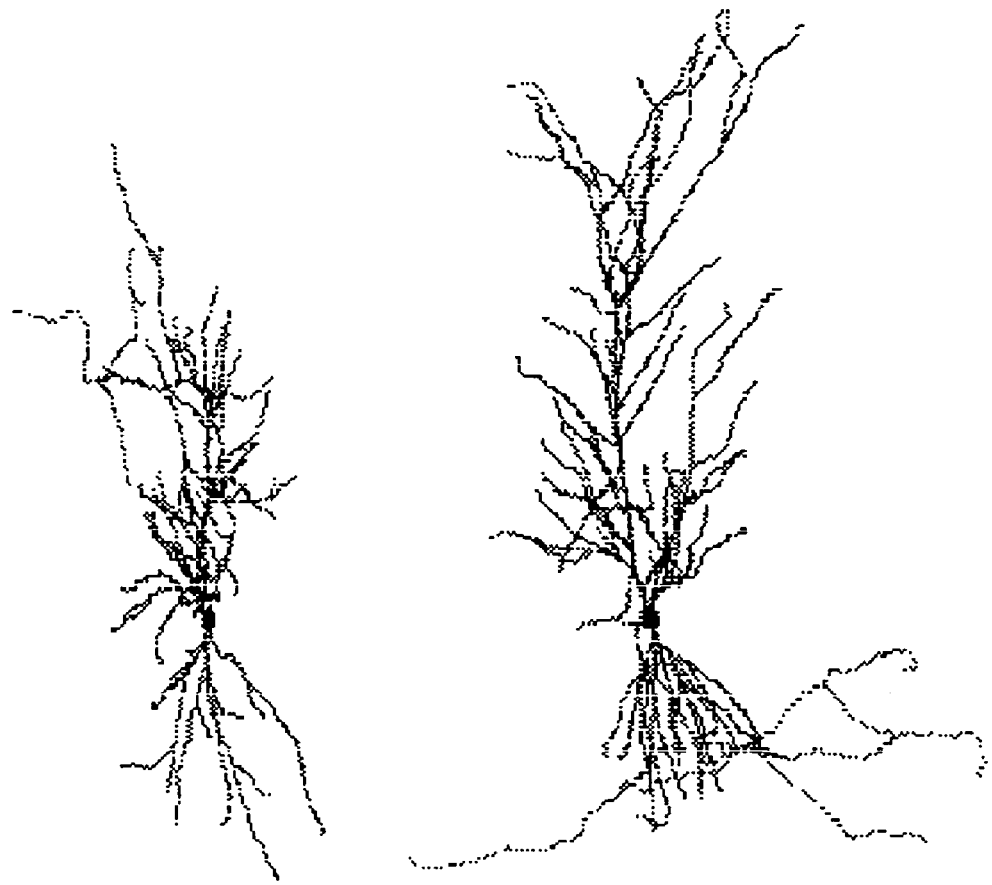
FIG. 26. Reconstructed CA1 pyramidal cells. The left cell is from a hippocampal slice of a wild-type mouse, the right from a hippocampal slice of a neurotrypsin-overexpressing (DTG) mouse. The cells shown were randomly selected; the differences between them do not indicate a size difference in the dendrites of neurons of neurotrypsin-overexpressing and wild-type mice (for quantitative data see FIG. 27). Scale bar, 100 μm.
Figure 27:
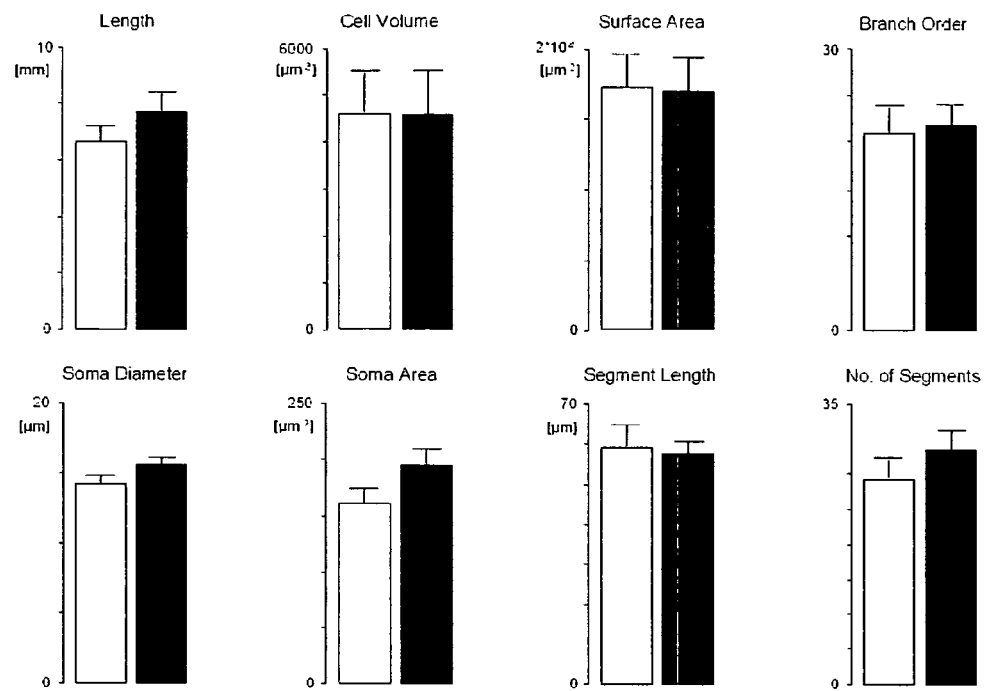
FIG. 27. Comparison of the spatial properties of reconstructed CA1 pyramidal cells. No significant difference was detected in any of the measurements. (White bars: control mice, n=8, black bars: neurotrypsin-overexpressing mice, n=11).

The membrane resting potential was measured at the patch pipette at the beginning of the next series of measurement. The membrane voltage response $\Box V_m$ to multiple current steps to the cells ranging from 0.01 nA to 0.05 nA in increments of 0.01 nA and 0.3 ms duration was measured and displayed with respect to time. One example of such a voltage trace is shown in FIG. 26. The following properties of the CA1 pyramidal cells were determined from those measurements: The membrane time constant $\tau_m$ was read at the 63% value of the maximum voltage change $\Delta V_m$. The input resistance $R_i$ was estimated by applying the Ohm's law. The resultant membrane voltage was displayed versus the input current and the $R_i$ calculated from the slope $\Delta V_m/\Delta I_i$ in the graph.

To investigate the charging characteristics of the cells, sub-threshold current injections were used to determine the apparent time constant ($\tau_m$) of these cells. An example of such a voltage deflection due to a hyperpolarizing current pulse of −30 pA is shown in FIG. 13 of a wild-type and a transgenic animal. The apparent time constant ($\tau_m = \Delta t$ at 63% $\Delta V_{max}$) is shorter in neurotrypsin-overexpressing animals than in wild-type littermates (18.1±1.4 versus 24.2±2.0 ms, respectively; p<0.0005). At the same time, $R_i$ was not different in both animal groups. Since $\tau_m$ is roughly the product of $C_m$ and $R_i$, and $R_i$ is not different in the two groups, we conclude that $C_m$ must be the cause for the difference. Indeed, the value is 176±18 versus 126±10 pF at a level of significance of p<0.0005. This value supports the above-mentioned increase in action potential height and indicates that the effective membrane area is smaller in neurotrypsin-overexpressing than in wild-type mice.

A lack of significance of the voltage threshold indicates that, at large, the sodium current is the same for both groups. A reduced current threshold together with a slightly increased AP size might be part of the change in excitability observed as reverberating activity. The underlying mechanism is due to a reduced cell surface. It was the aim of the work presented in the next sections (Examples 12 and 13) to get insight into where the surface area in transgenic animals is reduced.

Example 13

Increased Neurotrypsin in CNS Neurons Does Not Result in Reduced Number of Dendritic Arborizations (Results Obtained by Quantitative Morphology)

To determine the morphological correlate of the reduced cellular surface area indicated by a reduced $C_m$, the neurons used for whole-cell recordings were filled with biocytin and stained using the avidin-biotin-peroxidase reaction. After recording, each slice was flattened between two pieces of Millipore filter paper and fixed for 2-3 hours at room temperature in 1% glutaraldehyde, 2% paraformaldehyde and 0.2% picric acid in 0.1 M phosphate buffer (PB), pH 7.4. After fixation, the slice was stored in 0.5% paraformaldehyde in PB at 4° C.

The histological procedure used is similar to the one described earlier (Horikawa, K & Armstrong, W. E., *J. Neurosci. Methods* 25: 1-11, 1988; Kawaguchi, Y. et al., *J. Neurophysiol.* 62: 1052-1068, 1989). After several washes in PB, the slices were treated with 2% $H_2O_2$ for 15 min. The slices were then pre-incubated in 20% normal goat serum in 0.05 M Tris buffered saline (pH 7.4) containing 0.5% Triton X-100 (TBST) for 30 min at room temperature and subjected to overnight incubation in Vectastain Elite ABC (avidin-biotin-peroxidase) reagent (1:100; Vector Labs, Geneva, Switzerland) in TBST at 4° C. Following five 15 min washes in TBST and Tris buffer (TB, pH 7.6), biocytin containing cells were visualized by incubation in 3,3'-diaminobenzidine (0.05% in TB) in the presence of 0.0048% $H_2O_2$. The reaction was stopped by several washes in TB. Sections were mounted on slides and coverslipped in Moviol (Hoechst, Frankfurt, Germany).

The neurons were reconstructed three-dimensionally using a Neuron Tracing System (NTS), version 5.1 (Eutectic Electronics Inc., Jersey Court, USA). The neurons in the processed slices were tracked with a microscope (Optiphot-2, Nikon, Tokyo 100, Japan) using a 100×oil immersion objective by entering the 3D coordinates of the stage (NTS Mark 4 Stage) and the diameter measured at this point directly to a PC. The stage and the focus of the system were driven by stepper motors, where the minimum step size for the stage was 0.1 µm and for the focus 1 µm. The minimum diameter adjustable was 0.1 µm. Not considered were the dendritic spines and local swellings in the axons.

Figure 14:
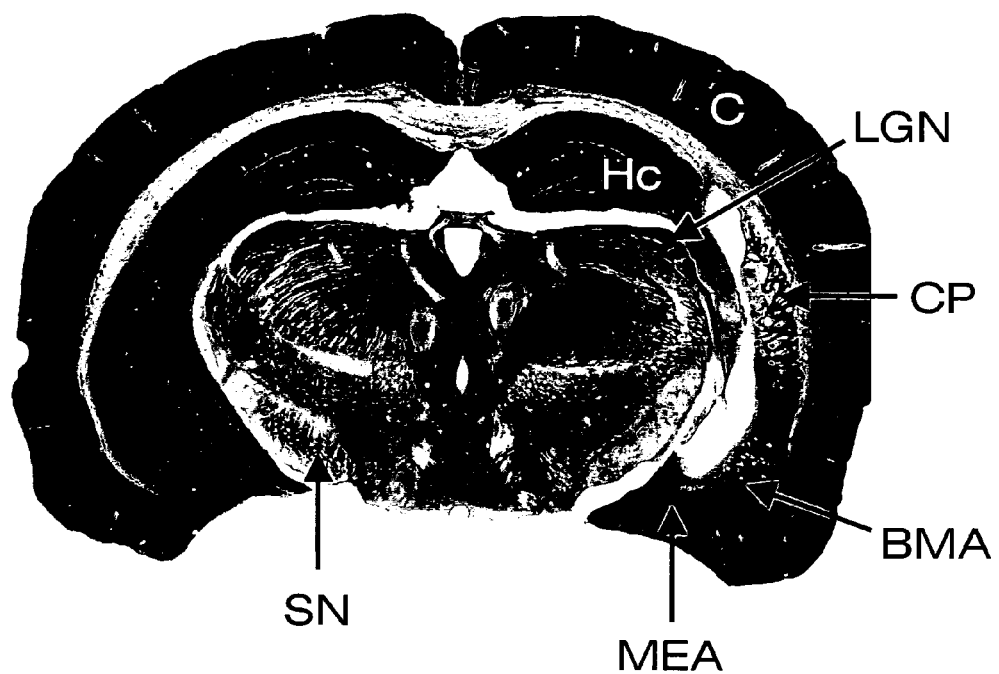
FIG. 14. The localization of neurotrypsin protein in the brain of an adult mouse is shown in a coronal section by immunolabeling with a specific, affinity-purified antibody against neurotrypsin and a peroxidase-conjugated secondary antibody. A strong immunoreactivity is visible in the gray matter. Particularly strong neurotrypsin immunoreactivity can be seen in the cerebral cortex (C), and the hippocampus (Hc). However, many other regions of the brain exhibit neurotrypsin immunoreactivity. Moderate neurotrypsin immunoreactivity is found in the lateral geniculate nucleus (LGN). High neurotrypsin immunoreactivity is found in the medial (MEA) and basomedial (BMA) nuclei of the amygdala, in the caudate putamen (CP), and in the substantia nigra (SN). No staining for neurotrypsin was detected in the white matter.
Figure 15:
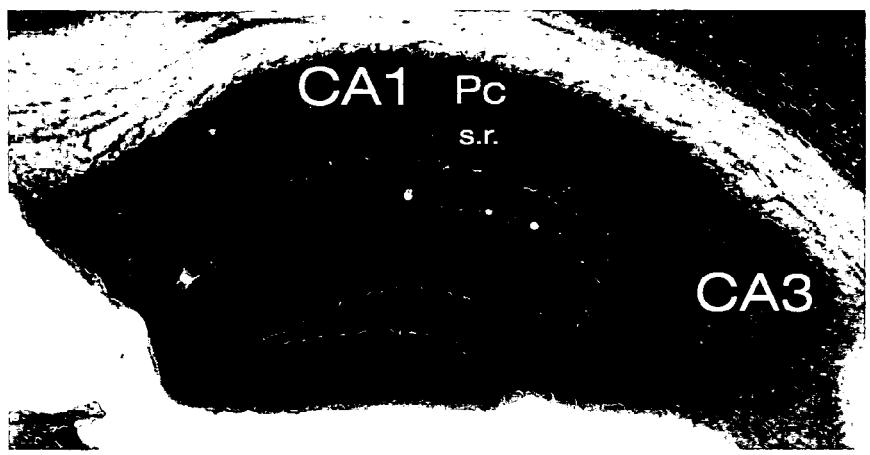
FIG. 15. The localization of neurotrypsin protein is demonstrated in the hippocampus of an adult mouse. (A) Neurotrypsin was visualized in a coronal section of the hippocampus by immunolabeling with a specific, affinity-purified antibody against neurotrypsin and a peroxidase-conjugated secondary antibody. A strong immunoreactivity was found in the synaptic layers. (B) A higher magnification view at the stratum radiatum (s.r. in panel A) of the hippocampus is shown. The pyramidal cells of the CA1 region are marked (Pc), in order to allow the identification of the location of the investigated tissue. Neurotrypsin immunoreactivity can be seen distributed in small discrete spots. The strong punctuate immunolabeling of the neuropil is typical for a protein with a synaptic localization. The neuronal somata of the pyramidal cells (Pc) of the CA1 region were unlabeled.
Figure 15:
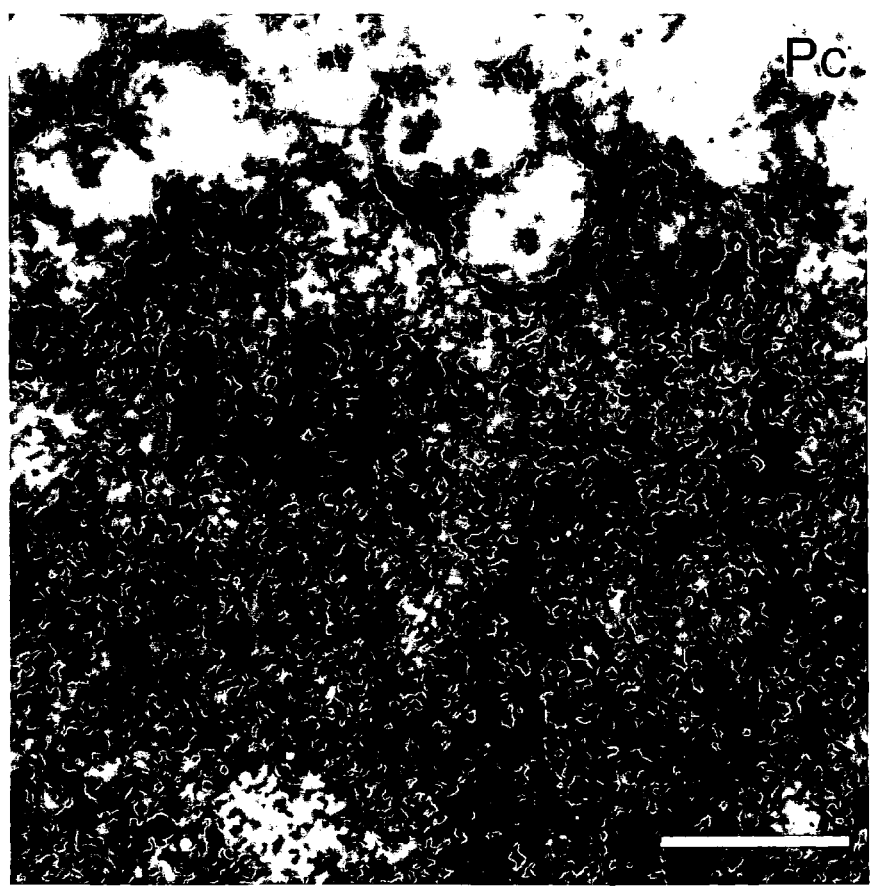

The statistical parameters of a cell were computed from the spatial data by using the NTS software. The estimated error of a single point was ±2 µm with a bigger error in the focusing axis. Two examples are shown in FIG. 14. They have been randomly chosen and differences between them are not representative for the average data. The scale bar represents 100 µm.

The reconstructions were used to calculate the total dendritic length, total cell volume, total membrane surface area, maximal branching order, mean dendritic segment length, average number of dendritic segments per cell, mean soma area and average soma diameter. The total dendritic length corresponds to the length of all dendritic segments with their branches. The total cell volume and the total membrane surface area are the sum of the volumes and membrane areas of the soma and the dendritic trees without spines. A dendritic segment was defined as the section of a dendrite between its base at the soma and the first branching point, the section between two branching points or the section between the last branching point and the end of the dendrite. The soma area was estimated from the outline marking the soma.

The results are based on reconstructions of neurons of 11 neurotrypsin-overexpressing and eight wildtype mice. The means of the two groups were calculated together with the standard errors of the mean and displayed in FIG. 15. The data illustrated revealed no significant differences between the control and the neurotrypsin-overexpressing group in spatial parameters (t-test) except for soma diameter and area, which were slightly bigger in the neurotrypsin-overexpressing mice.

These results indicate that there is no systematic difference between transgenic and wildtype animals if spines are not taken into account. This points towards a scenario, where the loss of membrane area is confined to dendritic spines, since a very substantial proportion of the dendritic surface area is due to the spines (Cauller L. and Connors, B. W., Functions of very distal dendrites: Experimental and computational studies of layer I synapses on neocortical pyramidal cells. In *Single neuron computation*. ed. McKenna, T., Davis, J. & Zornetzer, S. F., pp. 199-229. Academic Press, Inc., San Diego, Calif. 92101). In fact, the slightly larger somatic diameter and surface area should have resulted in a bigger $C_m$, which we did not see, indicating that, indeed, most of the surface lost is within the spines. Since the measurements of $C_m$ and the reconstructions were from the same cells, we are confident that the estimates of surface area are not compromised by slicing artifacts. Since the spines are the loci where synapses form, and since these seem to be reduced in size and/or number, the effect of neurotrypsin is indeed at the synapse, resulting in this case in (partial) removal of the postsynaptic part of the synapse.

Example 14

Increased Levels of Neurotrypsin in CNS Neurons Result in Reduced Number and Size of Synapses (Results Revealed by Quantitative Morphology)

In this experiment, we attempted to quantify the number of synapses per volume of tissue of a synapse-rich region, and to measure the size parameters of the synapses. Parameters measured included the area of the presynaptic axon terminals, the area of the postsynaptic spines, and the length of the synapses (as measured by the length of the apposition of the pre- and postsynaptic membrane). Two independent lines of neurotrypsin-overexpressing mice (Nt491/cre and Nt494/cre) and several lines of control mice (wildtype mice, CMV-Cre mice, and the transgenic parental lines bearing the inactive neurotrypsin transgene (Nt491-inact.Nt and Nt494-inact.Nt) were investigated.

Figure 29:
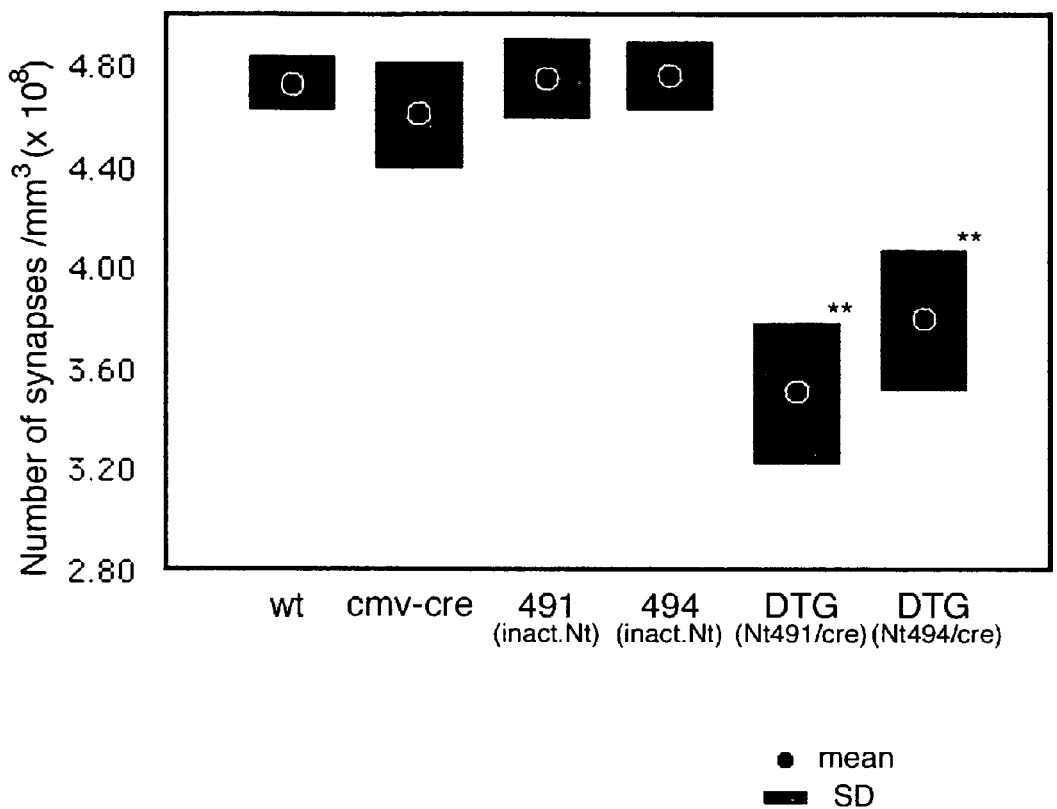
FIG. 29. Quantification of the number of synapses per volume of tissue in the neuropil of the stratum radiatum of the CA1 region of the hippocampus. In all experimental animals, the number of synapses per volume of tissue was determined from electron microscopic sections taken from the same location in the stratum radiatum of the CA1 region of the hippocampus wt: wild type; CMV-Cre: transgenic line expressing the Cre recombinase under the control of the CMV promoter; 491 (inact.Nt): transgenic line 491, bearing the inactive transgene, containing a transcriptional stop segment; 494(inact.Nt): transgenic line 494, bearing the inactive transgene, containing a transcriptional stop segment; DTG(Nt491/cre): double transgenic mouse descending from the line 491, in which the inactive neurotrypsin transgene has been activated by crossing in the Cre recombinase; DTG(Nt494/cre): double transgenic mouse descending from the line 494, in which the inactive neurotrypsin transgene has been activated by crossing in the Cre recombinase. (**, $p<0.01$).

The mice were deeply anesthetized at the age of 28 days with metofane (Schering-Plough, USA) and perfused through the heart with 0.9% sodium chloride followed by fixative consisting of 2% paraformaldehyde, and 1% glutaraldehyde in 0.1 M phosphate buffer pH 7.4 (PB). The brains were removed from the skull and sectioned into 100 μm-thick serial sections with a vibratome. The sections were postfixed in 1% osmium tetroxide in PB, treated with 2% uranyl acetate, dehydrated in ethanol and propylene oxide and embedded in Durcupan ACM resin (Fluka). For electron microscopic analysis strips of sections containing the CA1 region of the hippocampus at the anteriocaudal level Bregma −2 mm and mediolaterally 1.5 mm were ultrasectioned. An illustration of the EM images obtained is given in FIG. 29.

The synaptic sampling procedure consisted of 15 to 23 EM samples of the neuropil of the stratum radiatum of the hippocampal CA1 region from three noncontiguous areas with at least 50 μm distance between each other an initial magnification of 27,500-fold. The electron micrographs were printed at a final magnification of 80,000-fold which represented 90 to 135 μm$^2$ of tissue. A synapse was defined as two apposed thickened membranes of a presynaptic and postsynaptic profile, with the presynaptic profile containing at least three synaptic vesicles in close association with the differentiated membranes. The synapses were classified into axodendritic and axospinous synapses according to ultrastructural criteria. Dendritic shafts were identified by their size and the presence of mitochondria and microtubules. Dendritic spines were of smaller diameter, lacked mitochondria and microtubules, and occasionally contained a spine apparatus. The axodendritic synapses comprised an insignificantly small proportion in all samples and therefore were excluded from further statistical estimation. All axospinous synapses were counted in each micrograph with exception of those touching the exclusion lines (an unbiased counting frame, Gundersen, H. J. G., *J. Microsc.* 111: 219-223,1977). The cross-section areas of axonal terminals and postsynaptic spines and lengths of synaptic junctions of all axospinous synapses were measured directly from the prints using a magnetic tablet (Kurta) and the Macstereology 2.8 (Ranfurly Microsystems, UK) analysis program. The numerical density of synapses were obtained using size-frequency method and formula $N_V = N_A/d$ (were $N_A$ is a number of synaptic profiles per unit area and d is the average length of synaptic junctions; Colonnier, M. and Beaulieu, C., *J. Comp. Neurol.* 231: 175-179,1985; DeFelipe, J., et al., *Cereb. Cortex* 9:722-732, 1999).

Figure 30:
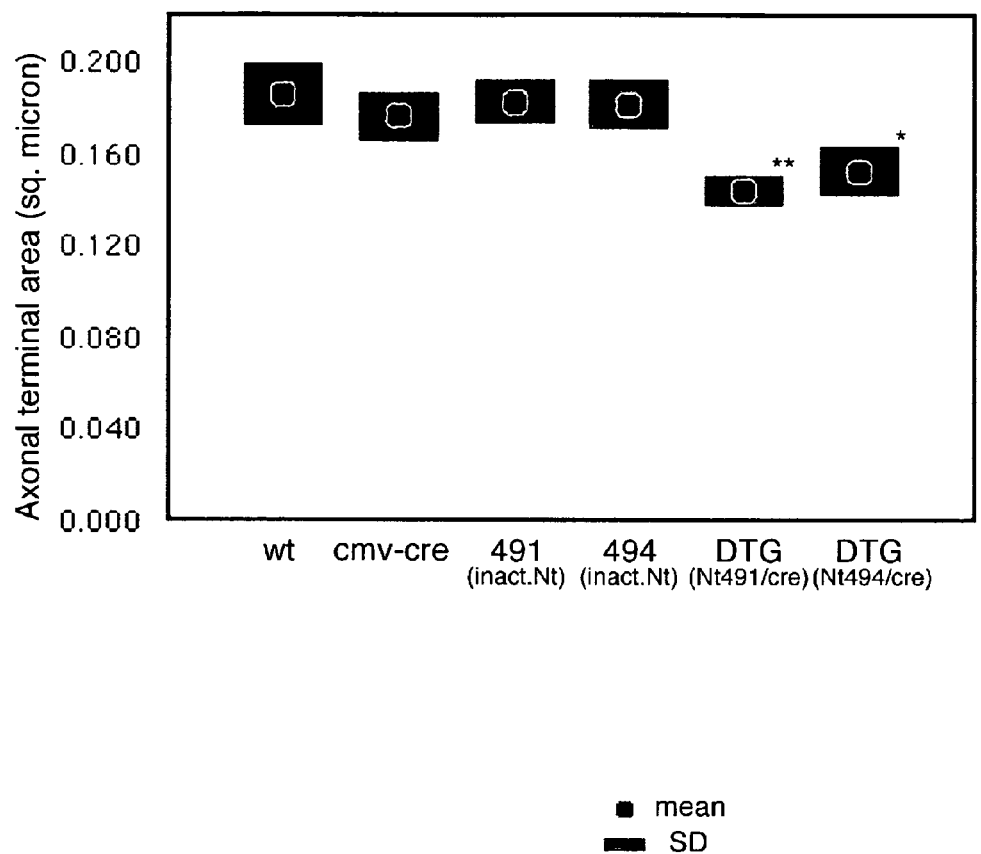
FIG. 30. Quantification of the axon terminal area in the neuropil of the stratum radiatum of the CA1 region of the hippocampus. In all experimental animals, the axon terminal area of axons that form asymmetric synapses was determined from electron microscopic sections taken from the same location in the stratum radiatum of the CA1 region of the hippocampus wt: wild type; CMV-Cre: transgenic line expressing the Cre recombinase under the control of the CMV promoter; 491(inact.Nt): transgenic line 491, bearing the inactive transgene, containing a transcriptional stop segment; 494(inact.Nt): transgenic line 494, bearing the inactive transgene, containing a transcriptional stop segment; DTG(Nt491/cre): double transgenic mouse descending from the line 491, in which the inactive neurotrypsin transgene has been activated by crossing in the Cre recombinase; DTG(Nt494/cre): double transgenic mouse descending from the line 494, in which the inactive neurotrypsin transgene has been activated by crossing in the Cre recombinase. (*, $p<0.05$; **, $p<0.01$).

The number of synapses per cubic mm (mm$^3$) was significantly reduced in neurotrypsin-overexpressing mice (FIG. 30). In contrast, the numbers of synapses in control mice, i.e., the parental lines used for the generation of the double transgenic (DTG) neurotrypsin-overexpressing mice (491-inact.Nt, 494-inact.Nt, and CMV-Cre) were the same as in wild-type mice. Therefore, these results indicate a significant reduction of synapses in the neurotrypsin-overexpressing mice.

Figure 31:
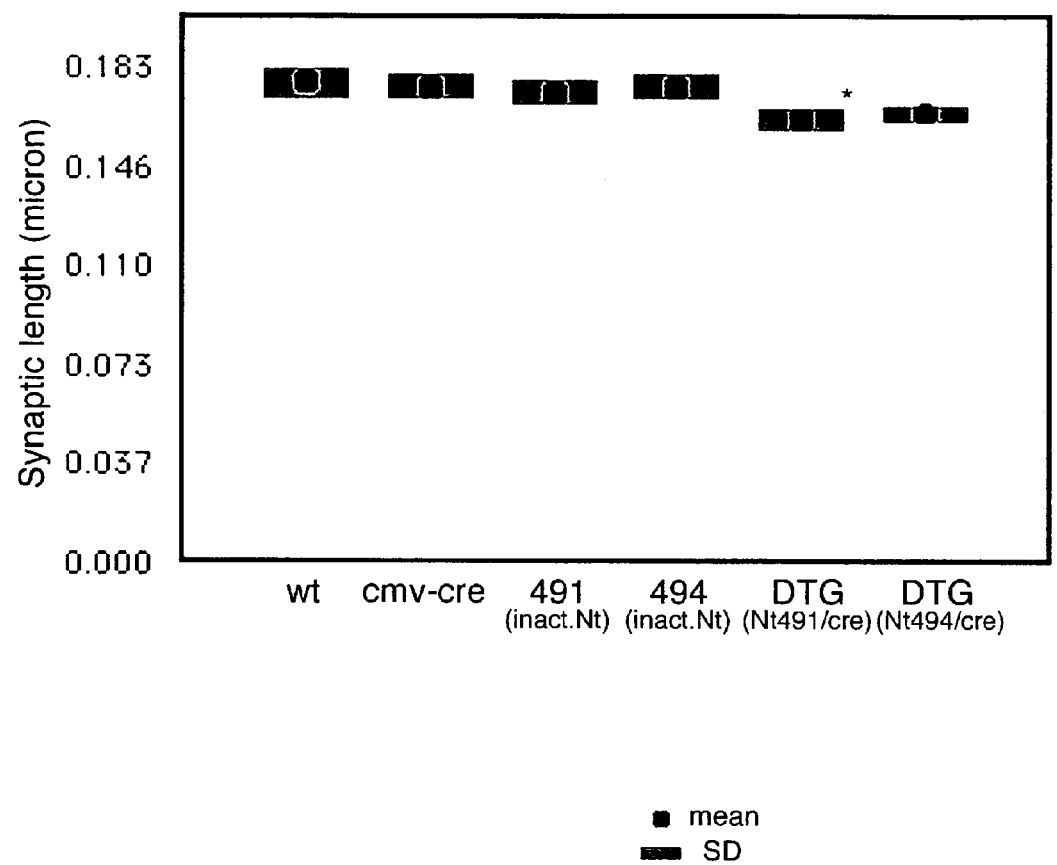
FIG. 31. Quantification of the synaptic lengths of axospinous synapses in the neuropil of the stratum radiatum of the CA1 region of the hippocampus. In all experimental animals, the number of synapses per volume of tissue was determined from electron microscopic sections taken from the same location in the stratum radiatum of the CA1 region of the hippocampus. As a measure of the synaptic length, the length of the parallel alignment of the presynaptic and the postsynaptic membrane enclosing the synaptic cleft was measured wt: wild type; CMV-Cre: transgenic line expressing the Cre recombinase under the control of the CMV promoter; 491 (inact. Nt): transgenic line 491, bearing the inactive transgene, containing a transcriptional stop segment; 494(inact.Nt): transgenic line 494, bearing the inactive transgene, containing a transcriptional stop segment; DTG(Nt491/cre): double transgenic mouse descending from the line 491, in which the inactive neurotrypsin transgene has been activated by crossing in the Cre recombinase; DTG(Nt494/cre): double transgenic mouse descending from the line 494, in which the inactive neurotrypsin transgene has been activated by crossing in the Cre recombinase. (*, $p<0.05$).

Axonal terminal area was significantly reduced in neurotrypsin-overexpressing mice (FIG. 31). In contrast, the values in control mice, i.e., the parental lines used for the generation of the double transgenic (DTG) neurotrypsin-overexpressing mice (491-inact.Nt, 494-inact.Nt, and CMV-Cre) were the same as in wild-type mice. Therefore, these results indicate a significant reduction of the presynaptic terminal size in the neurotrypsin-overexpressing mice.

Figure 32:
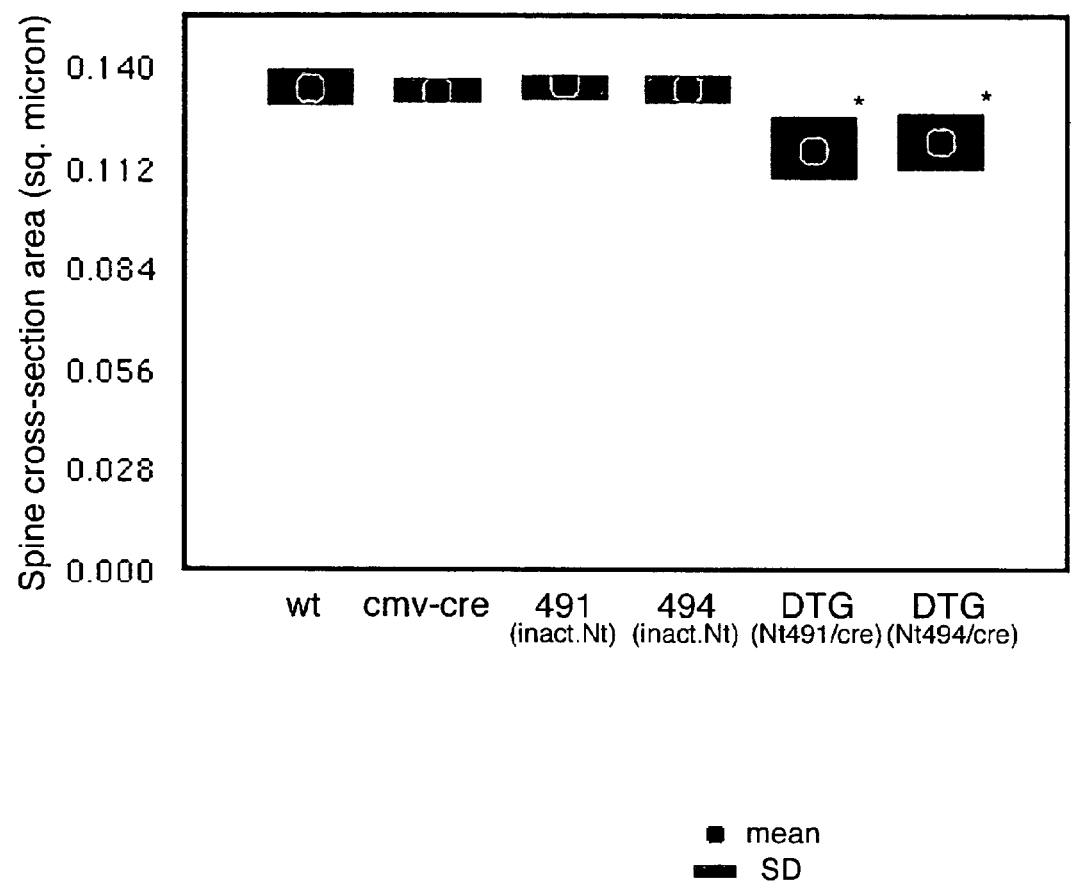
FIG. 32. Quantification of the cross-sectional area of dendritic spines in the neuropil of the stratum radiatum of the CA1 region of the hippocampus. In all experimental animals, the postsynaptic dendritic spines that form synapses were determined from electron microscopic sections taken from the same location in the stratum radiatum of the CA1 region of the hippocampus wt: wild type; CMV-Cre: transgenic line expressing the Cre recombinase under the control of the CMV promoter; 491(inact.Nt): transgenic line 491, bearing the inactive transgene, containing a transcriptional stop segment; 494(inact.Nt): transgenic line 494, bearing the inactive transgene, containing a transcriptional stop segment; DTG(Nt491/cre): double transgenic mouse descending from the line 491, in which the inactive neurotrypsin transgene has been activated by crossing in the Cre recombinase; DTG(Nt494/cre): double transgenic mouse descending from the line 494, in which the inactive neurotrypsin transgene has been activated by crossing in the Cre recombinase. (*, $p<0.05$).

Synaptic length was significantly reduced in neurotrypsin-overexpressing mice (FIG. 32). In contrast, the values in control mice (i.e., the parental lines used for the generation of the double transgenic (DTG) neurotrypsin-overexpressing mice (491-inact.Nt, 494-inact-Nt, and CMV-Cre)) were the same as in wild-type mice. Therefore, these results indicate a significant reduction of the synaptic area in the neurotrypsin-overexpressing mice.

Figure 33:
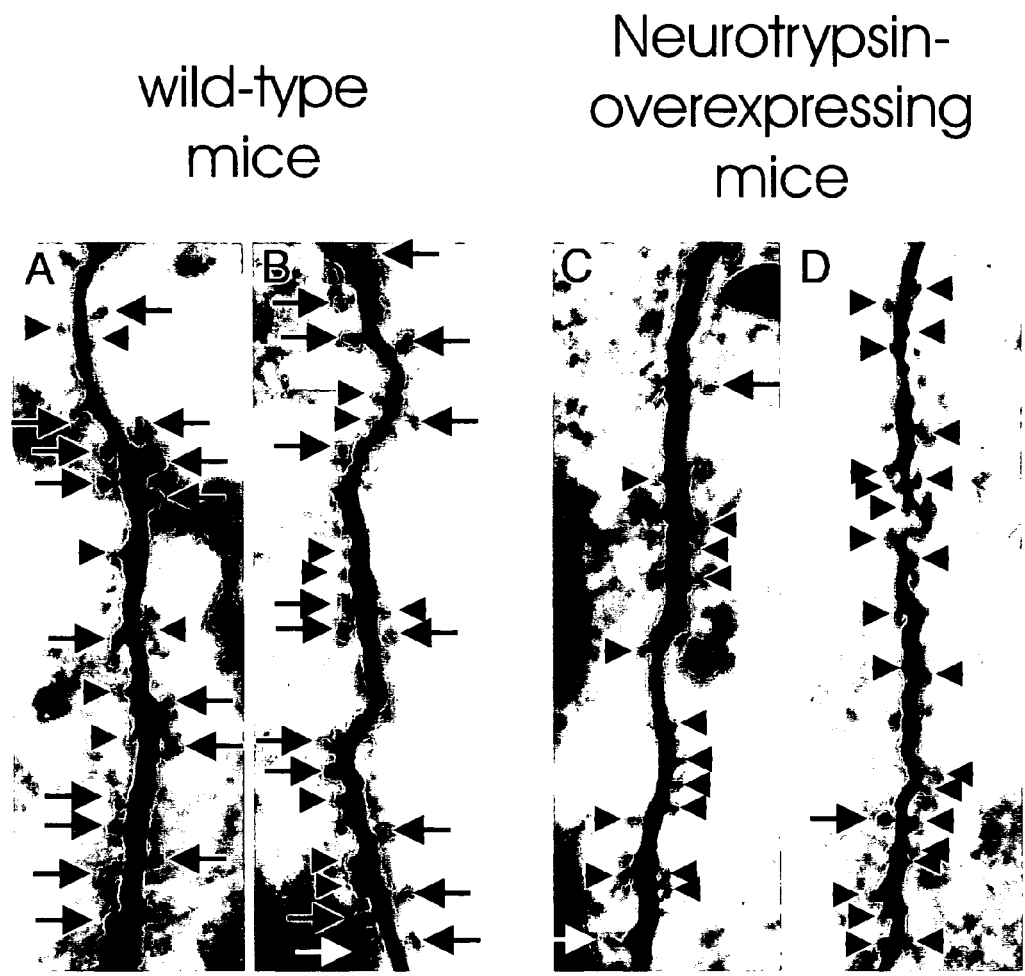
FIG. 33. Spines on secondary dendritic branches of CA1 pyramidal neurons of wild-type mice (A and B) and double-transgenic mice overexpressing neurotrypsin (C and D). CA1 pyramidal cells were iontophoretically filled with biocytin during electrophysiological in vitro studies and visualized using avidin-biotin-peroxidase histochemistry. Dendrites of wild-type mice have many long, well-developed spines (large arrows); in addition, many short, stubby-shape spines (small arrowheads) are also found. Dendrites of neurotrypsin-overexpressing mice (littermates) are dominated by short stubby-shape spines (small arrowheads); long, well-developed spines (large arrows) are very rare. Note, also, that the total spine density (number of spines per unit length of dendrite) is markedly lower in neurotrypsin-overexpressing mice (C and D).
Figure 34:
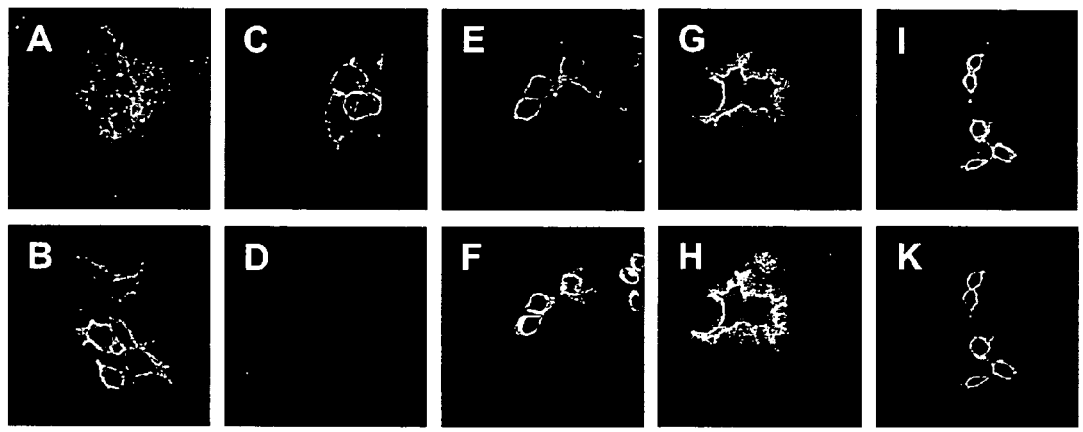
FIG. 34. Immunofluorescent detection of agrin and neurotrypsin in transiently transfected HEK293T cells. Semi-confluent HEK293T cells on glass coverslips in 3 ml DMEM/10% FCS in a 3 cm well were transiently transfected with 5 µg of either pcDNA3.1-neurotrypsin, or pcDNA3.1-agrin, or both, respectively, using Ca-phosphate precipitation. 48 hrs after transfection the cells were washed, fixed with 4% paraformaldehyde and processed for indirect immunofluorescence with rabbit polyclonal anti-neurotrypsin antiserum (SZ177, 1:300; Texas red-conjugated secondary anti-rabbit IgG antibody; A,C,E,G,I) and monoclonal anti-agrin antibody (AGR540, Stressgen, 1:600; FITC-conjugated secondary anti-mouse IgG antibody; B,D,F,H,K). Single transfections of non-permeabilized cells are shown in (A,B). Double transfections of non-permeabilized cells are shown in (C,D). Cell surface agrin immunoreactivity is absent in the presence of neurotrypsin (D). Double transfections of permeabilized cells are shown in (E,F). Agrin immunoreactivity is present intracellularly (F). Double transfections with catalytically inactive neurotrypsin and agrin are shown with non-permeabilized (G,H) and permeabilized cells (I,K). Agrin immunoreactivity remains at the cell surface in the presence of catalytically inactive neurotrypsin (H). Note the clear membrane accumulation of neurotrypsin in the presence of agrin (C,E,G,I), but not in the absence (A). Digital images were taken on a Leica microscope at 630× magnification and processed with Adobe Photoshop and Microsoft PowerPoint.

The cross sectional area of the postsynaptic spines was significantly reduced in neurotrypsin-overexpressing mice (FIG. 33). In contrast, the values in control mice, i.e. the parental lines used for the generation of the double transgenic (DTG) neurotrypsin-overexpressing mice (491-inact.Nt, 494-inact-Nt, and CMV-Cre) were the same as in wild-type mice. Therefore, these results indicate a significant size reduction of the postsynaptic spines in the neurotrypsin-overexpressing mice.

In summary, the synapse density, as determined by the number of synapses per mm$^3$, is significantly reduced in the neurotrypsin-overexpressing mice as compared with wild-type and control littermates (FIG. 30). The presynaptic terminals are reduced in size (FIG. 31). The synaptic length, as determined by the length of the apposition of the pre- and postsynaptic membrane, is significantly reduced in neurotrypsin-overexpressing mice (FIG. 32). Similarly, the size of the postsynaptic spines is significantly reduced in neurotrypsin-overexpressing mice (FIG. 33).

In transgenic mice overexpressing the catalytically inactive mutation of neurotrypsin, engineered by mutating the reactive site serine 711 to an alanine (Ser711Ala mutation), these synaptic alterations were not found. In conclusion, the observations made in transgenic mice overexpressing the wild-type form of neurotrypsin are mediated by the proteolytic activity of neurotrypsin.

Example 15

Neurotrypsin Functions as a Modulator of a Synaptic Protein: Neurotrypsin Mediates the Cleavage of the Central Nervous System Form of Agrin In search for the proteolytic target proteins of neurotrypsin, we focused on extracellular proteins of the synaptic cleft or membrane proteins of the pre- and post-synaptic membranes. Because of the numerous parallels between CNS synapses and the neuromuscular junction, proteins thought to occur at both were included in the group of candidates, even if their characterization has been worked out exclusively or predominantly at the neuromuscular junction. Among the many candidates two are of primary relevance: Agrin and MuSK.

Agrin is a well-characterized synaptic organizer molecule of the neuromuscular junction (Sanes, J. R. and Lichtman, J., *Nat. Rev. Neurosci.* 2: 791-805, 2001). It has a core protein mass of 210 kDa. Recently, the expression of agrin in the brain and its role in synaptic development, structure and function has received considerable attention (Smith, M. A. and Hilgenberg, L. G., *Neuroreport* 13: 1485-1495, 2002; Kroger, S. and Schroder, J. E., *News Physiol. Sci.* 17: 207-212, 2002). Agrin exists in several isoforms. Most of these isoforms are extracellular matrix proteins, but there are also type II transmembrane forms that carry a very short N-terminal cytoplasmic segment. MuSK is a muscle-specific tyrosine kinase which functions as a putative receptor of agrin. The functional importance of agrin and MuSK is documented by the finding that knockout mice for either of these genes died around birth. Embryonic analysis of neuromuscular development revealed severe defects in the formation of neuromuscular junctions (Gautam, M. et al., Cell 85: 525-535,1996; DeChiara, T. M. et al., Cell 85: 501-512,1996). Recent studies in our laboratory led to the observation that neuromuscular junctions fail to form properly in neurotrypsin-overexpressing mice. Consequently, we hypothesized that a putative substrate of neurotrypsin should be detectable among the molecules present in the synaptic cleft or the surface membranes of the neuromuscular junction.

To test whether agrin is a substrate of neurotrypsin we developed a cotransfection assay with HEK293T cells. For this purpose, a 2310 bp KpnI-HindIII fragment just encompassing mouse neurotrypsin coding sequences was cloned into the eucaryotic expression vector pcDNA3.1(−) (Invitrogen) via KpnI and HindIII. A cDNA clone coding for rat agrin (the transmembrane isoform Y4, Z8) was obtained from Dr. K. Tsim (University of Hong Kong). In this clone, rat agrin is inserted into the polylinker of pcDNA3 (Invitrogen) via KpnI and EcoRI.

HEK293T cells were cultured in DMEM/10% FCS at 37° C. in humidified air with 10% $CO_2$. For transfection, cells were seeded in 3 ml DMEM/10% FCS onto glass cover slips placed into a 3 cm dish. The day after seeding, at a confluence of 40-60%, the cells were transiently transfected with cDNAs encoding neurotrypsin and agrin (5 □g DNA each) using calcium-phosphate precipitation. Four hours after transfections, the medium was carefully removed and replaced by 3 ml fresh DMEM/10% FCS. Cells were further incubated for 48 hrs.

Immunofluorescence was used to investigate the impact of neurotrypsin on agrin distribution. Forty-eight hrs after transfection, the cells were fixed with 4% paraformaldehyde in PBS for 10 min. Excess of the fixative was removed by washing and quenching in PBS/glycine. After blocking with horse serum the cells were incubated with the primary antibodies (SZ177, rabbit anti-neurotrypsin antibody, 1:300; AGR540 (Stressgen), a mouse anti-agrin antibody, 1:600) for 45 min, washed with PBS, incubated with secondary Texas red-coupled anti-rabbit IgG and FITC-coupled anti-mouse IgG, respectively for 45 min, washed, and mounted onto glass slides with fluorescent mounting medium (DAKO).

Figure 35:
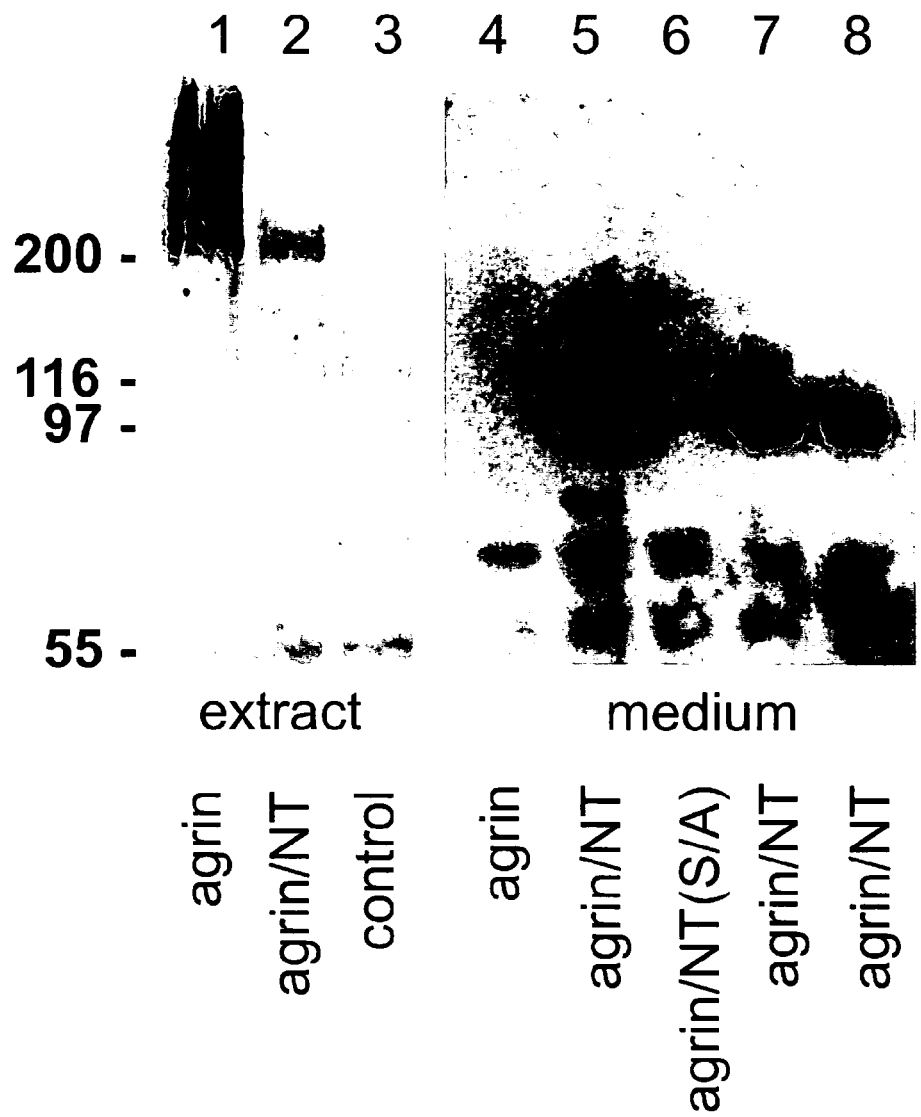
FIG. 35. Western blot analysis of agrin from transiently transfected HEK293 cells. Semi-confluent HEK293T cells in 2 ml DMEM/10% FCS in a 3 cm well were transiently transfected with 5 µg of either pcDNA3.1-neurotrypsin, or pcDNA3.1-agrin, or both, respectively, using Ca-phosphate precipitation. 48 hrs after transfection the medium was removed, proteins were precipitated and redissolved in Laemmli loading buffer. The cells were washed with PBS. A 1% Triton X-100 detergent extract was prepared. Samples from the extract (301 g, equivalent to ⅛ of totally extracted protein) and concentrated media were separated by SDS-PAGE and transferred to nitrocellulose. Cell extracts of agrin- (lane 1), agrin plus neurotrypsin- (lane 2), and control-transfected (lane 3) assays were probed with the polyclonal anti-agrin antibody K-17 (Santa Cruz; 1:1,000). 200 µl medium from such an experiment, and additionally from a double transfection with agrin and catalytically inactive neurotrypsin (NT(S/A)), were tested with the monoclonal anti-agrin antibody AGR540 (Stressgen; 1:1,000; lanes 4-6). In lanes 7 and 8, 100 µl and 50 µl of medium from an agrin/neurotrypsin double transfection were loaded, respectively. For detection of the primary antibodies, HRP-coupled secondary antibodies were used. HRP activity was visualized by chemiluminescence. A soluble 100-kDa agrin fragment is produced in the presence of neurotrypsin. Positions of molecular mass markers are indicated at the left margin (in kDa).

Single cDNA transfection resulted in neurotrypsin immunoreactivity diffusely arranged around the cell (FIG. 35A). Agrin immunofluorescence was found highly concentrated at the cell surface, as expected for an integral membrane protein (FIG. 35B). Analysis after double transfection showed a rather different situation: cell surface agrin immunoreactivity was absent in neurotrypsin-positive cells (FIG. 35, C and D). Intracellular agrin immunoreactivity, however, was still detectable in neurotrypsin-positive cells (FIG. 35, E and F).

We repeated the assay using the cDNA coding for catalytically inactive neurotrypsin (a mutant in which the active-site serine is replaced by alanine). Single transfection showed that catalytically inactive neurotrypsin was produced and subcellularly distributed in a manner indistinguishable from wild-type neurotrypsin (not shown). In contrast to active neurotrypsin, however, double transfection with agrin and inactive neurotrypsin did not result in the disappearance of agrin from the cell surface (FIG. 35, G-K).

Immunodetection of agrin in transfected HEK293T cells was done with two different anti-agrin antibodies with virtually identical results. Both antibodies recognize an epitope located in the extracellular C-terminal third of the protein. Thus, neurotrypsin-mediated cleavage must occur N-terminally to these epitopes to release a C-terminal portion of agrin. Additionally, in neurotrypsin transfectants, immunoreactivity was only loosely associated with the cell periphery (FIG. 35A). In the presence of agrin, however, neurotrypsin (both active and inactive form) was clearly enriched at the plasma membrane (FIG. 35, C,E,G,I).

From this finding, we conclude that the disappearance of cell surface agrin is caused by neurotrypsin-mediated proteolysis within the extracellular domain of agrin. The redistribution of neurotrypsin in the presence of overexpressed agrin furthermore suggests that agrin influences neurotrypsin targeting, possibly by acting as a direct or indirect binding partner at the cell surface or by acting as a carrier for neurotrypsin secretion.

We then performed Western blot analysis to follow the fate of agrin biochemically. For this purpose, HEK293T cells were directly seeded into 3 cm wells and cultured in 2 ml DMEM/10% FCS. Transfection was performed as described for immunofluorescence analysis. 48 hrs after transfection, the cells were washed with PBS. The cells were lysed by the addition of 250 µl buffer (20 mM Tris-HCl, pH 7.4, 150 mM NaCl, 1 mM EDTA, 1% Triton X-100, protease inhibitor cocktail). The extract was incubated at 4° C. for 20 min and then centrifuged for 20 min with 15000×g at 4°. The supernatant was saved. After determination of protein concentration, the supernatant was mixed with 5×Laemmli loading buffer, boiled for 3 min, centrifuged and used for analysis. Proteins were separated by SDS-PAGE, using 7.5% acrylamide. After electrophoresis, proteins were transferred to a nitrocellulose membrane. Transfer quality was verified by Ponceau S staining. The membrane was then blocked with TBS containing 0.1% Tween-20 and 5% (w/v) blocking reagent (Amersham). All subsequent steps were done in TBS with 0.1% Tween-20. The membrane was incubated with the primary antibody (SZ177, 1:1000; AGR540, 1:1000; K-17, a polyclonal anti-agrin antibody (Santa Cruz), 1:1000) for 60 min. After extensive washing, the membrane was incubated with secondary peroxidase-coupled antibodies for 45 min. Detection was done with ChemiGlow (Alpha Innotech) according to the manufacturer's instruction. Images were taken with a Chemilmager (Alpha Innotech).

Figure 23:
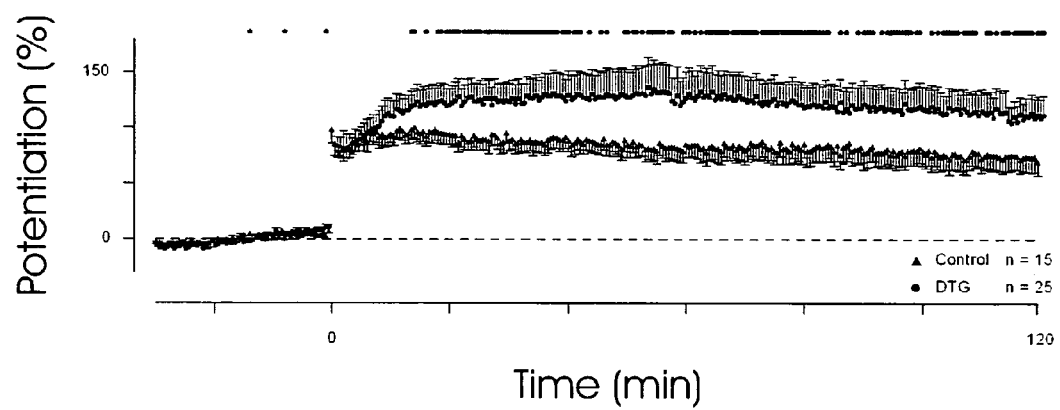
FIG. 23. Mean potentiation of the pooled and normalized fEPSP experiments concerning LTP. Each point represents the mean peak amplitude calculated from the pooled slopes of the fEPSP experiments. Compared are the results from animals belonging to the control and the neurotrypsin-overexpressing group (DTG). The fEPSP time courses are normalized to the mean of the base-line responses and expressed as percentage of potentiation. The dashed line represents potentiation of zero %. The error bars represent the standard deviation of this average. For clarity of presentation, error bars are shown in one direction only, pointing upwards for the group of neurotrypsin-overexpressing mice (DTG) and downwards for the control group (control). The dots above the graph indicate where the difference between the means of the two groups reaches significance ($p \leq 0.05$, determined by a paired Student t-test).
Figure 36:
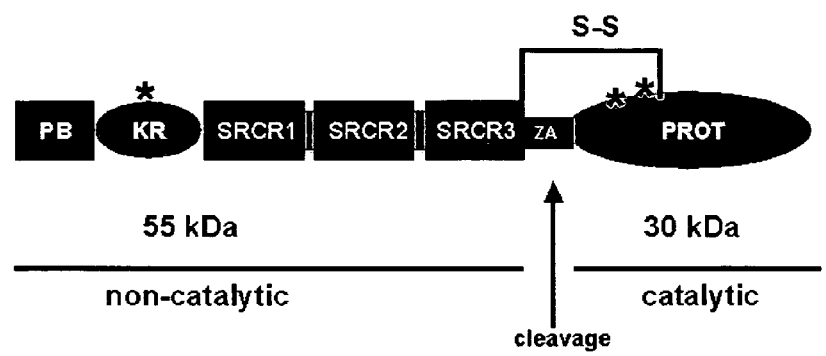
FIG. 36. Domain structure of neurotrypsin. (A) Neurotrypsin of the mouse. (B) Human Neurotrypsin. Human neurotrypsin is composed of a proline-rich basic domain (PB), a kringle domain, four scavenger receptor cysteine-rich domains (SRCR1, SRCR2, SRCR3, and SRCR4), and a protease domain (PROT). In neurotrypsin of the mouse, only 3 SRCR domains are found. The zymogen activation site (ZA) represents a potential cleavage site at the N-terminus of the protease domain of neurotrypsin. Proteolytic cleavage at the ZA site converts the neurotrypsin protein from a catalytically inactive to a catalytically active form. By this cleavage, a fragment of approximately 55 kDa, comprising the non-catalytic region, and a fragment of approximately 30 kDa, comprising the protease domain, are generated in the case of mouse neurotrypsin. In the case of human neurotrypsin, the fragments generated have 67 kDa and 30 kDa, respectively. The putative disulfide bond connecting the protease domain with the third SRCR domain is indicated (S—S). Asterisks indicate potential N-glycosylation sites.
Figure 36:
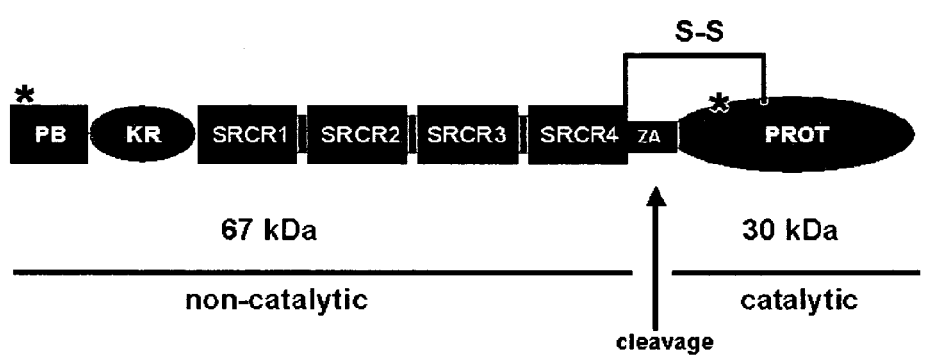

Agrin was clearly identified in detergent extracts of single transfectants (FIG. 36, lane 1). In extracts of double transfectants, agrin was strongly reduced (FIG. 36, lane 2). No agrin signal was found in cells transfected with empty vector (FIG. 23, lane 3). The production of neurotrypsin under all conditions was confirmed after reprobing the blot with anti-neurotrypsin antibodies (not shown). In 200 µl culture medium of double transfected HEK293T cells a 100 kDa signal was detected with the anti-agrin antibody (FIG. 36, lane 5). This signal was not found in medium from single transfectants (FIG. 36, lane 4). Likewise, no signal was detected in medium of HEK293T cells transfected with agrin and catalytically inactive neurotrypsin (FIG. 36, lane 6). Lanes 7 and 8 are as lane 5 with only 100 µl and 50 µl medium, respectively.

In summary, the results from the immunofluorescence and Western blot analysis indicate that:

1) neurotrypsin produced in HEK293T cells has catalytic activity;
2) agrin, an extracellularly-present component of the neuromuscular junction and the synapses of the central nervous system, can be cleaved by neurotrypsin-dependent proteolysis; and
3) this neurotrypsin-dependent cleavage leads to the formation of a truncated and a released form of agrin.

Because the released portion of agrin contains the domain bearing the synaptogenic site of agrin, these results indicate that the synaptic changes induced by the overexpression of neurotrypsin in neurons are due to the neurotrypsin-dependent proteolysis and indicate a regulatory role of neurotrypsin for synaptic structure and function.

Example 16

Production of Neurotrypsin

Figure 37:
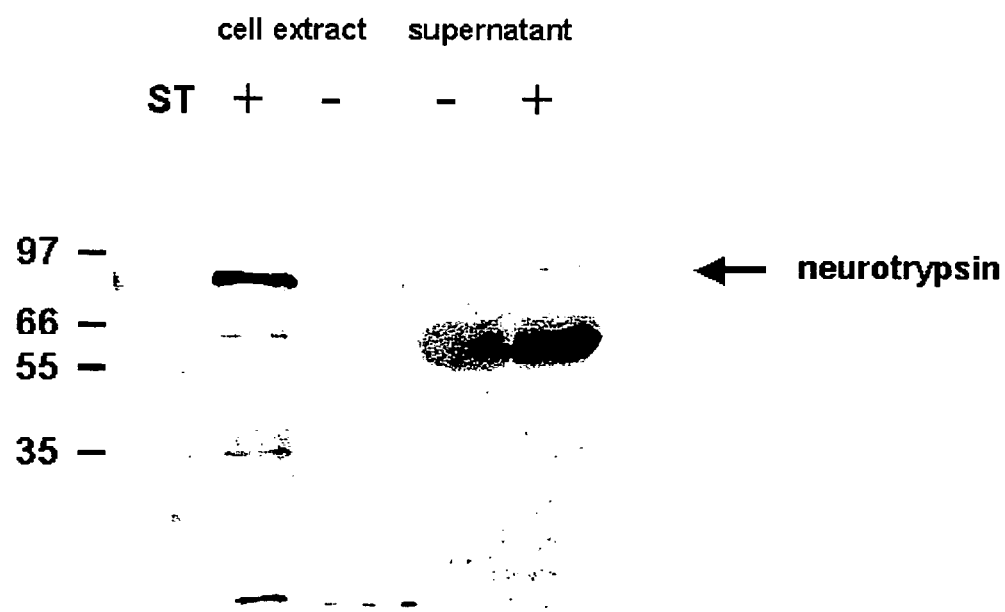
FIG. 37. Expression of recombinant neurotrypsin in HEK293T cells. Ten µg total protein of each fraction was separated on a 10% SDS PAGE and then transferred to a nitrocellulose membrane. Recombinant protein was detected with an anti-Tetra-His antibody (QIAGEN, dilution 1:2000) and a goat-anti-mouse secondary antibody coupled to peroxidase(KPL, dilution 1:7500) followed by detection with ECL reagent (Amersham Pharmacia Biotech). ST: molecular weight marker (kDa); +: cells transfected with pcDNA3.1 coding for mouse neurotrypsin; −: cells transfected with empty pcDNA3.1 (control). The arrow indicates the band of 85 kDa representing neurotrypsin.

Neurotrypsin is a secreted multi-domain protein with a length of 875 amino acids and an estimated size of 97 kDa for human neurotrypsin and 761 amino acids and a size of 85 kDa for mouse neurotrypsin (FIG. 37). The expression of this serine protease as an active protein is dependent upon proper folding and very likely on post-translational modifications, e.g. N-glycosylation which has been proposed for 2 sites in the case of the human and 3 sites for the mouse protein (Gschwend, T. P. et al., Mol. Cell. Neurosci. 9, 207-219,1997; Proba K., et al., Biochim. Biophys. Acta 1396,143-147, 1998). In addition, neurotrypsin contains a signal peptide directing the protein to the endoplasmic reticulum from where it is secreted. Neurotrypsin is not an integral membrane protein since it is lacking a transmembrane domain as determined by a hydrophobicity plot by Kyte and Doolittle (Kyte, J. and Doolittle, R. F., J. Mol. Biol. 157,105-132, 1982). The zymogen activation site of neurotrypsin shows high similarity to the one of tPA (tissue-type plasminogen activator; Tate, K. M. et al., Biochemistry 26, 338-343,1987). Cleavage at this site by a protease leads to the two fragments, one containing the non-catalytic domains with an apparent molecular weight of 55 kDa (for mouse neurotrypsin) or 67 kDa (for human neurotrypsin) and one containing only the protease domain with 30 kDa (FIG. 37). This two-chain form is still linked by a disulfide bond (FIG. 40B).

The biochemical analysis of human neurotrypsin requires protein amounts in the milligram to gram range. Because proper folding and secretion of proteins depends on many, not yet fully understood cellular and molecular mechanisms, several eukaryotic expression systems have been tested for optimal production and secretion of neurotrypsin, including baculovirus-mediated expression in insect cells, stable expression in mouse myeloma cells, and transient expression in human embryonic kidney cells (HEK). These systems have the advantage that they can easily be adapted to serum-free conditions to reduce the amount of contaminating proteins in the supernatant and to set-ups for large-scale production.

We have tested a number of eukaryotic protein expression systems with regard to their capacity to produce recombinant neurotrypsin protein for experimental use as a target for drug development. In the experiments discussed below, we demonstrated expression of neurotrypsin in HEK293T-cells and in HEK293EBNA-cells by using transient transfection procedures, we found expression of neurotrypsin in insect cells by using the baculovirus-based expression system, and we found expression of neurotrypsin in myeloma cells by using a stable transfection procedure. The protein produced by these procedures differed, ranging from incompletely processed protein that was retained in the cells to processed protein that was released into the culture supernatant. We have also established a purification procedure for neurotrypsin, consisting of two affinity columns based on specific binding properties of neurotrypsin to heparin and arginine, respectively. These were followed by conventional chromatographic procedures, including ion exchange chromatography and hydrophobic interaction chromatography.

Production of Neurotrypsin in the Human Embryonic Kidney Cell Lines HEK293T and HEK293-EBNA An expression system for transient expression of recombinant protein in the human embryonic kidney cell lines HEK 293T or HEK 293-EBNA has been established. This system has been used with great success not only for the expression of cytosolic proteins, but also for transmembrane and secreted proteins (Batard, P. et al., Gene 270, 61-68, 2001; Meissner, P., et al., Biotechnol. Bioeng. 75,197-203, 2001). The gene of interest is delivered to the cells by calcium phosphate (CaPi) transfection with efficiencies between 70-100%. The plasmid encoding for the recombinant protein that is to be expressed stays episomally and is expressed from either a cytomegalovirus (CMV) or EF-1 alpha promoter. These human-based expression systems have the advantage that post-translational modifications are very likely to be identical to modifications made by their natural producer cells. In addition, these systems are not only suitable for small-scale expression, but also for large scale production in suspension cultures (e.g. spinnerflasks 100 to 1000 ml or bioreactor 1 to 5 liter scale).

Figure 38:
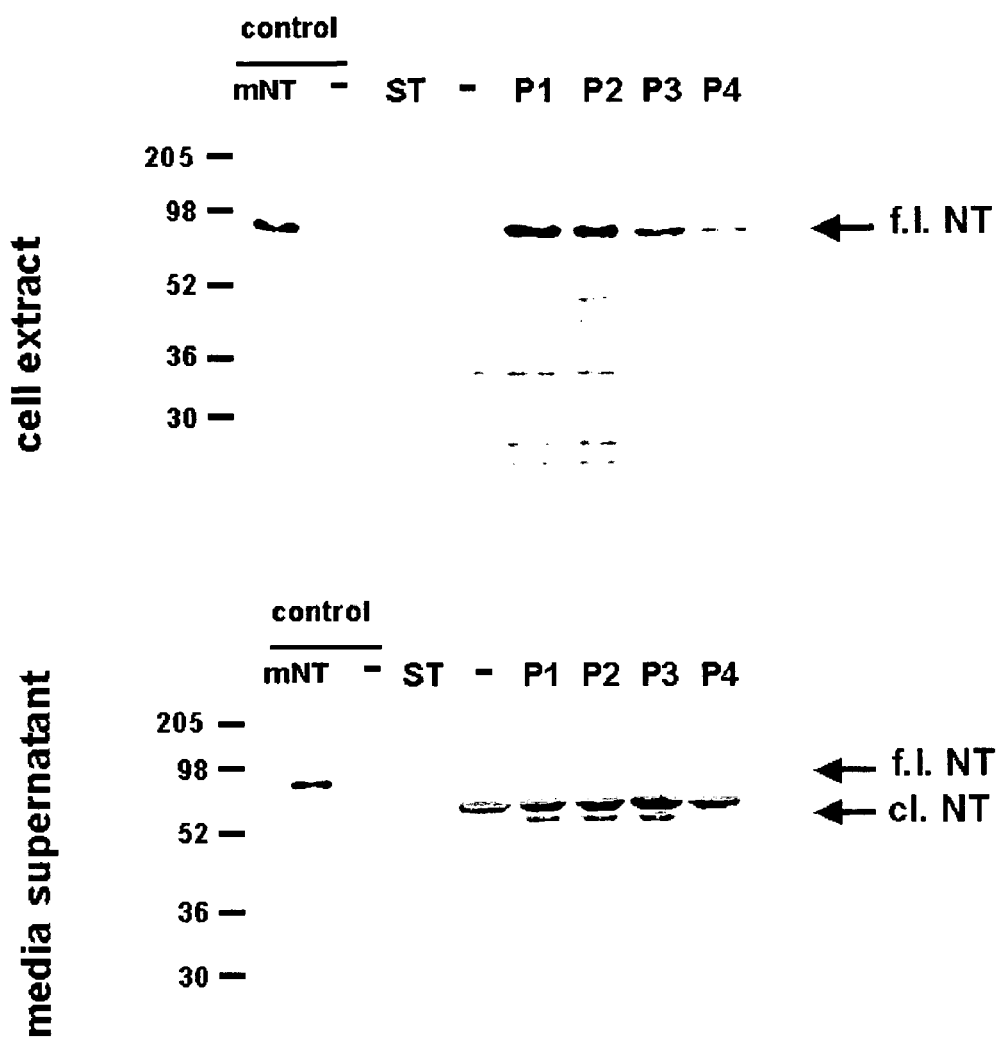
FIG. 38. Expression of neurotrypsin in HEK293-EBNA cells. HEK293T And HEK293-EBNA cells were transiently transfected with either pcDNA3.1neurotrypsin (control) or pEAK8-neurotrypsin, respectively negative control, transfection with empty pcDNA3.1 or empty pEAK8. Ten µg of total cell extracts from transfected HEK293T and HEK293-EBNA cells were loaded and separated on a 10% SDS PAGE (upper panel)In addition, media supernatant was loaded using equal volume (lower panel). Proteins were transferred to a nitrocellulose membrane. Detection of neurotrypsin was performed with the neurotrypsin-specific antibody SZ177 binding to the basic proline-rich domain (dilution 1:3,000) and a secondary goat-anti-rabbit antibody coupled to peroxidase (Sigma; dilution 1:2,000). Control: HEK293T; ST: molecular weight marker (kDa). P1 to P4 represent different transfection experiment with varying amounts of DNA transfected (P1: 200 µg, P2: 150 µg, P3: 75 µg and P4:50 µg f.l.NT, full-length neurotrypsin; cl.NT, cleaved neurotrypsin (here detected is the band of approximately 55 kDa corresponding to the non-catalytic fragment).

In pilot experiments, HEK 293T cells were transfected with a pcDNA3.1 (Invitrogen) vector encoding for neurotrypsin fused to a C-terminal histidine tag by CaPi. Cells were harvested 72 hrs post transfection. Western analysis using the anti-Tetra-His antibody (QIAGEN) detected an 85 kDa signal corresponding to the full-length mouse neurotrypsin in the cell extract and media supernatant (FIG. 38).

Figure 39:
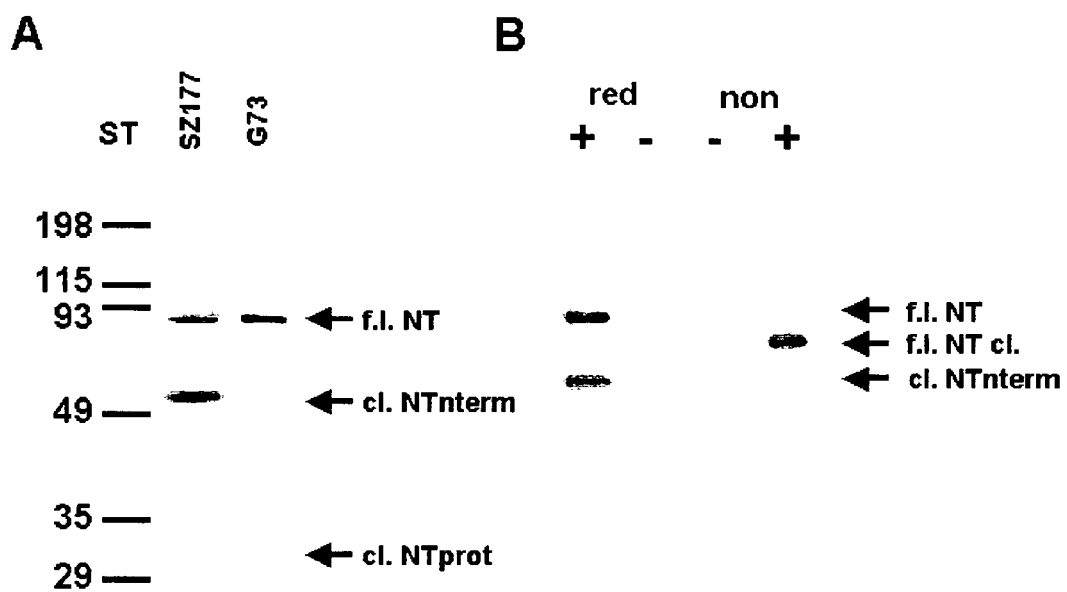
FIG. 39. Expression of neurotrypsin in High 5 insect cells. High 5 insect cells were infected with recombinant baculovirus at an MOI of 4. Supernatants were harvested 3 days post-infection and separated on a 10% SDS PAGE. After transferring the proteins on a nitrocellulose membrane, neurotrypsin was detected with the neurotrypsin-specific antibody SZ177 (dilution 1:3000) and a goat-anti-rabbit antibody coupled to peroxidase detecting the full-length protein and the non-catalytic fragment (A and B) under reducing conditions. The full-length form of neurotrypsin and the protease domain were detected using the G73 antibody binding to the protease domain and the secondary antibody rabbit-anti-goat coupled with peroxidase (dilution 1:20000). In addition, neurotrypsin conformation was analyzed under reducing and non-reducing conditions (B). Detection was performed with the SZ177 antibody. ST, molecular weight marker (kDa); f.l.NT, full-length neurotrypsin; cl.NTnterm, non-catalytic fragment; f.l.NTcl., full-length and cleaved form under non-reducing conditions; c.l.NTprot., protease domain of cleaved neurotrypsin.

Expression of neurotrypsin has also been exploited by transient transfection of HEK293-EBNA cells. It has been reported that under optimized conditions of the transfection protocol and growth of HEK cells in suspension culture yields of >20 mg/l for secreted proteins, e.g. an IgG1-type human antibody, can be achieved (Meissner, P., et al., Biotechnol. Bioeng. 75,197-203, 2001). This technology represents a rapid alternative to the widely used stable expression based on chromosomal integration of foreign DNA, which is costly and time consuming. The coding region of for the high level expression of mouse neurotrypsin fused to a C-terminal histidine tag was cloned into the pEAK8 vector (Edge Biosystems) under control of the EF-1 alpha promoter, which then is used to transfect HEK293-EBNA cells. Cells and supernatants were harvested 5 days post-transfection. Under reducing conditions full-length neurotrypsin is detected at 85 kDa in the cell extract, while in the supernatant a 55 kDa band is detected using a neurotrypsin-specific antibody directed against the basic proline-rich domain (FIG. 39). This fragment of neurotrypsin corresponds to the expected size of the non-catalytic fragment after cleavage.

Production of Neurotrypsin in Insect Cells by Infection with Recombinant Baculovirus Recombinant baculoviruses are widely used for the expression of heterologous genes cultured in insect cells. Advantage of this system is not only the similarity of post-translational modifications to those of mammalian cells which can be optimized on a case to case basis (Ailor, E. and Betenbaugh, M. J., Curr. Opin. Biotechnol. 10, 142-145, 1999), but also that insect cells can easily be adapted to suspension culture in roller bottles, shaker flasks, or to bioreactor settings for high-level expression. Expression of the gene of interest is driven by the powerful polyhedrin promoter, which is transcriptionally active in the late phase of virus propagation. It has already been demonstrated for the serine protease neuropsin that high level expression of secreted and biologically active protein can be obtained from baculovirus infected insect cells (Shimizu, C., et al., J. Biol. Chem. 273, 11189-11196,1998). Yields of 4 mg/l in adherent baculovirus-based system could be obtained from adherent cultures expressing secreted Lep d2 protein (Olsson, S. et al. (1998), *Clin. Exp. Allergy* 28, 984-991, 1998). The percentage of active secreted protein was determined in the range of 50-90% for recombinant secreted gp120 (Golden, A. et al., *Protein Expr. Purif.* 14, 8-12, 1998).

Figure 40:
FIG. 40. Expression of neurotrypsin in J558L mouse myeloma cells. Stable clones expressing neurotrypsin were generated by protoplast fusion. Cell extracts and supernatants were collected and separated on a 10% SDS PAGE. Proteins were transferred to a nitrocellulose membrane. Detection of neurotrypsin was performed with either the neurotrypsin-specific antibody SZ177 binding the basic proline-rich domain (dilution 1:3000) and a secondary goat-anti-rabbit antibody coupled to peroxidase (Sigma; dilution 1:20000)or G73 binding the protease domain (dilution 1:500) and a rabbit-anti-goat antibody coupled to peroxidase (dilution 1:20000). 1 and 2 represent two different clones analysed. S, supernatant; CE, cell extract; molecular weight marker in kDa; f.l.NT, full-length neurotrypsin; cl.NTnterm, non-catalytic fragment of cleaved neurotrypsin; cl.NTprot, protease domain of cleaved neurotrypsin.

The coding region for neurotrypsin was inserted into the pFASTbac1 vector (Invitrogen). After recombination of the neurotrypsin-coding region into the baculovirus genome insect cells were transfected and recombinant virus harvested. High5 insect cells (Invitrogen) are infected at a MOI (Multiplicity of infection) of 4. Three days post-infection cells and supernatant are collected. Full-length neurotrypsin is detected (FIG. 40). When probing with an antibody binding to the proline-rich basic domain, full-length neurotrypsin and the non-catalytic fragment at 55 kDa is detected (FIGS. 40A and 40B). Using an antibody specific for the protease domain a band at 30 kDa is observed, corresponding to the calculated molecular weight of the protease domain. Under non-reducing conditions, only one band for neurotrypsin is detected (FIG. 40B) indicating that the cleaved fragments are still linked by the disulfide bridge formed by residues Cys505 and Cys520 (FIG. 24).

Production of Neurotrypsin in Myeloma Cells

A stable expression system that is being exploited is a myeloma-based system, which had already been successfully used within our group to express secreted, recombinant axonin-1 variants (Rader C. et al., *EMBO* 15: 2056-2068, 1996; Freigang J. et al., *Cell* 101: 425433, 2000). This system had been developed based on the rational that mouse myeloma cells are the professional secretory cells in an organism (Traunecker, A., et al., *Biotechnol.* 9, 109-113, 1991). Thus, there have been reports that some mouse myeloma cell lines can produce 100 mg/l of secreted protein. The best-suited cell line is mouse myeloma J558L line which can be transfected by protoplast fusion (Oi, V. T. et al., *Proc. Natl. Acad. Sci. USA* 80, 825-829,1983).

For the stable transfection of myeloma cells the coding region of mouse and human neurotrypsin was inserted into a specially designed vector (Traunecker, A., et al., *Biotechnol.* 9, 109-113,1991). Expression by this vector is driven by an Ig κ light chain promoter and enhancer. The 3' end of the transcript of interest is spliced onto an exon encoding the Ig κ constant domain in order to mimic stable Ig transcripts. The vector contains a histidinol dehydrogenase gene that allows the selection of stable transfectants in the presence of L-histidinol. L-histidinol is a precursor of L-histamine and an inhibitor of protein synthesis. The vector has been stably transfected by protoplast fusion into the mouse myeloma cell line J558L (ECACC #88032902; European Collection of Cell Cultures, Salisbury, UK) for the production of recombinant neurotrypsin. Transfection by protoplast fusion is a highly efficient method for the direct transfer of mammalian expression vectors from bacteria to mammalian cells (Schaffner (1980), *Proc. Natl. Acad. Sci. USA* 77, 2163-2167; Sandri-Goldin et al. (1981), *Mol. Cell. Biol.* 1, 743-752; Rassoulzadegan et al. (1982), *Nature* 295, 257-259; Gillies et al. (1983), *Cell* 33, 717-728). It involves digesting bacterial cell walls with lysozyme to produce protoplasts and then fusing the protoplasts to mammalian cells in the presence of polyethylene glycol. Here we used the mouse myeloma cell line J558L. Other suitable lines for stable transfection by protoplast fusion or electroporation include mouse P3-X63Ag8.653, mouse Sp2/0-Ag14, mouse NSO, and rat YB2/0 (Gillies et al. (1989), *Biotechnology* 7, 799-804; Nakatani et al. (1989), *Biotechnology* 7: 805-810; Bebbington et al. (1992), *Biotechnology* 10: 169-175; Shitara et al. (1994), *J. Immunol. Meth.* 167, 271-278).

The following protocol is based on the myeloma expression system described by Traunecker et al. (1991), *Biotechnol.* 9, 109-113 and can easily be adapted to other systems.

For the preparation of protoplasts the glycerol stock of an *E. coli* strain 803 clone containing the mammalian expression vector is streaked on a LB agar/ampicillin plate and grown overnight at 37° C. (strain 803 available from ATCC #35581). One single colony is inoculated in 2 ml pre-warmed (37° C.) LB media containing 50 μg/ml ampicillin. After 4 hrs shaking at 250 rpm and 37° C. 100 μl of the culture is transferred to 100 ml fresh media. After the culture reached an optical density (OD at 600 nm) of about 0.6, chloramphenicol is added to a final concentration of 120 μg/ml and grown overnight at 250 rpm and 37° C. Plasmids carrying the colE1 origin of replication can be amplified in the presence of chloramphenicol (Hershfield et al. (1974), *Proc. Natl. Acad. Sci. USA* 71, 4355-3459). The overnight culture is centrifuged at 2500 g for 10 min at 4° C. The pellet is resuspended in 2.5 ml ice-cold 20% (w/v) sucrose in 50 mM Tris-HCl, pH 8.0. Five hundred μl ice-cold 1 mg/ml lysozyme in 250 mM Tris-HCl, pH 8.0, are added followed by an incubation on ice for 5 minutes. After addition of 1 ml ice-cold 250 mM EDTA, pH 8.0, and incubation on ice for 5 minutes, 1 ml ice-cold 50 mM Tris-HCl, pH 8.0, is added and the protoplast preparation incubated at room temperature for 10 minutes. During this incubation period, formation of spherical protoplasts from the usually rod-shaped bacteria can be observed using a microscope with 1000× magnification. About 90% protoplasts should be formed at the end of the incubation period. To the protoplast suspension 20 ml DMEM supplemented with 10% (w/v) sucrose, 10 mM $MgCl_2$ and 40 □l 10 mg/ml DNaseI is added. After incubation for 15 min at room temperature, the protoplast preparation is spun at 2500 g for 30 min at room temperature.

In the meantime, myeloma cells J558L are prepared for the fusion. Myeloma cells were grown in DMEM supplemented with 10% (v/v) FCS and should reach a high cell density of approximately $1 \times 10^6$ cells/ml on the day of transfection. Per protoplast fusion $5 \times 10^6$ cells are spun down at 500 g for 10 minutes at room temperature. The cells are resuspended in 5 ml pre-warmed DMEM (37° C.) and slowly layered on top of the protoplast pellet after the last centrifugation. To mix protoplasts and myeloma cells they are spun at 500 g for 10 min at room temperature. After removal of the supernatant the cells are mixed by flicking the tube. For the fusion 2 ml PEG 1500 in DMEM supplemented with 10% DMSO is added and the pellet resuspended by pipetting up and down several times. About 1 to 2 min after addition of the PEG solution, 10 ml pre-warmed DMEM (37° C.) media is added slowly. After 10 ml pre-warmed DMEM supplemented with 10% (v/v) FCS (37° C.) is added the fusion is centrifuged at 500 g for 10 min at room temperature. The supernatant is removed by aspiration and the pellet resuspended in 50 ml pre-warmed DMEM supplemented with 10% (v/v) FCS (37° C.) and 100 μl 50 mg/ml kanamycin. Finally, the cells are distributed among five 96-well tissue culture plates by adding 100 μl/well using a multipipette. After 48 hrs incubation in a humidified incubator at 37° C. with 10% $CO_2$, L-histidinol is added in a final concentration of 5 mM. Only transfected myeloma cells will survive the treatment with L-histidinol. Clones are visible about 12 to 14 days after the selection had started.

On average 40 to 50 clones are obtained per protoplast fusion. All clones were analyzed for expression by Western with neurotrypsin-specific antibodies. While the majority of myeloma cell clones expressed no or only moderate amounts of neurotrypsin, a small percentage of 5-10% revealed a very high expression level. Clones with high expression level were subcloned over three rounds of single cell dilutions to ensure the stability of neurotrypsin expression.

Figure 28:
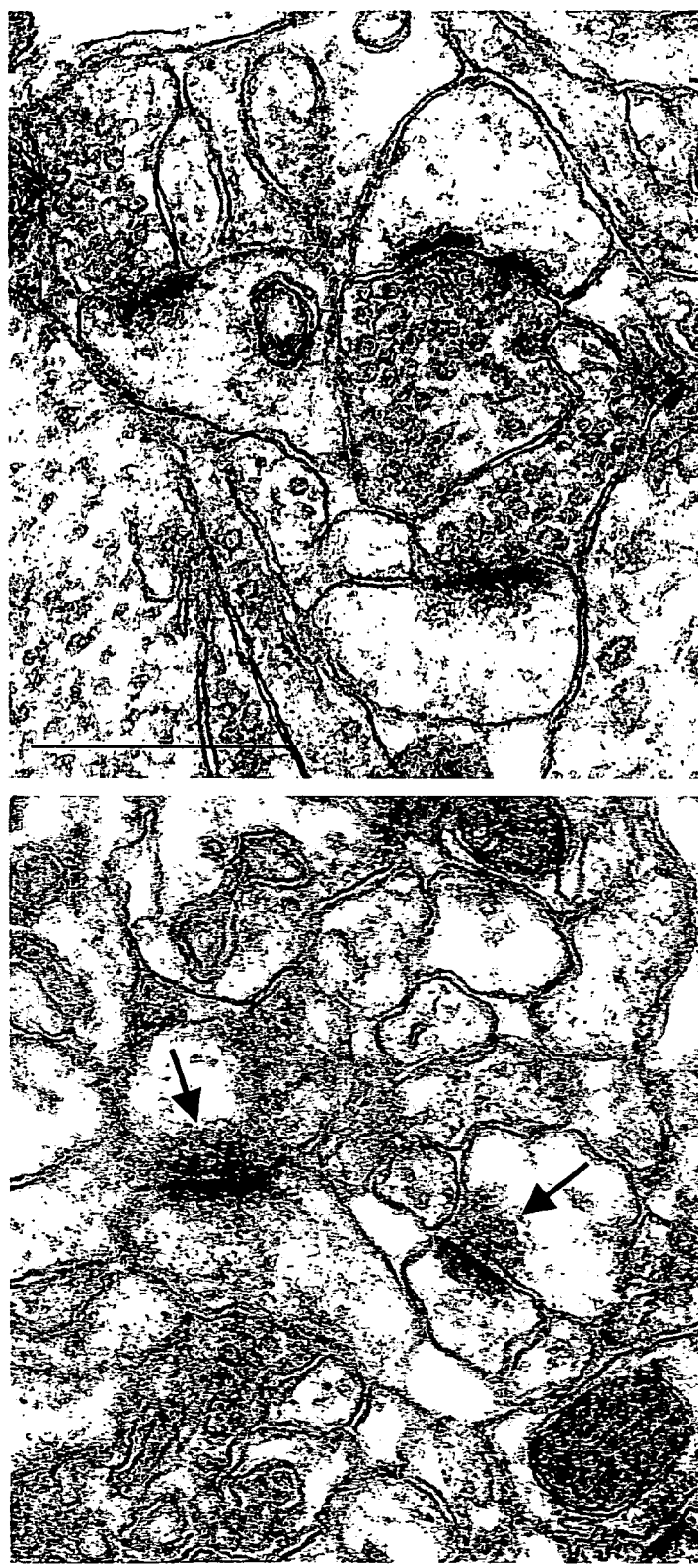
FIG. 28. Electron microscopic comparison of synapses of the hippocampal stratum radiatum of wild-type and neurotrypsin-overexpressing mice. Synapses of neurotrypsin-overexpressing mice are smaller than synapses of wild-type mice (for a quantification see FIG. 17-20). Note also the relatively small number of synaptic vesicles in the presynaptic axon terminals of neurotrypsin-overexpressing mice (arrows).

From the stably expressing clones cells and supernatant was collected. Both were separated on a 10% SDS PAGE and probed with neurotrypsin specific antibodies (FIG. 28). While full-length neurotrypsin is predominately detected in the cell extract, the 55-kDa band of the non-catalytic fragment is detected in the media supernatant when probing with an antibody against the N-terminal proline-rich basic domain. A band at 30 kDa is detected with an antibody directed against the protease domain, corresponding to the calculated molecular weight of the protease domain. Similar results are obtained with human neurotrypsin.

Additional Ways to Produce Recombinant Neurotrypsin

Alternatively, expression in eucaryotic cells may be achieved with a variety of eucaryotic expression vectors (commercially available or self-made). Likewise, a variety of eucaryotic cell lines may be used, including COS cells, CHO cells, HeLa cells, H9 cells, Jurkat cells, NIH3T3 cells, C127cells, CV1 cells, or Sf cells. For a detailed description of the use of COS cells or CHO cells, or a baculovirus-based expression system see International Application Number PCT/US96/16484 or International Publication Number WO 98/16643. In addition, the expression of neurotrypsin is also possible in yeast expression systems. The EasySelect™ *Pichia* Expression kit (Invitrogen, cat. No. K1740-01) is used for this purpose. However, expression systems of other suppliers may be used alternatively. The coding region of human neurotrypsin, excluding the natural signal sequence, was inserted into the pPICZ□ vector in frame with the □-factor signal sequence. High-level expression of the gene of interest is driven by the AOX1 promoter. The AOX1 promoter drives expression of alcohol oxidase in *Pichia*, an enzyme that catalyzes the first step in methanol metabolism. The gene of interest can be inducibly expressed by addition of up to 2% of methanol to the culture media.

Production of Neurotrypsin From A Human Cell Line With Endogenous Expression of Neurotrypsin The production of neurotrypsin may also be based on mammalian cell lines exhibiting endogenous expression of neurotrypsin. Expression of endogenous human neurotrypsin has been observed at the RNA level in the human mast cell line HMC-1 (Butterfield, J. H. et al., *Leuk. Res.* 12, 345-355, 1988; Poorafshar, M. and Hellman, L., *Eur. J. Biochem.* 261, 244-250, 1999). The HMC-1 cell line represents a naturally occurring source for properly processed and, therefore, very likely for active human neurotrypsin. These cells can be grown in suspension culture and constitutively express human neurotrypsin. The protein expressed from HMC-1 cells can be detected as 97-kDa band by a specific polyclonal antibody raised against the kringle domain in Western experiments (Sales, unpublished data). After fractionation of supernatant, cell lysate and membranes neurotrypsin localized with the membrane fraction. When the membranes are stripped under acidic conditions (200 mM glycine, pH 2.2, 1% Tween 20, 0.1% SDS) neurotrypsin can be detected in the soluble rather than the insoluble fraction, indicating a secreted and membrane-associated protein. Neurotrypsin can be purified to homogeneity from the supernatants of stripped membranes by several chromatographic steps.

However, since HMC-1 cells represent a natural source for human neurotrypsin expression coupled with the correct post-translational processing machinery, these cells are used to stably express recombinant neurotrypsin at a higher level than the endogenous gene. To this purpose HMC-1 cells are transfected with the vector pcDNA3.1 (Invitrogen) encoding for human neurotrypsin containing the neomycin resistance gene for selection with G418. It has been shown that HMC-1 cells can be transfected by electroporation (Ali, H. et al., *J. Immunol.* 165, 7215-7523, 2000). In addition, other proteins have been successfully expressed in HMC-1 cells, e.g. recombinant human proteinase 3. This protein was conformationally intact and active (Specks, U. et al., *FEBS* 390, 265-270, 1996).

Example 17

Purification of Neurotrypsin

All the expression systems that we tested in our pilot experiments, HEK293-EBNA, baculovirus-mediated expression in insect and myeloma cells, can be scaled up for large scale production of recombinant neurotrypsin. Neurotrypsin is then purified from the supernatant. Thus, the adaptation of the cells producing recombinant neurotrypsin to growth in serum-free medium, if possible, represents a major advantage for the production and purification of neurotrypsin.

For example, 1 liter supernatant derived from the myeloma expression system contains 500 mg total protein. As a first purification step, affinity purification on a heparin column is used. Other proteases, e.g. thrombin, have already been purified successfully using a heparin column (Ding, Z., et al., *Prep. Biochem.* 25: 21-28, 1995). As a second chromatographic step, an arginine sepharose 4B column was used. The eluted protein was then further purified by ion exchange chromatography on a Mono S column followed by hydrophobic interaction chromatography. Depending on the experimental requirements, additional or alternative chromatography steps on ion exchange (DEAE or Mono Q) columns or by gel filtration have also been found useful for the purification of neurotrypsin.

The source of neurotrypsin used was a conditioned cell culture supernatant resulting from the cultivation of a neurotrypsin-expressing myeloma cell line. These cells have been adapted to growth in a serum-free medium (Stoll, T. S. et al., *J. Biotechnol.* 45: 111-123, 1996; Ackermann, G. E. and Fent, K., *Marine Environmental Research* 46: 363-367, 1998) in the TechnoMouse fermenter (Integra Biosciences), originally developed for the large-scale production of monoclonal antibodies. Starting from a medium composed of DMEM (Gibco, nr. 41966-029) containing 2 mM glutamine and 10% FCS, the cells were stepwise adapted to grow in this medium with 1% FCS. Adaptation was performed in 24 well plates and the medium was exchanged approximately every second day. When cells reached confluency, they were split into another well. Throughout the whole procedure, cells were kept at a density near confluency.

Adapted cells growing well in DMEM containing 1% FCS were then transferred to the serum-free, but protein-containing, medium HL-1 (Bio-Whittacker, nr. 77201) supplemented with 0.5% FCS. In HL-1 medium the cells were then stepwise adapted to grow in HL-1 medium only (without FCS). To adapt the cells to the protein-free medium TurboDoma (Cell Culture Technologies GmbH, Zurich, nr. THP) the HL-1 medium was stepwise exchanged by TurboDoma. The adaptation steps from HL-1 to TurboDoma medium were performed analogously to the reduction of FCS.

In detail, the following conditions were used for the chromatographic purification of recombinant neurotrypsin:

Affinity Chromatography on Heparin Sepharose

As the first purification step a heparin sepharose CL-6B column was used (Amersham Pharmacia Biotech, nr. 17-0467-01). The bed volume was 80 ml and the column was run on the FPLC chromatography system. Immediately following collection from the fermenter, the pH of the conditioned medium was adjusted to 6.5 by using 1 M MES, pH 6.5, resulting in a final concentration of 50 mM. The loading buffer was 50 mM sodium chloride in 20 mM MES, pH 6.5, whereas the elution buffer contained 1 M NaCl in 20 mM MES, pH 6.5. We used a linear gradient starting at a concentration of 50 mM sodium chloride and ending at 1 M sodium chloride over a total volume of 320 ml. The eluted fractions were screened for the presence of neurotrypsin by Western blotting using an antibody against the proline-rich basic domain. For confirmation, Western blots were repeated with selected fractions using antibodies against the kringle domain and antibodies against the protease domain. The fractions containing neurotrypsin were prepared for the next step, the arginine affinity chromatography, by dialysis versus an excess of 50 mM sodium chloride in 20 mM MES, pH 6.5.

Affinity Chromatography on Arginine Sepharose

The arginine affinity chromatography was carried out using an arginine sepharose 4B column (Amersham Pharmacia Biotech, nr. 17-0524-01) with a bed volume of 18 ml. The loading buffer was 50 mM sodium chloride in 20 mM MES at pH 6.5. For elution, a gradient was used with 4 column volumes from 0 to 150 mM arginine and with 3 column volumes from 150 to 200 mM arginine. The column was regenerated with 1 M sodium chloride. The eluted fractions were screened for the presence of neurotrypsin by Western blotting using an antibody against the proline-rich basic domain. For conformation, Western blots were repeated with selected fractions using antibodies against the kringle domain and antibodies against the protease domain. The fractions containing neurotrypsin were prepared for the next step, the MonoS ion exchange chromatography by dialysis versus an excess of 50 mM sodium chloride in 20 mM MES, pH 6.5.

Ion Exchange Chromatography on the Strong Cation Exchanger MonoS

The strong cation exchanger MonoS was used with a column volume of 1 ml (MonoS HR 5/5, Amersham Pharmacia Biotech, nr. 17-0547-01). The loading buffer contained 50 mM sodium chloride in 20 mM MES, pH 6.5. The elution buffer contained 1 M sodium chloride in 20 mM MES, pH 6.5. Elution was by a linear gradient starting at 50 mM sodium chloride and ending at 1 M sodium chloride after 40 column volumes. The eluted fractions were screened for the presence of neurotrypsin by Western blotting using an antibody against the proline-rich basic domain. For confirmation, Western blots were repeated with selected fractions using antibodies against the kringle domain and antibodies against the protease domain. The fractions containing neurotrypsin were prepared for the next step, the hydrophobic interaction chromatography by dialysis versus an excess of 50 mM sodium chloride, 1 M ammonium sulfate in 20 mM MES, pH 6.5.

Hydrophobic Interaction Chromatography on the Hydrophobic Interaction Matrix Butyl Sepharose A HiTrap butyl sepharose column with a bed volume of 1 ml was used (Amersham Pharmacia Biotech, nr. 17-1357-01). The loading buffer consisted of 50 mM sodium chloride and 1 M ammonium sulfate in 20 mM MES, pH 6.5. The elution buffer was 50 mM sodium chloride, 20 mM ethylene glycol in 20 mM MES, pH 6.5. A linear gradient over 20 column volumes from 1 M to 0 M ammonium sulfate was used. The eluted fractions were screened for the presence of neurotrypsin by Western blotting using an antibody against the praline-rich basic domain. For confirmation, Western blots were repeated with selected fractions using antibodies against the kringle domain and antibodies against the protease domain. This procedure was used to purify recombinant neurotrypsin produced by the stably transfected myeloma cell line J558L. Neurotrypsin produced by a number of other recombinant expression systems (mentioned above), as well as neurotrypsin from cell lines naturally expressing neurotrypsin, e.g. the mast cell line MHC-1, and neurotrypsin from the murine, rat and bovine brain may be successfully purified using the same or a modified procedure. Neurotrypsin from animal tissue may require additional chromatographic steps, such as ion exchange chromatography on a DEAE-substituted matrix, such as DEAE-sepharose or Bio-Gel SEC DEAE-5-PW (Biorad), or on a MonoQ anion exchange column (Amersham-Pharmacia), or by gel filtration.

Example 18

Development of Specific Inhibitors of Neurotrypsin for the Use as Therapeutic Drugs for the Cure of Schizophrenia Description of the Cure: Inhibition of Neurotrypsin Represents a Novel Therapeutic Principle for Curing or Alleviating Schizophrenia Neurotrypsin: a Synaptic Serine Protease that Drives Synaptic Pruning Excessive neurotrypsin at the synapse drives synaptic pruning and, thus, generates a synaptic phenotype that is in accordance with the synaptic phenotype found in the brain of patients with schizophrenia. This experimental observation qualifies neurotrypsin as one of the factors that drive synaptic pruning.

Figure 6:
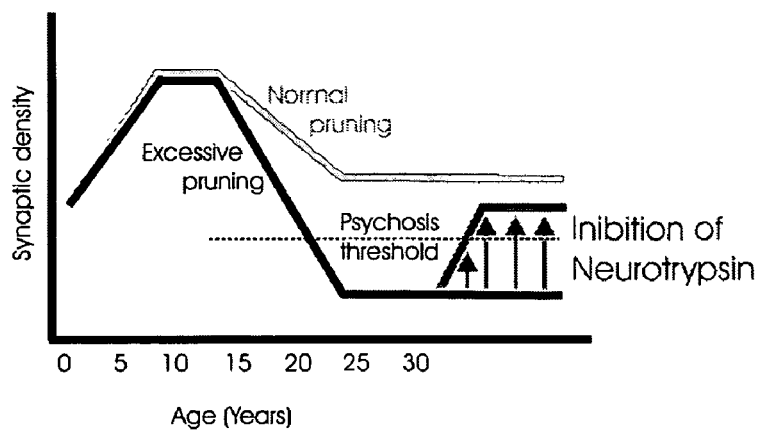
FIG. 6: Normalization of synaptic pruning by pharmacological inhibition of neurotrypsin. According to the Feinberg hypothesis, schizophrenia results from excessive synaptic pruning during late childhood and adolescence. Synaptic pruning (light gray line) is a normal developmental phenomenon during the maturation of the nervous system. Excessive synaptic pruning leading to a synaptic density below a certain threshold results in anatomical and functional disruption of neuronal connectivity and communication. Functional disruption of neuronal connectivity in turn results in impaired fundamental and secondary cognitive processes and leads to schizophrenia. The reduction of synapse numbers in the CNS of neurotrypsin-overexpressing mice indicates that inhibition of neurotrypsin may result in a lesser degree of synaptic pruning and, thus, increased synaptic number and enhanced neuronal connectivity and communication.

Inhibitors of Neurotrypsin: A Promising Novel Approach for the Treatment of Schizophrenia In a situation, where excessive synaptic pruning occurs due to the convergent action of multiple pruning-promoting factors, controlled and subtle partial inhibition of neurotrypsin diminishes the drive for synaptic pruning. This will allow a recovery from the "schizophrenic synaptic phenotype" and result in the alleviation of the schizophrenic symptoms (FIG. 6). The reduction of synapse numbers in the CNS of neurotrypsin-overexpressing mice indicates that inhibition of neurotrypsin may result in a lesser degree of synaptic pruning and, thus, increased synaptic number and enhanced neuronal connectivity and communication. Pharmaceuticals inhibiting the enzymatic function of neurotrypsin may, therefore, be used to revert the synaptic alterations in schizophrenia and to re-establish normal synaptic structure and function and, thus, stop or shorten schizophrenic episodes and protect from new episodes.

Detailed Description of Neurotrypsin at the Central Nervous System Synapse

Neurotrypsin is Located in the Active Zone of the Presynaptic Nerve Ending

Figure 7:
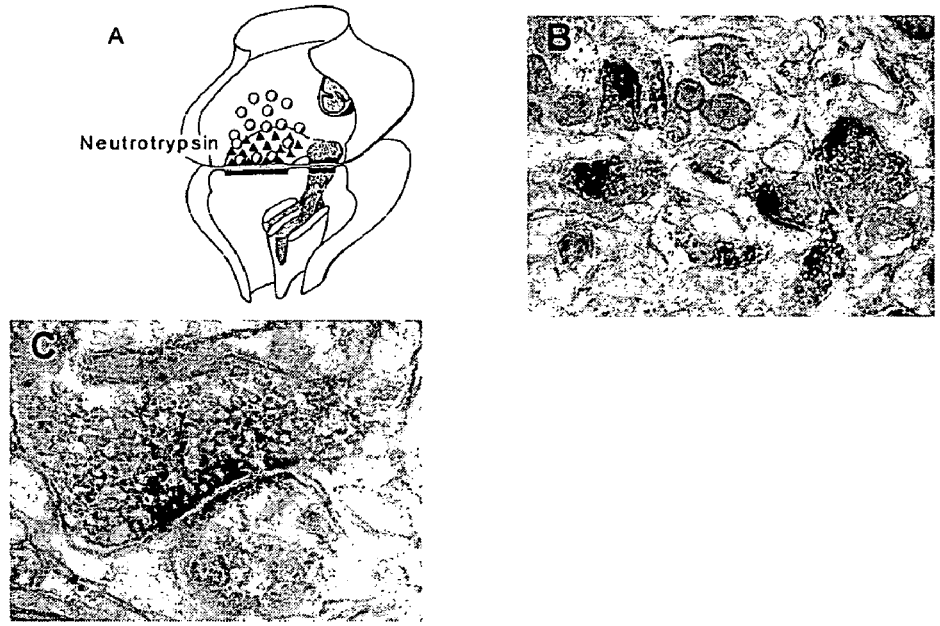
FIG. 7: The localization of neurotrypsin is shown by immuno-electron microscopy of the stratum radiatum of the CA1 region of the hippocampus of an adult mouse. A schematic drawing of a synapse. The presynaptic axon terminal is residing on top of a postsynaptic spine. The presynaptic and postsynaptic part of the synapse are separated by the synaptic cleft. The synaptic vesicles are marked as empty circles. The presynaptci active zones are marked as black triangles. The presynaptic terminal also contains a mitochondrion, in the postsynaptic spine a membranous organelle, the spine apparatus is depicted. B and C. Neurotrypsin was visualized using preembedding staining with a specific, affinity-purified antibody against the proteolytic domain of neurotrypsin and a peroxidase-conjugated secondary antibody. The neurotrypsin immunoreactivity is found at presynaptic sites of axospinous and axodendritic asymmetric synapses. The immunoperoxidase reaction product is associated with the presynaptic membrane and the active zone of the presynaptic terminal.

We have recently isolated and characterized a novel extracellular serine protease, termed neurotrypsin, based on its production by neurons and some trypsin-like features of its catalytic domain (Gschwend et al., 1997; Proba et al., 1998). The deduced amino acid sequence of neurotrypsin defines a mosaic protein of 761 amino acids consisting of a Kringle domain, followed by four scavenger receptor cysteine-rich repeats, and the serine protease domain. The structural similarity of neurotrypsin to the proteases of the blood coagulation cascade and the fibrinolytic system, such as factor X, factor IX, thrombin, tissue plasminogen activator, and plasmin suggests that it may be an element in a protease-driven extracellular signal amplification cascade in the CNS. The most prominent expression in the adult CNS was found in the cerebral cortex, the hippocampus, and the amygdala, i.e., structures engaged in the processing and storage of learned behaviors and memories. In addition, neurotrypsin was found in motor neurons of the brain stem and the spinal cord (Gschwend et al., 1997; Wolfer et al., 2001). Immuno-EM studies revealed neurotrypsin-immunoreactivity in most, if not all, populations of both excitatory and inhibitory axonal terminals. Specifically, neurotrypsin-immunoreactivity was enriched in the presynaptic active zone (FIG. 7) and a subpopulation of synaptic vesicles (Meskenaite et al., in preparation). In order to obtain independent evidence for the synaptic localization of neurotrypsin, a biochemical approach was chosen. Synaptosomes were prepared by subcellular fractionation according to a well established and generally accepted protocol. The proteins of the synaptosomes were analyzed by Western blotting, using specific antibodies against neurotrypsin. We found that neurotrypsin protein was clearly enriched in the synaptosomes compared to mouse brain homogenate. In agreement with the immunocytochemical data, these results localize neurotrypsin at synapses. For an even more detailed localization by this biochemical approach, synaptosomes were further subdivided according to a subcellular fractionation protocol, and synaptic membranes were prepared. In the analysis of the synaptic membranes using the Western Blotting technique, we found that synaptic membranes were further enriched for neurotrypsin when compared to synaptosomes, indicating that synaptic membranes contain the highest concentration of neurotrypsin. These results are in agreement with the observations made in the immunocytochemical analyses. In summary, these results indicate that neurotrypsin is located in the presynaptic terminal, in particular in the presynaptic membrane lining the synaptic cleft at the presynaptic active zone. This localization puts neurotrypsin in a strategic position to control synaptic structure and function.

Neurotrypsin is a Modulator of Synaptic Function

Inactivation of Neurotrypsin by a Truncating Deletion in the Human Neurotrypsin Gene Results in a Severe Mental Retardation.

Figure 8:
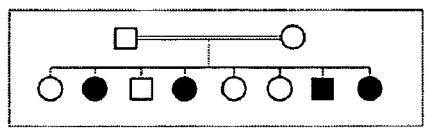
FIG. 8: A truncating deletion in the PRSS12 gene encoding neurotrypsin was found by investigation of an inbred Eastern Algerian family with mentally retarded children (black symbols). The parents were first degree cousins. Four of their eight children (3 girls and 1 boy) were mentally retarded. Cognitive impairment and a low IQ (below 50) were consistent features in the four affected individuals. By means of a genome-wide screen using 400 microsatellite markers a single region of shared homozygosity on chromosome 4q24-q25 was identified.

In collaboration with the laboratory of Dr. Laurence Colleaux, Hôpital Necker-Enfants Malades, Paris (France), we recently reported that neurotrypsin is involved in autosomal recessive mental retardation in humans (Molinari, F. et al., Science 298, 1779-1781, 2002). By homozygosity mapping in an inbred family with four mentally retarded children (FIG. 8), the disease-causing gene was tracked down on chromosome 4q24-q25, were we had previously identified the chromosome localization of the neurotrypsin-encoding gene, PRSS12, by fluorescent in situ hybridization (Kozlov S. V. et al., Cytogenet Cell Genet. 84, 107-108, 1999).

PCR-amplification followed by nucleotide sequence analysis, revealed a 4 base-pair deletion in exon 7 of the PRSS12 gene. Exon 7 is encoding for the peptide sequence in the region of the $3^{rd}$ scavenger receptor cysteine-rich (SRCR) domain. The resulting frameshift in the code leads to the synthesis of a nonsense amino acid sequence before ending in a premature translational stop codon 47 amino acids downstream of the mutation. Thus, a truncated and, therefore, incomplete neurotrypsin protein is generated. Cognitive impairment and a low IQ (below 50) were consistent features in the four affected individuals. The mental retardation phenotype resulting in humans is well compatible with our observations in our ongoing functional studies on neurotrypsin. These observations indicate that neurotrypsin is a modulator of synaptic function and its deficiency becomes most apparent in brain structures responsible for higher brain functions, such as cognitive functions, learning, and memory. Basic synaptic functions and the formation of synapses during neural development are apparently not affected in the absence of functional neurotrypsin, as individuals deficient in active neurotrypsin due to the truncating deletion in the third SRCR domain had normal neural functions in all other investigated features, including normal motor and vegetative functions.

Excessive Neurotrypsin in Neurons of Transgenic Mice Results in Enhanced Long-term Potentiation (Evidence From Transgenic Mice).

To investigate the effect of excessive neurotrypsin on synaptic structure and function, we generated a mouse line with a conditional transgene for neurotrypsin. In the transgene, a transcriptional stop sequence flanked by two loxP sites was inserted between the Thy-1 promoter and the segment coding for neurotrypsin. In this line, regional expression of the transgene may be induced by crossing in a transgene with a regionally expressed Cre recombinase.

Figure 9:
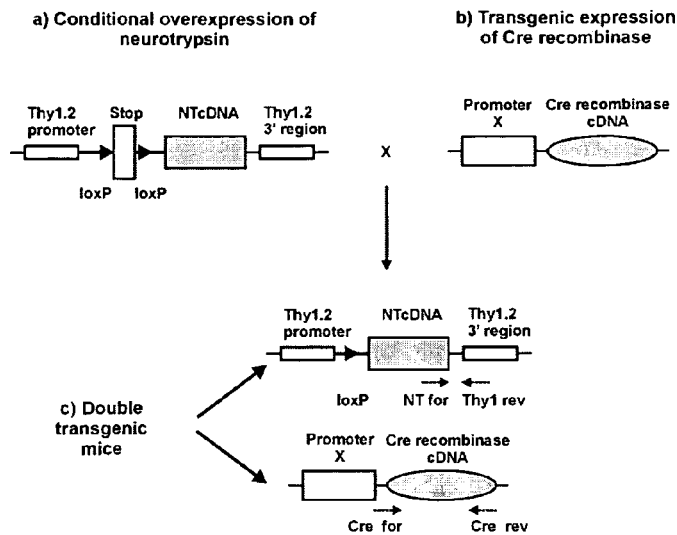
FIG. 9: Transgenic constructs and the generation of neurotrypsin-overexpressing mice a) Construct for the conditional overexpression of neurotrypsin. Conditional overexpression indicates that the transgene is inserted into the mouse genome in an inactive form. In this conditional transgene, the coding part of the neurotrypsin cDNA was incorporated into the Thy1 gene and, thus, put under the control of the Thy1 promoter. In the graph, the first box marked by Thy1 indicates the transcription regulating promoter at the 5' end of the Thy-1 gene. The second box marked by Thy1 indicates the 3' terminal sequences of the Thy1 gene. Between the Thy-1 promoter and the cDNA encoding neurotrypsin, a transcriptional stop segment flanked by two IoxP sequences was inserted. Transcription from the Thy-1 promoter of this transgene, thus, stops before reaching the coding sequence of neurotrypsin. The inactive transgene can be converted into an active transgene by Cre recombinase. Cre recombinase promotes recombination at the IoxP sites and, thus, excision of the transcriptional stop sequence b) Construct for expression of Cre-recombinase under the control of the any promoter X. Activation of the inactive transgene can be obtained by crossing the mice containing the inactive Thy1-neurotrypsin (inact.Nt) transgene with the mice containing the X-Cre transgene. If a heterozygous inactive.Nt mouse is crossed with a heterozygotus X-Cre mouse, the double-transgenic mice among the offspring express the Thy1-neurotrypsin transgene in the activated form in all cells which express Cre recombinase (The expressed Cre-recombinase deletes the transcriptional stop sequence by promoting recombination at the IoxP sequences). One IoxP sequence remains within the activated Thy1-neurotrypsin transgene. The removed segment composed of the other IoxP sequence and the transcriptional stop sequence is shown on the right. The mice were genotyped with the PCR method. The dashed arrows mark the region of the oligonucleotide primers used in the PCR.

For clarity, the principles of the constructs made for the conditional overexpression of neurotrypsin are presented in FIG. 9. The neurotrypsin cDNA was incorporated into the Thy1 gene. A transcription stop sequence flanked by loxP sequences was inserted between the Thy1 promoter and the ORF of neurotrypsin. For the activation of the conditional neurotrypsin transgene, a number of mouse lines have already been generated. For general activation, a mouse line expressing the Cre recombinase under the CMV promoter is often used. The CMV promoter drives early embryonic and general expression of the Cre recombinase and, thus, loxP-dependent recombination occurs in all cell types and tissues. Mouse lines with more restricted expression of Cre recombinase are also available. They may be used for regional activation of the loxP-dependent recombination. To generate double-transgenic mice, a heterozygotic neurotrypsin mouse is crossed with a heterozygotic Cre mouse. The coexpression of the conditional neurotrypsin transgene with the Cre recombinase results in excision of the loxP-flanked stop sequence. One loxP sequence remains in the neurotrypsin expression cassette, but has no effect. The removed segment with the other loxP and the stop sequence is not shown. The mice are genotyped with PCR using primers indicated as dashed arrows.

To test whether neurotrypsin is involved in synaptic processes, the effect of neurotrypsin overexpression in the mouse brain was analyzed by electrophysiological recordings from hippocampal slices (collaboration with Dr. C. Stricker). Based on the availability of Cre-expressing mice at the time, neurotrypsin overexpression was induced by crossing neurotrypsin mice with CMV-Cre mice. Long-term plasticity was induced in hippocampal slices by stimulation of the Schaffer collaterals and field excitatory postsynaptic potentials (fEPSP) in the stratum radiatum of the CA1 region were measured. Transgenic mice showed a significantly enhanced LTP compared to control mice.

Figure 10:
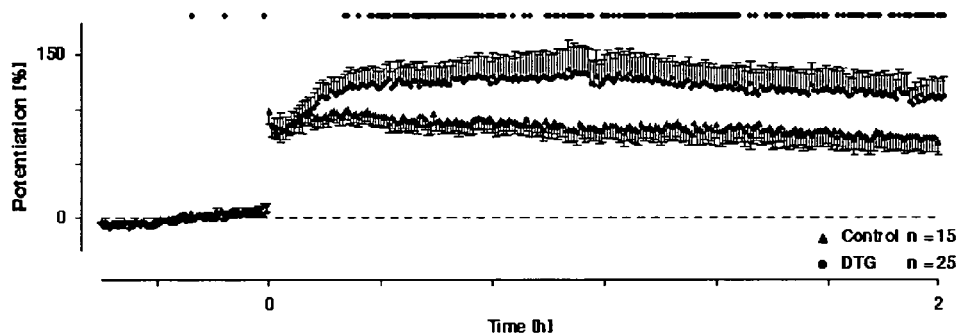
FIG. 10: An experimental series comparing LTP of mice overexpressing neurotrypsin (DTG: double transgenic) with wild-type controls is shown. Each point represents the mean peak amplitude calculated from the pooled slopes of the fEPSPs. Results from control animals (triangles) and the double-transgenic group (squares) are compared. The fEPSP time courses are normalized to the mean of the base-line responses and expressed as percentage of potentiation (+/− standard deviation). For clarity of presentation, error bars are only shown in one direction. The dots above the graph indicate where the difference between the means of the two groups reaches significance ($p<0.05$, determined by a paired Student t-test).

We studied transgenic mice overexpressing neurotrypsin in neurons of the CNS in comparison with wild-type mice (FIG. 10). By stimulating and recording from hippocampal slices we found a significant enhancement of long-term potentiation in the hippocampal CA1 region of neurotrypsin-overexpressing mice. Mice overexpressing an inactive form of neurotrypsin, lacking catalytic (i.e. proteolytic) activity due to a genetically engineered mutation of the catalytic site serine to an alanine, did not exhibit enhanced long-term potentiation. Likewise, mice expressing an inactive transgene that did not result in production of transgene-derived neurotrypsin, did not exhibit enhanced long-term potentiation. Therefore, the enhanced long-term potentiation in the hippocampus of neurotrypsin-overexpressing mice is due to the catalytic effect derived from excessive neurotrypsin.

In summary, our current results indicate that neurotrypsin has a concentration-dependent effect on complex synaptic functions. In the total absence of neurotrypsin, cognitive functions are severely impaired, as demonstrated by the occurrence of a severe form of mental retardation in individuals that are homozygous for a defect in the neurotrypsin gene. In contrast, long-term potentiation, a mechanism generally considered as a cellular correlate of synaptic plasticity that underlies learning and memory as well as other higher brain functions, is altered when a higher than normal amount of neurotrypsin is produced in CNS neurons. These observations clearly demonstrate the role of neurotrypsin as a regulator of synaptic functions that is required for memory and learning and other higher brain functions.

Overexpression of Neurotrypsin in Neurons of Transgenic Mice Results in a Reduced Number of Synapses in the Cerebral Cortex and the Hippocampus Excessive amounts of neurotrypsin cause a significant change in number and morphology of the synapses in the central nervous system. Evidence for structural changes was found both with electrophysiological and morphological methods. A physiological correlate of a reduced neuronal surface area in neurotrypsin-overexpressing mice was found with electrical recordings of the capacitance. The time-corese of the change of capacitance after a voltage step revealed a significantly reduced whole-cell capacitance in hippocampal neurons of neurotrypsin-overexpressing mice. A reduced whole cell capacitance may be due to a reduced surface area of the membrane, if other possible causes can be excluded. Importantly, changed membrane transductance was excluded experimentally as a cause of the observed change. Therefore, we have investigated the extension and the branching pattern of the neuronal dendrites as well as the size of the neuronal somas. We found no significant deviation of the size at the branching pattern of the neuronal dendrites between neurotrypsin-overexpressing and wild-type mice. Neuronal somas were, if anything, rather enlarged. The observation of a reduced whole-cell capacitance without a reduction of the surface area of the cell soma and the dendrites strongly suggests the reduction in the dendritic spines. The dendritic spines contribute between 50% and 70% to the surface of the neuron and are not included in the measurements of the length and branching pattern of the dendrites. This possibility was evaluated by counting and measuring synapses in neuropil regions and inspecting dendritic spines along dye-filled dendrites.

Figure 11:
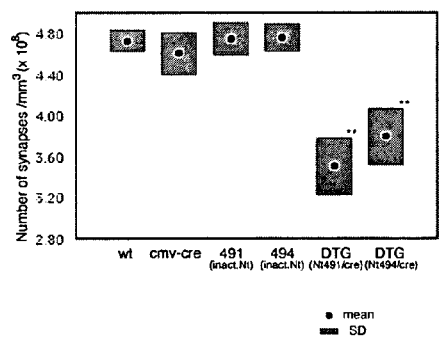
FIG. 11: Quantification of the number of synapses per volume of tissue in the neuropil of the stratum radiatum of the CA1 region of the hippocampus. In all experimental animals, the number of synapses per volume of tissue was determined from electron microscopic sections taken from the same location in the stratum radiatum of the CA1 region of the hippocampus wt: wild type; CMV-Cre: transgenic line expressing the Cre recombinase under the control of the CMV promoter; 491 (inact.Nt): transgenic line 491, bearing the inactive transgene, containing a transcriptional stop segment; 494(inact.Nt): transgenic line 494, bearing the inactive transgene, containing a transcriptional stop segment; DTG(Nt491/cre): double transgenic mouse descending from the line 491, in which the inactive neurotrypsin transgene has been activated by crossing in the Cre recombinase; DTG(Nt494/cre): double transgenic mouse descending from the line 494, in which the inactive neurotrypsin transgene has been activated by crossing in the Cre recombinase. (**, $p<0.01$).
Figure 12:
FIG. 12: Spines on secondary dendritic branches of CA1 pyramidal neurons of wild-type mice (A and B) and transgenic mice overexpressing neurotrypsin (C and D). CA1 pyramidal cells were iontophoretically filled with biocytin during electrophysiological in vitro studies and visualised using avidin-biotin-peroxidase histochemistry. Dendrites of wild-type mice have many long, well-developed spines (large arrows); in addition, many short, stubby-shape spines (small arrowheads) are also found. Dendrites of neurotrypsin-overexpressing mice (littermates) are dominated by short stubby-shape spines (small arrowheads); long, well-developed spines (large arrows) are very rare. Note, also, that the total spine density (number of spines per unit length of dendrite) is markedly lower in neurotrypsin-overexpressing mice (C and D).

We found a reduction, both in the number of total synapses per area (FIG. 11) and in three measurements reflecting synaptic size, namely the area of the presynaptic axon terminal, the area of the postsynaptic spine, and the synaptic length (determined as the length of the apposition of the presynaptic and the postsynaptic membranes. By inspection of the spines along dye-filled dendrites, we found a reduction in the size and the number of spines in the neurotrypsin-overexpressing mice (FIG. 12). These measurements are in mutual agreement, because many synapses end on dendritic spines. Therefore, fewer synapses and fewer dendritic spines represent two readouts of the same phenomenon. In addition, reductions in the size of the presynaptic terminal, the postsynaptic spines, and other synaptic parameters, such as synaptic length were found in accordance with smaller, less-well developed spines observed after dye-labeling of dendrites.

CONCLUSIONS

The role of neurotrypsin as a regulator of synaptic structure, function, and plasticity has been extensively documented in our laboratory over the past years. Neurotrypsin clearly qualifies as a protein regulating higher cognitive functions by modulating synaptic structure and function. Neurotrypsin is indispensable for normal cognitive function of the human brain. Complete inactivity of neurotrypsin in human subjects, due to a truncating deletion in the PRSS12 gene encoding neurotrypsin, causes severe mental retardation. In contrast, an excessive level of neurotrypsin at the synapse causes a morphological phenotype identical with the synaptic alterations found in the brains of schizophrenic patients in all currently available details. Electrophysiological alterations in these mice, such as enhanced long-term potentiation and enhanced neuronal excitability are also well compatible with alterations expected in schizophrenic brains, where often excessive ill-controlled activity occurs, resulting in the so-called positive symptoms, such as hallucinations. Therefore, pharmaceutical drugs that reduce the activity of neurotrypsin may be of practical use as regulators of synaptic homeostasis and may counteract cognitive deficits caused by an imbalance of synaptic plasticity. In particular, such drugs have a great potential for counteracting the structural and functional alterations found associated with schizophrenia and, thus, alleviate schizophrenic symptoms, and prevent further episodes.

What is claimed is:

1. A method for identifying compounds useful in treatment of schizophrenia comprising
   (a) providing a target protein comprising SEQ ID NO: 5;
   (b) bringing said target protein in contact with a test compound;
   (c) identifying a change in the catalytic activity of the target protein relative to the activity of the target protein in the absence of said compound; and
   (d) isolating said compound inhibiting the catalytic activity of the target protein.

2. The method of claim 1, wherein the target protein consists of the sequence of SEQ ID NO: 5.

3. The method of claim 1 wherein said target protein has the sequence of SEQ ID NO: 2.

4. The method of claim 1, wherein the target protein is produced by recombinant protein expression using a eukaryotic or prokaryotic expression vector, followed by purification of the protein.

5. The method of claim 1, wherein the target protein is obtained by purification from a natural source.

* * * * *

UNITED STATES PATENT AND TRADEMARK OFFICE
CERTIFICATE OF CORRECTION

PATENT NO. : 7,666,613 B2  
APPLICATION NO. : 10/843299  
DATED : February 23, 2010  
INVENTOR(S) : Peter Sonderegger It is certified that error appears in the above-identified patent and that said Letters Patent is hereby corrected as shown below:

The priority information which is clearly set forth in the Declaration filed August 25, 2004 is missing from the cover page of the patent.

Please add INID No. (30) and insert the following priority applications:

-- PCT/IB98/00625 filed April 24, 1998.

CH966/97 filed April 25, 1997.

Application No. 09/403,724 filed December 20, 1999. --.

Signed and Sealed this

Ninth Day of November, 2010

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,613 B2 | Page 1 of 1 |
| APPLICATION NO. | : 10/843299 | |
| DATED | : February 23, 2010 | |
| INVENTOR(S) | : Sonderegger | |

It is certified that error appears in the above-identified patent and that said Letters Patent is hereby corrected as shown below:

Col. 1

At page 1 of the specification, paragraph [0001] after Technical Field line 5 insert the following paragraph:

--This application is a continuation-in-part of U.S. Application No. 09/403,724 filed 12/20/1999 which is the U.S. National stage of PCT/IB98/00625 filed 04/04/1998 and which claims the benefit of priority from Swiss Application No. 966/97 filed 04/26/1997.--

Signed and Sealed this
Twenty-first Day of June, 2011

David J. Kappos
*Director of the United States Patent and Trademark Office*

SEQUENCE LISTING

```
<160> NUMBER OF SEQ ID NOS: 28

<210> SEQ ID NO 1
<211> LENGTH: 3350
<212> TYPE: DNA
<213> ORGANISM: Homo sapiens
<220> FEATURE:
<221> NAME/KEY: sig_peptide
<222> LOCATION: (44)..(103)
<220> FEATURE:
<221> NAME/KEY: mat_peptide
<222> LOCATION: (104)..(2668)
<220> FEATURE:
<221> NAME/KEY: CDS
<222> LOCATION: (44)..(2668)
<220> FEATURE:
<221> NAME/KEY: 5'UTR
<222> LOCATION: (1)..(43)
<220> FEATURE:
<221> NAME/KEY: 3'UTR
<222> LOCATION: (2669)..(3350)
```

<400> SEQUENCE: 1

```
cggaagctgg ggagcatgga ccagaccccg cagcgctggc acc atg acg ctc gcc      55
                                              Met Thr Leu Ala
                                              -20 cgc ttc gtg cta gcc ctg atg tta ggg gcg ctc ccc gaa gtg gtc ggc     103
Arg Phe Val Leu Ala Leu Met Leu Gly Ala Leu Pro Glu Val Val Gly
    -15                 -10                 -5                  -1 ttt gat tct gtc ctc aat gat tcc ctc cac cac agc cac cgc cat tcg     151
Phe Asp Ser Val Leu Asn Asp Ser Leu His His Ser His Arg His Ser
  1               5                  10                  15 ccc cct gcg ggt ccg cac tac ccc tat tac ctt ccc acc cag cag cgg     199
Pro Pro Ala Gly Pro His Tyr Pro Tyr Tyr Leu Pro Thr Gln Gln Arg
                20                  25                  30 ccc ccg acg acg cgt ccg ccg ccg cct ctc ccg cgc ttc ccg cgc ccc     247
Pro Pro Thr Thr Arg Pro Pro Pro Leu Pro Arg Phe Pro Arg Pro
            35                  40                  45 ccg cgg gcg ctc cct gcc cag cgc ccg cac gcc ctc cag gcc ggg cac     295
Pro Arg Ala Leu Pro Ala Gln Arg Pro His Ala Leu Gln Ala Gly His
    50                  55                  60 acg ccc cgg ccg cac ccc tgg ggc tgc ccc gcc ggc gag cca tgg gtc     343
Thr Pro Arg Pro His Pro Trp Gly Cys Pro Ala Gly Glu Pro Trp Val
65                  70                  75                  80 agc gtg acg gac ttc ggc gcc ccg tgt ctg cgg tgg gcg gag gtg cca     391
Ser Val Thr Asp Phe Gly Ala Pro Cys Leu Arg Trp Ala Glu Val Pro
                85                  90                  95 ccc ttc ctg gag cgg tcg ccc cca gcg agc tgg gct cag ctg cga gga     439
Pro Phe Leu Glu Arg Ser Pro Pro Ala Ser Trp Ala Gln Leu Arg Gly
            100                 105                 110 cag cgc cac aac ttt tgt cgg agc ccc gac ggc gcg ggc aga ccc tgg     487
Gln Arg His Asn Phe Cys Arg Ser Pro Asp Gly Ala Gly Arg Pro Trp
    115                 120                 125 tgt ttc tac gga gac gcc cgt ggc aag gtg gac tgg ggc tac tgc gac     535
Cys Phe Tyr Gly Asp Ala Arg Gly Lys Val Asp Trp Gly Tyr Cys Asp
130                 135                 140 tgc aga cac gga tca gta cga ctt cgt ggc ggc aaa aat gag ttt gaa     583
Cys Arg His Gly Ser Val Arg Leu Arg Gly Gly Lys Asn Glu Phe Glu
145                 150                 155                 160 ggc aca gtg gaa gta tat gca agt gga gtt tgg ggc act gtc tgt agc     631
Gly Thr Val Glu Val Tyr Ala Ser Gly Val Trp Gly Thr Val Cys Ser
                165                 170                 175 agc cac tgg gat gat tct gat gca tca gtc att tgt cac cag ctg cag     679
Ser His Trp Asp Asp Ser Asp Ala Ser Val Ile Cys His Gln Leu Gln
            180                 185                 190 ctg gga gga aaa gga ata gca aaa caa acc ccg ttt tct gga ctg ggc     727
Leu Gly Gly Lys Gly Ile Ala Lys Gln Thr Pro Phe Ser Gly Leu Gly
    195                 200                 205 ctt att ccc att tat tgg agc aat gtc cgt tgc cga gga gat gaa gaa     775
Leu Ile Pro Ile Tyr Trp Ser Asn Val Arg Cys Arg Gly Asp Glu Glu
210                 215                 220 aat ata ctg ctt tgt gaa aaa gac atc tgg cag ggt ggg gtg tgt cct     823
Asn Ile Leu Leu Cys Glu Lys Asp Ile Trp Gln Gly Gly Val Cys Pro
225                 230                 235                 240 cag aag atg gca gct gct gtc acg tgt agc ttt tcc cat ggc cca acg     871
Gln Lys Met Ala Ala Ala Val Thr Cys Ser Phe Ser His Gly Pro Thr
                245                 250                 255 ttc ccc atc att cgc ctt gct gga ggc agc agt gtg cat gaa ggc cgg     919
Phe Pro Ile Ile Arg Leu Ala Gly Gly Ser Ser Val His Glu Gly Arg
            260                 265                 270
```

-continued

| | | |
|---|---|---|
| gtg gag ctc tac cat gct ggc cag tgg gga acc gtt tgt gat gac caa<br>Val Glu Leu Tyr His Ala Gly Gln Trp Gly Thr Val Cys Asp Asp Gln<br>275                    280                    285 | 967 |
| tgg gat gat gcc gat gca gaa gtg atc tgc agg cag ctg ggc ctc agt<br>Trp Asp Asp Ala Asp Ala Glu Val Ile Cys Arg Gln Leu Gly Leu Ser<br>290                    295                    300 | 1015 |
| ggc att gcc aaa gca tgg cat cag gca tat ttt ggg gaa ggg tct ggc<br>Gly Ile Ala Lys Ala Trp His Gln Ala Tyr Phe Gly Glu Gly Ser Gly<br>305                    310                    315                    320 | 1063 |
| cca gtt atg ttg gat gaa gta cgc tgc act ggg aat gag ctt tca att<br>Pro Val Met Leu Asp Glu Val Arg Cys Thr Gly Asn Glu Leu Ser Ile<br>                    325                    330                    335 | 1111 |
| gag cag tgt cca aag agc tcc tgg gga gag cat aac tgt ggc cat aaa<br>Glu Gln Cys Pro Lys Ser Ser Trp Gly Glu His Asn Cys Gly His Lys<br>                    340                    345                    350 | 1159 |
| gaa gat gct gga gtg tcc tgt acc cct cta aca gat ggg gtc atc aga<br>Glu Asp Ala Gly Val Ser Cys Thr Pro Leu Thr Asp Gly Val Ile Arg<br>                  355                    360                    365 | 1207 |
| ctt gca ggt ggg aaa ggc agc cat gag ggt cgc ttg gag gta tat tac<br>Leu Ala Gly Gly Lys Gly Ser His Glu Gly Arg Leu Glu Val Tyr Tyr<br>370                    375                    380 | 1255 |
| aga ggc cag tgg gga act gtc tgt gat gat ggc tgg act gag ctg aat<br>Arg Gly Gln Trp Gly Thr Val Cys Asp Asp Gly Trp Thr Glu Leu Asn<br>385                    390                    395                    400 | 1303 |
| aca tac gtg gtt tgt cga cag ttg gga ttt aaa tat ggt aaa caa gca<br>Thr Tyr Val Val Cys Arg Gln Leu Gly Phe Lys Tyr Gly Lys Gln Ala<br>                    405                    410                    415 | 1351 |
| tct gcc aac cat ttt gaa gaa agc aca ggg ccc ata tgg ttg gat gac<br>Ser Ala Asn His Phe Glu Glu Ser Thr Gly Pro Ile Trp Leu Asp Asp<br>                  420                    425                    430 | 1399 |
| gtc agc tgc tca gga aag gaa acc aga ttt ctt cag tgt tcc agg cga<br>Val Ser Cys Ser Gly Lys Glu Thr Arg Phe Leu Gln Cys Ser Arg Arg<br>                  435                    440                    445 | 1447 |
| cag tgg gga agg cat gac tgc agc cac cgc gaa gat gtt agc att gcc<br>Gln Trp Gly Arg His Asp Cys Ser His Arg Glu Asp Val Ser Ile Ala<br>450                    455                    460 | 1495 |
| tgc tac cct ggc ggc gag gga cac agg ctc tct ctg ggt ttt cct gtc<br>Cys Tyr Pro Gly Gly Glu Gly His Arg Leu Ser Leu Gly Phe Pro Val<br>465                    470                    475                    480 | 1543 |
| aga ctg atg gat gga gaa aat aag aaa gaa gga cga gtg gag gtt ttt<br>Arg Leu Met Asp Gly Glu Asn Lys Lys Glu Gly Arg Val Glu Val Phe<br>                  485                    490                    495 | 1591 |
| atc aat ggc cag tgg gga aca atc tgt gat gat gga tgg act gat aag<br>Ile Asn Gly Gln Trp Gly Thr Ile Cys Asp Asp Gly Trp Thr Asp Lys<br>500                    505                    510 | 1639 |
| gat gca gct gtg atc tgt cgt cag ctt ggc tac aag ggt cct gcc aga<br>Asp Ala Ala Val Ile Cys Arg Gln Leu Gly Tyr Lys Gly Pro Ala Arg<br>515                    520                    525 | 1687 |
| gca aga acc atg gct tac ttt gga gaa gga aaa gga ccc atc cat gtg<br>Ala Arg Thr Met Ala Tyr Phe Gly Glu Gly Lys Gly Pro Ile His Val<br>530                    535                    540 | 1735 |
| gat aat gtg aag tgc aca gga aat gag agg tcc ttg gct gac tgt atc<br>Asp Asn Val Lys Cys Thr Gly Asn Glu Arg Ser Leu Ala Asp Cys Ile<br>545                    550                    555                    560 | 1783 |
| aag caa gat att gga aga cac aac tgc cgc cac agt gaa gat gca gga<br>Lys Gln Asp Ile Gly Arg His Asn Cys Arg His Ser Glu Asp Ala Gly<br>                    565                    570                    575 | 1831 |
| gtt att tgt gat tat ttt ggc aag aag gcc tca ggt aac agt aat aaa<br>Val Ile Cys Asp Tyr Phe Gly Lys Lys Ala Ser Gly Asn Ser Asn Lys<br>580                    585                    590 | 1879 |

```
gag tcc ctc tca tct gtt tgt ggc ttg aga tta ctg cac cgt cgg cag    1927
Glu Ser Leu Ser Ser Val Cys Gly Leu Arg Leu Leu His Arg Arg Gln
            595                 600                 605 aag cgg atc att ggt ggg aaa aat tct tta agg ggt ggt tgg cct tgg    1975
Lys Arg Ile Ile Gly Gly Lys Asn Ser Leu Arg Gly Gly Trp Pro Trp
610                 615                 620 cag gtt tcc ctc cgg ctg aag tca tcc cat gga gat ggc agg ctc ctc    2023
Gln Val Ser Leu Arg Leu Lys Ser Ser His Gly Asp Gly Arg Leu Leu
625                 630                 635                 640 tgc ggg gct acg ctc ctg agt agc tgc tgg gtc ctc aca gca gca cac    2071
Cys Gly Ala Thr Leu Leu Ser Ser Cys Trp Val Leu Thr Ala Ala His
                645                 650                 655 tgt ttc aag agg tat ggc aac agc act agg agc tat gct gtt agg gtt    2119
Cys Phe Lys Arg Tyr Gly Asn Ser Thr Arg Ser Tyr Ala Val Arg Val
            660                 665                 670 gga gat tat cat act ctg gta cca gag gag ttt gag gaa gaa att gga    2167
Gly Asp Tyr His Thr Leu Val Pro Glu Glu Phe Glu Glu Glu Ile Gly
            675                 680                 685 gtt caa cag att gtg att cat cgg gag tat cga ccc gac cgc agt gat    2215
Val Gln Gln Ile Val Ile His Arg Glu Tyr Arg Pro Asp Arg Ser Asp
690                 695                 700 tat gac ata gcc ctg gtt aga tta caa gga cca gaa gag caa tgt gcc    2263
Tyr Asp Ile Ala Leu Val Arg Leu Gln Gly Pro Glu Glu Gln Cys Ala
705                 710                 715                 720 aga ttc agc agc cat gtt ttg cca gcc tgt tta cca ctc tgg aga gag    2311
Arg Phe Ser Ser His Val Leu Pro Ala Cys Leu Pro Leu Trp Arg Glu
                725                 730                 735 agg cca cag aaa aca gca tcc aac tgt tac ata aca gga tgg ggt gac    2359
Arg Pro Gln Lys Thr Ala Ser Asn Cys Tyr Ile Thr Gly Trp Gly Asp
            740                 745                 750 aca gga cga gcc tat tca aga aca cta caa caa gca gcc att ccc tta    2407
Thr Gly Arg Ala Tyr Ser Arg Thr Leu Gln Gln Ala Ala Ile Pro Leu
            755                 760                 765 ctt cct aaa agg ttt tgt gaa gaa cgt tat aag ggt cgg ttt aca ggg    2455
Leu Pro Lys Arg Phe Cys Glu Glu Arg Tyr Lys Gly Arg Phe Thr Gly
770                 775                 780 aga atg ctt tgt gct gga aac ctc cat gaa cac aaa cgc gtg gac agc    2503
Arg Met Leu Cys Ala Gly Asn Leu His Glu His Lys Arg Val Asp Ser
785                 790                 795                 800 tgc cag gga gac agc gga gga cca ctc atg tgt gaa cgg ccc gga gag    2551
Cys Gln Gly Asp Ser Gly Gly Pro Leu Met Cys Glu Arg Pro Gly Glu
                805                 810                 815 agc tgg gtg gtg tat ggg gtg acc tcc tgg ggg tat ggc tgt gga gtc    2599
Ser Trp Val Val Tyr Gly Val Thr Ser Trp Gly Tyr Gly Cys Gly Val
            820                 825                 830 aag gat tct cct ggt gtt tat acc aaa gtc tca gcc ttt gta cct tgg    2647
Lys Asp Ser Pro Gly Val Tyr Thr Lys Val Ser Ala Phe Val Pro Trp
            835                 840                 845 ata aaa agt gtc acc aaa ctg taattcttca tggaaacttc aaagcagcat       2698
Ile Lys Ser Val Thr Lys Leu
            850                 855 ttaaacaaat ggaaaacttt gaaccccac tattagcact cagcagagat gacaacaaat   2758
ggcaagatct gttttgctt tgtgttgtgg taaaaattg tgtaccccct gctgcttttg    2818
agaaatttgt gaacattttc agaggcctca gtgtagtgga agtgataatc cttaaatgaa  2878
cattttctac cctaatttca ctggagtgac ttattctaag cctcatctat ccctaccta   2938 tttctcaaaa tcattctatg ctgattttac aaaagatcat ttttacattt gaactgagaa  2998 cccctttttaa ttgaatcagt ggtgtctgaa atcatattaa ataccacat ttgacataaa  3058
```

-continued

```
tgcggtaccc tttactacac tcatgagtgg catatttatg cttaggtctt ttcaaaagac   3118
ttgacaagaa atcttcatat tctctgtagc ctttgtcaag tgaggaaatc agtggttaaa   3178
gaattccact ataaactttt aggcctgaat aggagtagta aagcctcaag gacatctgcc   3238
tgtcacaata tattctcaaa gtgatctgat atttggaaac aagtatcctt gttgagtacc   3298
aagtgctaca gaaaccataa gataaaaata ctttctacct acagcgtgcc cg           3350
```

<210> SEQ ID NO 2
<211> LENGTH: 875
<212> TYPE: PRT
<213> ORGANISM: Homo sapiens

<400> SEQUENCE: 2

```
Met Thr Leu Ala Arg Phe Val Leu Ala Leu Met Leu Gly Ala Leu Pro
-20             -15                 -10                  -5

Glu Val Val Gly Phe Asp Ser Val Leu Asn Asp Ser Leu His His Ser
             -1   1               5                  10

His Arg His Ser Pro Pro Ala Gly Pro His Tyr Pro Tyr Tyr Leu Pro
             15                  20                  25

Thr Gln Gln Arg Pro Pro Thr Thr Arg Pro Pro Pro Leu Pro Arg
         30                  35                  40

Phe Pro Arg Pro Pro Arg Ala Leu Pro Ala Gln Arg Pro His Ala Leu
 45                  50                  55                  60

Gln Ala Gly His Thr Pro Arg Pro His Pro Trp Gly Cys Pro Ala Gly
                 65                  70                  75

Glu Pro Trp Val Ser Val Thr Asp Phe Gly Ala Pro Cys Leu Arg Trp
                 80                  85                  90

Ala Glu Val Pro Pro Phe Leu Glu Arg Ser Pro Ala Ser Trp Ala
                 95                 100                 105

Gln Leu Arg Gly Gln Arg His Asn Phe Cys Arg Ser Pro Asp Gly Ala
        110                 115                 120

Gly Arg Pro Trp Cys Phe Tyr Gly Asp Ala Arg Gly Lys Val Asp Trp
125                 130                 135                 140

Gly Tyr Cys Asp Cys Arg His Gly Ser Val Arg Leu Arg Gly Gly Lys
                145                 150                 155

Asn Glu Phe Glu Gly Thr Val Glu Val Tyr Ala Ser Gly Val Trp Gly
                160                 165                 170

Thr Val Cys Ser Ser His Trp Asp Asp Ser Asp Ala Ser Val Ile Cys
        175                 180                 185

His Gln Leu Gln Leu Gly Gly Lys Gly Ile Ala Lys Gln Thr Pro Phe
    190                 195                 200

Ser Gly Leu Gly Leu Ile Pro Ile Tyr Trp Ser Asn Val Arg Cys Arg
205                 210                 215                 220

Gly Asp Glu Glu Asn Ile Leu Leu Cys Glu Lys Asp Ile Trp Gln Gly
                225                 230                 235

Gly Val Cys Pro Gln Lys Met Ala Ala Ala Val Thr Cys Ser Phe Ser
        240                 245                 250

His Gly Pro Thr Phe Pro Ile Ile Arg Leu Ala Gly Gly Ser Ser Val
    255                 260                 265

His Glu Gly Arg Val Glu Leu Tyr His Ala Gly Gln Trp Gly Thr Val
    270                 275                 280

Cys Asp Asp Gln Trp Asp Asp Ala Asp Ala Glu Val Ile Cys Arg Gln
285                 290                 295                 300
```

```
Leu Gly Leu Ser Gly Ile Ala Lys Ala Trp His Gln Ala Tyr Phe Gly
                305                 310                 315

Glu Gly Ser Gly Pro Val Met Leu Asp Glu Val Arg Cys Thr Gly Asn
            320                 325                 330

Glu Leu Ser Ile Glu Gln Cys Pro Lys Ser Ser Trp Gly His Asn
        335                 340                 345

Cys Gly His Lys Glu Asp Ala Gly Val Ser Cys Thr Pro Leu Thr Asp
    350                 355                 360

Gly Val Ile Arg Leu Ala Gly Lys Gly Ser His Glu Gly Arg Leu
365                 370                 375                 380

Glu Val Tyr Tyr Arg Gly Gln Trp Gly Thr Val Cys Asp Asp Gly Trp
                385                 390                 395

Thr Glu Leu Asn Thr Tyr Val Val Cys Arg Gln Leu Gly Phe Lys Tyr
            400                 405                 410

Gly Lys Gln Ala Ser Ala Asn His Phe Glu Glu Ser Thr Gly Pro Ile
                415                 420                 425

Trp Leu Asp Asp Val Ser Cys Ser Gly Lys Glu Thr Arg Phe Leu Gln
            430                 435                 440

Cys Ser Arg Arg Gln Trp Gly Arg His Asp Cys Ser His Arg Glu Asp
445                 450                 455                 460

Val Ser Ile Ala Cys Tyr Pro Gly Gly Glu Gly His Arg Leu Ser Leu
                465                 470                 475

Gly Phe Pro Val Arg Leu Met Asp Gly Glu Asn Lys Lys Glu Gly Arg
            480                 485                 490

Val Glu Val Phe Ile Asn Gly Gln Trp Gly Thr Ile Cys Asp Asp Gly
                495                 500                 505

Trp Thr Asp Lys Asp Ala Ala Val Ile Cys Arg Gln Leu Gly Tyr Lys
        510                 515                 520

Gly Pro Ala Arg Ala Arg Thr Met Ala Tyr Phe Gly Glu Gly Lys Gly
525                 530                 535                 540

Pro Ile His Val Asp Asn Val Lys Cys Thr Gly Asn Glu Arg Ser Leu
            545                 550                 555

Ala Asp Cys Ile Lys Gln Asp Ile Gly Arg His Asn Cys Arg His Ser
            560                 565                 570

Glu Asp Ala Gly Val Ile Cys Asp Tyr Phe Gly Lys Lys Ala Ser Gly
        575                 580                 585

Asn Ser Asn Lys Glu Ser Leu Ser Ser Val Cys Gly Leu Arg Leu Leu
        590                 595                 600

His Arg Arg Gln Lys Arg Ile Ile Gly Gly Lys Asn Ser Leu Arg Gly
605                 610                 615                 620

Gly Trp Pro Trp Gln Val Ser Leu Arg Leu Lys Ser Ser His Gly Asp
                625                 630                 635

Gly Arg Leu Leu Cys Gly Ala Thr Leu Leu Ser Ser Cys Trp Val Leu
            640                 645                 650

Thr Ala Ala His Cys Phe Lys Arg Tyr Gly Asn Ser Thr Arg Ser Tyr
            655                 660                 665

Ala Val Arg Val Gly Asp Tyr His Thr Leu Val Pro Glu Glu Phe Glu
        670                 675                 680

Glu Glu Ile Gly Val Gln Gln Ile Val Ile His Arg Glu Tyr Arg Pro
685                 690                 695                 700

Asp Arg Ser Asp Tyr Asp Ile Ala Leu Val Arg Leu Gln Gly Pro Glu
                705                 710                 715
```

```
Glu Gln Cys Ala Arg Phe Ser Ser His Val Leu Pro Ala Cys Leu Pro
            720                 725                 730

Leu Trp Arg Glu Arg Pro Gln Lys Thr Ala Ser Asn Cys Tyr Ile Thr
            735                 740                 745

Gly Trp Gly Asp Thr Gly Arg Ala Tyr Ser Arg Thr Leu Gln Gln Ala
            750                 755                 760

Ala Ile Pro Leu Leu Pro Lys Arg Phe Cys Glu Glu Arg Tyr Lys Gly
765                 770                 775                 780

Arg Phe Thr Gly Arg Met Leu Cys Ala Gly Asn Leu His Glu His Lys
            785                 790                 795

Arg Val Asp Ser Cys Gln Gly Asp Ser Gly Gly Pro Leu Met Cys Glu
            800                 805                 810

Arg Pro Gly Glu Ser Trp Val Val Tyr Gly Val Thr Ser Trp Gly Tyr
            815                 820                 825

Gly Cys Gly Val Lys Asp Ser Pro Gly Val Tyr Thr Lys Val Ser Ala
            830                 835                 840

Phe Val Pro Trp Ile Lys Ser Val Thr Lys Leu
845                 850                 855

<210> SEQ ID NO 3
<211> LENGTH: 2356
<212> TYPE: DNA
<213> ORGANISM: Mus musculus
<220> FEATURE:
<221> NAME/KEY: sig_peptide
<222> LOCATION: (24)..(86)
<220> FEATURE:
<221> NAME/KEY: mat_peptide
<222> LOCATION: (87)..(2306)
<220> FEATURE:
<221> NAME/KEY: CDS
<222> LOCATION: (24)..(2306)
<220> FEATURE:
<221> NAME/KEY: polyA_site
<222> LOCATION: one-of(2341, 2356)
<220> FEATURE:
<221> NAME/KEY: 5'UTR
<222> LOCATION: (1)..(23)
<220> FEATURE:
<221> NAME/KEY: 3'UTR
<222> LOCATION: (2307)..one-of(2341, 2356)

<400> SEQUENCE: 3
ggaccacact cggcgccgca gcc atg gcg ctc gcc cgc tgc gtg ctg gct gtg      53
                         Met Ala Leu Ala Arg Cys Val Leu Ala Val
                                 -20                 -15 att tta ggg gca ctg tct gta gtg gcc cgc gct gat ccg gtc tcg cgc      101
Ile Leu Gly Ala Leu Ser Val Val Ala Arg Ala Asp Pro Val Ser Arg
   -10                  -5                  -1  1                 5 tct ccc ctt cac cgc ccg cat ccg tcc cca ccg cgt tcc caa cac gcg      149
Ser Pro Leu His Arg Pro His Pro Ser Pro Pro Arg Ser Gln His Ala
                10                  15                  20 cac tac ctt ccc agc tcg cgg cgg cca ccc agg acc ccg cgc ttc ccg      197
His Tyr Leu Pro Ser Ser Arg Arg Pro Pro Arg Thr Pro Arg Phe Pro
            25                  30                  35 ctc ccg ctg cgg atc ccc gct gcc cag cgc ccg cag gtc ctc agc acc      245
Leu Pro Leu Arg Ile Pro Ala Ala Gln Arg Pro Gln Val Leu Ser Thr
        40                  45                  50 ggg cac acg ccc ccg acg att cca cgc cgc tgc ggg gca gga gag tcg      293
Gly His Thr Pro Pro Thr Ile Pro Arg Arg Cys Gly Ala Gly Glu Ser
    55                  60                  65
```

```
tgg ggc aat gcc acc aac ctc ggc gtc ccg tgt cta cac tgg gac gag       341
Trp Gly Asn Ala Thr Asn Leu Gly Val Pro Cys Leu His Trp Asp Glu
 70                  75                  80                  85 gtg ccg ccc ttc ctg gag cgg tcg ccc ccg gcc agt tgg gct gag ctg       389
Val Pro Pro Phe Leu Glu Arg Ser Pro Pro Ala Ser Trp Ala Glu Leu
                 90                  95                 100 cga ggg cag ccg cac aac ttc tgc cgg agc ccg gat ggc tcg ggc aga       437
Arg Gly Gln Pro His Asn Phe Cys Arg Ser Pro Asp Gly Ser Gly Arg
            105                 110                 115 cct tgg tgc ttc tat cgg aat gcc cag ggc aaa gta gac tgg ggc tac       485
Pro Trp Cys Phe Tyr Arg Asn Ala Gln Gly Lys Val Asp Trp Gly Tyr
        120                 125                 130 tgc gat tgt ggt caa ggc ccg gcg ttg ccc gtc att cgc ctt gtt ggt       533
Cys Asp Cys Gly Gln Gly Pro Ala Leu Pro Val Ile Arg Leu Val Gly
    135                 140                 145 ggg aac agt ggg cat gaa ggt cga gtg gag ctg tac cac gct ggc cag       581
Gly Asn Ser Gly His Glu Gly Arg Val Glu Leu Tyr His Ala Gly Gln
150                 155                 160                 165 tgg ggg acc atc tgt gac gac caa tgg gac aat gca gac gca gac gtc       629
Trp Gly Thr Ile Cys Asp Asp Gln Trp Asp Asn Ala Asp Ala Asp Val
                170                 175                 180 atc tgt agg cag ctg ggg ctc agt ggc att gcc aaa gca tgg cat cag       677
Ile Cys Arg Gln Leu Gly Leu Ser Gly Ile Ala Lys Ala Trp His Gln
            185                 190                 195 gca cat ttt ggg gaa gga tct ggc cca ata ttg ttg gat gaa gta cgc       725
Ala His Phe Gly Glu Gly Ser Gly Pro Ile Leu Leu Asp Glu Val Arg
        200                 205                 210 tgc acc gga aac gag ctg tca att gag caa tgt cca aag agt tcc tgg       773
Cys Thr Gly Asn Glu Leu Ser Ile Glu Gln Cys Pro Lys Ser Ser Trp
    215                 220                 225 ggc gaa cat aac tgt ggc cat aaa gaa gat gct gga gtg tct tgt gtt       821
Gly Glu His Asn Cys Gly His Lys Glu Asp Ala Gly Val Ser Cys Val
230                 235                 240                 245 cct cta aca gat ggt gtc atc aga ctg gca gga gga aaa agt acc cat       869
Pro Leu Thr Asp Gly Val Ile Arg Leu Ala Gly Gly Lys Ser Thr His
                250                 255                 260 gaa ggt cgc ctg gag gtc tac tac aag ggg cag tgg ggg aca gtc tgt       917
Glu Gly Arg Leu Glu Val Tyr Tyr Lys Gly Gln Trp Gly Thr Val Cys
            265                 270                 275 gat gat ggc tgg act gag atg aac aca tac gtg gct tgt cga ctg ctg       965
Asp Asp Gly Trp Thr Glu Met Asn Thr Tyr Val Ala Cys Arg Leu Leu
        280                 285                 290 gga ttt aaa tac ggc aaa cag tcc tct gtg aac cat ttt gat ggc agc      1013
Gly Phe Lys Tyr Gly Lys Gln Ser Ser Val Asn His Phe Asp Gly Ser
    295                 300                 305 aac agg ccc ata tgg ctg gat gac gtc agc tgc tca gga aaa gaa gtc      1061
Asn Arg Pro Ile Trp Leu Asp Asp Val Ser Cys Ser Gly Lys Glu Val
310                 315                 320                 325 agc ttc att cag tgt tcc agg aga cag tgg gga agg cat gac tgc agc      1109
Ser Phe Ile Gln Cys Ser Arg Arg Gln Trp Gly Arg His Asp Cys Ser
                330                 335                 340 cat aga gaa gat gtg ggc ctc acc tgc tat cct gac agc gat gga cat      1157
His Arg Glu Asp Val Gly Leu Thr Cys Tyr Pro Asp Ser Asp Gly His
            345                 350                 355 agg ctt tct cca ggt ttt ccc atc aga cta gtg gat gga gag aat aag      1205
Arg Leu Ser Pro Gly Phe Pro Ile Arg Leu Val Asp Gly Glu Asn Lys
        360                 365                 370 aag gaa gga cga gtg gag gtt ttt gtc aat ggc caa tgg gga aca atc      1253
Lys Glu Gly Arg Val Glu Val Phe Val Asn Gly Gln Trp Gly Thr Ile
    375                 380                 385
```

```
                                                               -continued
tgc gat gac gga tgg acc gat aag cat gca gct gtg atc tgc cgg caa    1301
Cys Asp Asp Gly Trp Thr Asp Lys His Ala Ala Val Ile Cys Arg Gln
390                 395                 400                 405 ctt ggc tat aag ggt cct gcc aga gca agg act atg gct tat ttt ggg    1349
Leu Gly Tyr Lys Gly Pro Ala Arg Ala Arg Thr Met Ala Tyr Phe Gly
                410                 415                 420 gaa gga aaa ggc ccc atc cac atg gat aat gtg aag tgc aca gga aat    1397
Glu Gly Lys Gly Pro Ile His Met Asp Asn Val Lys Cys Thr Gly Asn
            425                 430                 435 gag aag gcc ctg gct gac tgt gtc aaa caa gac att gga agg cac aac    1445
Glu Lys Ala Leu Ala Asp Cys Val Lys Gln Asp Ile Gly Arg His Asn
        440                 445                 450 tgc cgc cac agt gag gat gca gga gtc atc tgt gac tat tta gag aag    1493
Cys Arg His Ser Glu Asp Ala Gly Val Ile Cys Asp Tyr Leu Glu Lys
    455                 460                 465 aaa gca tca agt agt ggt aat aaa gag atg ctc tca tct gga tgt gga    1541
Lys Ala Ser Ser Ser Gly Asn Lys Glu Met Leu Ser Ser Gly Cys Gly
470                 475                 480                 485 ctg agg tta ctg cac cgt cgg cag aaa cgg atc att ggt ggg aac aat    1589
Leu Arg Leu Leu His Arg Arg Gln Lys Arg Ile Ile Gly Gly Asn Asn
                490                 495                 500 tct tta agg ggt gcc tgg cct tgg cag gct tcc ctc agg ctg agg tcg    1637
Ser Leu Arg Gly Ala Trp Pro Trp Gln Ala Ser Leu Arg Leu Arg Ser
            505                 510                 515 gcc cat gga gac ggc agg ctg ctt tgt gga gct acc ctt ctg agt agc    1685
Ala His Gly Asp Gly Arg Leu Leu Cys Gly Ala Thr Leu Leu Ser Ser
        520                 525                 530 tgc tgg gtc ctg aca gct gca cac tgc ttc aaa agg tac gga aac aac    1733
Cys Trp Val Leu Thr Ala Ala His Cys Phe Lys Arg Tyr Gly Asn Asn
    535                 540                 545 tcg agg agc tat gca gtt cga gtt ggg gat tat cat act ctg gtc cca    1781
Ser Arg Ser Tyr Ala Val Arg Val Gly Asp Tyr His Thr Leu Val Pro
550                 555                 560                 565 gag gag ttt gaa caa gaa ata ggg gtt caa cag att gtg att cac agg    1829
Glu Glu Phe Glu Gln Glu Ile Gly Val Gln Gln Ile Val Ile His Arg
                570                 575                 580 aac tac agg cca gac aga agc gac tat gac att gcc ctg gtt aga ttg    1877
Asn Tyr Arg Pro Asp Arg Ser Asp Tyr Asp Ile Ala Leu Val Arg Leu
            585                 590                 595 caa gga cca ggg gag caa tgt gcc aga cta agc acc cac gtt ttg cca    1925
Gln Gly Pro Gly Glu Gln Cys Ala Arg Leu Ser Thr His Val Leu Pro
        600                 605                 610 gcc tgt tta cct cta tgg aga gag agg cca cag aaa aca gcc tcc aac    1973
Ala Cys Leu Pro Leu Trp Arg Glu Arg Pro Gln Lys Thr Ala Ser Asn
    615                 620                 625 tgt cac ata aca gga tgg gga gac aca ggt cgt gcc tac tca aga act    2021
Cys His Ile Thr Gly Trp Gly Asp Thr Gly Arg Ala Tyr Ser Arg Thr
630                 635                 640                 645 cta caa caa gct gct gtg cct ctg tta ccc aag agg ttt tgt aaa gag    2069
Leu Gln Gln Ala Ala Val Pro Leu Leu Pro Lys Arg Phe Cys Lys Glu
                650                 655                 660 agg tac aag gga cta ttt act ggg aga atg ctc tgt gct ggg aac ctc    2117
Arg Tyr Lys Gly Leu Phe Thr Gly Arg Met Leu Cys Ala Gly Asn Leu
            665                 670                 675 caa gaa gac aac cgt gtg gac agc tgc cag gga gac agt gga gga cca    2165
Gln Glu Asp Asn Arg Val Asp Ser Cys Gln Gly Asp Ser Gly Gly Pro
        680                 685                 690 ctc atg tgt gaa aag cct gat gag tcc tgg gtt gtg tat ggg gtg act    2213
Leu Met Cys Glu Lys Pro Asp Glu Ser Trp Val Val Tyr Gly Val Thr
    695                 700                 705
```

```
tcc tgg ggg tat gga tgt gga gtc aaa gac act cct gga gtt tat acc      2261
Ser Trp Gly Tyr Gly Cys Gly Val Lys Asp Thr Pro Gly Val Tyr Thr
710             715                 720                 725 aga gtc ccc gct ttt gta cct tgg ata aaa agt gtc acc agt ctg          2306
Arg Val Pro Ala Phe Val Pro Trp Ile Lys Ser Val Thr Ser Leu
            730                 735                 740 taacttatgg aaagctcaag aaatagtaaa acagtaacta ttcagtcttc                2356

<210> SEQ ID NO 4
<211> LENGTH: 761
<212> TYPE: PRT
<213> ORGANISM: Mus musculus

<400> SEQUENCE: 4

Met Ala Leu Ala Arg Cys Val Leu Ala Val Ile Leu Gly Ala Leu Ser
    -20                 -15                 -10

Val Val Ala Arg Ala Asp Pro Val Ser Arg Ser Pro Leu His Arg Pro
 -5              -1   1               5                  10

His Pro Ser Pro Pro Arg Ser Gln His Ala His Tyr Leu Pro Ser Ser
                15                  20                  25

Arg Arg Pro Pro Arg Thr Pro Arg Phe Pro Leu Pro Leu Arg Ile Pro
            30                  35                  40

Ala Ala Gln Arg Pro Gln Val Leu Ser Thr Gly His Thr Pro Pro Thr
        45                  50                  55

Ile Pro Arg Arg Cys Gly Ala Gly Glu Ser Trp Gly Asn Ala Thr Asn
 60                 65                  70                  75

Leu Gly Val Pro Cys Leu His Trp Asp Glu Val Pro Pro Phe Leu Glu
                80                  85                  90

Arg Ser Pro Pro Ala Ser Trp Ala Glu Leu Arg Gly Gln Pro His Asn
            95                  100                 105

Phe Cys Arg Ser Pro Asp Gly Ser Gly Arg Pro Trp Cys Phe Tyr Arg
        110                 115                 120

Asn Ala Gln Gly Lys Val Asp Trp Gly Tyr Cys Asp Cys Gly Gln Gly
125                 130                 135

Pro Ala Leu Pro Val Ile Arg Leu Val Gly Gly Asn Ser Gly His Glu
140                 145                 150                 155

Gly Arg Val Glu Leu Tyr His Ala Gly Gln Trp Gly Thr Ile Cys Asp
                160                 165                 170

Asp Gln Trp Asp Asn Ala Asp Ala Asp Val Ile Cys Arg Gln Leu Gly
            175                 180                 185

Leu Ser Gly Ile Ala Lys Ala Trp His Gln Ala His Phe Gly Glu Gly
        190                 195                 200

Ser Gly Pro Ile Leu Leu Asp Glu Val Arg Cys Thr Gly Asn Glu Leu
205                 210                 215

Ser Ile Glu Gln Cys Pro Lys Ser Ser Trp Gly Glu His Asn Cys Gly
220                 225                 230                 235

His Lys Glu Asp Ala Gly Val Ser Cys Val Pro Leu Thr Asp Gly Val
                240                 245                 250

Ile Arg Leu Ala Gly Gly Lys Ser Thr His Glu Gly Arg Leu Glu Val
            255                 260                 265

Tyr Tyr Lys Gly Gln Trp Gly Thr Val Cys Asp Asp Gly Trp Thr Glu
        270                 275                 280

Met Asn Thr Tyr Val Ala Cys Arg Leu Leu Gly Phe Lys Tyr Gly Lys
285                 290                 295
```

-continued

```
Gln Ser Ser Val Asn His Phe Asp Gly Ser Asn Arg Pro Ile Trp Leu
300                 305                 310                 315

Asp Asp Val Ser Cys Ser Gly Lys Glu Val Ser Phe Ile Gln Cys Ser
            320                 325                 330

Arg Arg Gln Trp Gly Arg His Asp Cys Ser His Arg Glu Asp Val Gly
        335                 340                 345

Leu Thr Cys Tyr Pro Asp Ser Asp Gly His Arg Leu Ser Pro Gly Phe
    350                 355                 360

Pro Ile Arg Leu Val Asp Gly Glu Asn Lys Lys Gly Arg Val Glu
        365                 370                 375

Val Phe Val Asn Gly Gln Trp Gly Thr Ile Cys Asp Asp Gly Trp Thr
380                 385                 390                 395

Asp Lys His Ala Ala Val Ile Cys Arg Gln Leu Gly Tyr Lys Gly Pro
                400                 405                 410

Ala Arg Ala Arg Thr Met Ala Tyr Phe Gly Glu Gly Lys Gly Pro Ile
            415                 420                 425

His Met Asp Asn Val Lys Cys Thr Gly Asn Glu Lys Ala Leu Ala Asp
        430                 435                 440

Cys Val Lys Gln Asp Ile Gly Arg His Asn Cys Arg His Ser Glu Asp
    445                 450                 455

Ala Gly Val Ile Cys Asp Tyr Leu Glu Lys Lys Ala Ser Ser Gly
460                 465                 470                 475

Asn Lys Glu Met Leu Ser Ser Gly Cys Gly Leu Arg Leu Leu His Arg
                480                 485                 490

Arg Gln Lys Arg Ile Ile Gly Gly Asn Asn Ser Leu Arg Gly Ala Trp
            495                 500                 505

Pro Trp Gln Ala Ser Leu Arg Leu Arg Ser Ala His Gly Asp Gly Arg
        510                 515                 520

Leu Leu Cys Gly Ala Thr Leu Leu Ser Ser Cys Trp Val Leu Thr Ala
    525                 530                 535

Ala His Cys Phe Lys Arg Tyr Gly Asn Asn Ser Arg Ser Tyr Ala Val
540                 545                 550                 555

Arg Val Gly Asp Tyr His Thr Leu Val Pro Glu Glu Phe Glu Gln Glu
                560                 565                 570

Ile Gly Val Gln Gln Ile Val Ile His Arg Asn Tyr Arg Pro Asp Arg
            575                 580                 585

Ser Asp Tyr Asp Ile Ala Leu Val Arg Leu Gln Gly Pro Gly Glu Gln
        590                 595                 600

Cys Ala Arg Leu Ser Thr His Val Leu Pro Ala Cys Leu Pro Leu Trp
    605                 610                 615

Arg Glu Arg Pro Gln Lys Thr Ala Ser Asn Cys His Ile Thr Gly Trp
620                 625                 630                 635

Gly Asp Thr Gly Arg Ala Tyr Ser Arg Thr Leu Gln Gln Ala Ala Val
                640                 645                 650

Pro Leu Leu Pro Lys Arg Phe Cys Lys Glu Arg Tyr Lys Gly Leu Phe
            655                 660                 665

Thr Gly Arg Met Leu Cys Ala Gly Asn Leu Gln Glu Asp Asn Arg Val
        670                 675                 680

Asp Ser Cys Gln Gly Asp Ser Gly Gly Pro Leu Met Cys Glu Lys Pro
    685                 690                 695

Asp Glu Ser Trp Val Val Tyr Gly Val Thr Ser Trp Gly Tyr Gly Cys
700                 705                 710                 715
```

```
Gly Val Lys Asp Thr Pro Gly Val Tyr Thr Arg Val Pro Ala Phe Val
                720                 725                 730

Pro Trp Ile Lys Ser Val Thr Ser Leu
                735                 740

<210> SEQ ID NO 5
<211> LENGTH: 257
<212> TYPE: PRT
<213> ORGANISM: Homo sapiens

<400> SEQUENCE: 5

Cys Gly Leu Arg Leu His Arg Arg Gln Lys Arg Ile Ile Gly Gly
  1               5                  10                  15

Lys Asn Ser Leu Arg Gly Gly Trp Pro Trp Gln Val Ser Leu Arg Leu
                 20                  25                  30

Lys Ser Ser His Gly Asp Gly Arg Leu Leu Cys Gly Ala Thr Leu Leu
             35                  40                  45

Ser Ser Cys Trp Val Leu Thr Ala Ala His Cys Phe Lys Arg Tyr Gly
         50                  55                  60

Asn Ser Thr Arg Ser Tyr Ala Val Arg Val Gly Asp Tyr His Thr Leu
 65                  70                  75                  80

Val Pro Glu Glu Phe Glu Glu Ile Gly Val Gln Gln Ile Val Ile
                 85                  90                  95

His Arg Glu Tyr Arg Pro Asp Arg Ser Asp Tyr Asp Ile Ala Leu Val
                100                 105                 110

Arg Leu Gln Gly Pro Glu Glu Gln Cys Ala Arg Phe Ser Ser His Val
            115                 120                 125

Leu Pro Ala Cys Leu Pro Leu Trp Arg Glu Arg Pro Gln Lys Thr Ala
130                 135                 140

Ser Asn Cys Tyr Ile Thr Gly Trp Gly Asp Thr Gly Arg Ala Tyr Ser
145                 150                 155                 160

Arg Thr Leu Gln Gln Ala Ala Ile Pro Leu Leu Pro Lys Arg Phe Cys
                165                 170                 175

Glu Glu Arg Tyr Lys Gly Arg Phe Thr Gly Arg Met Leu Cys Ala Gly
            180                 185                 190

Asn Leu His Glu His Lys Arg Val Asp Ser Cys Gln Gly Asp Ser Gly
        195                 200                 205

Gly Pro Leu Met Cys Glu Arg Pro Gly Glu Ser Trp Val Val Tyr Gly
    210                 215                 220

Val Thr Ser Trp Gly Tyr Gly Cys Gly Val Lys Asp Ser Pro Gly Val
225                 230                 235                 240

Tyr Thr Lys Val Ser Ala Phe Val Pro Trp Ile Lys Ser Val Thr Lys
                245                 250                 255

Leu

<210> SEQ ID NO 6
<211> LENGTH: 257
<212> TYPE: PRT
<213> ORGANISM: Mus musculus

<400> SEQUENCE: 6

Cys Gly Leu Arg Leu His Arg Arg Gln Lys Arg Ile Ile Gly Gly
  1               5                  10                  15

Asn Asn Ser Leu Arg Gly Ala Trp Pro Trp Gln Ala Ser Leu Arg Leu
                 20                  25                  30
```

-continued

```
Arg Ser Ala His Gly Asp Gly Arg Leu Leu Cys Gly Ala Thr Leu Leu
         35                  40                  45

Ser Ser Cys Trp Val Leu Thr Ala Ala His Cys Phe Lys Arg Tyr Gly
 50                  55                  60

Asn Asn Ser Arg Ser Tyr Ala Val Arg Val Gly Asp Tyr His Thr Leu
 65                  70                  75                  80

Val Pro Glu Glu Phe Glu Gln Glu Ile Gly Val Gln Ile Val Ile
                 85                  90                  95

His Arg Asn Tyr Arg Pro Asp Arg Ser Asp Tyr Asp Ile Ala Leu Val
                100                 105                 110

Arg Leu Gln Gly Pro Gly Glu Gln Cys Ala Arg Leu Ser Thr His Val
                115                 120                 125

Leu Pro Ala Cys Leu Pro Leu Trp Arg Glu Arg Pro Gln Lys Thr Ala
        130                 135                 140

Ser Asn Cys His Ile Thr Gly Trp Gly Asp Thr Gly Arg Ala Tyr Ser
145                 150                 155                 160

Arg Thr Leu Gln Gln Ala Ala Val Pro Leu Leu Pro Lys Arg Phe Cys
                165                 170                 175

Lys Glu Arg Tyr Lys Gly Leu Phe Thr Gly Arg Met Leu Cys Ala Gly
                180                 185                 190

Asn Leu Gln Glu Asp Asn Arg Val Asp Ser Cys Gln Gly Asp Ser Gly
            195                 200                 205

Gly Pro Leu Met Cys Glu Lys Pro Asp Glu Ser Trp Val Val Tyr Gly
        210                 215                 220

Val Thr Ser Trp Gly Tyr Gly Cys Gly Val Lys Asp Thr Pro Gly Val
225                 230                 235                 240

Tyr Thr Arg Val Pro Ala Phe Val Pro Trp Ile Lys Ser Val Thr Ser
                245                 250                 255

Leu

<210> SEQ ID NO 7
<211> LENGTH: 23
<212> TYPE: DNA
<213> ORGANISM: Mus musculus
<220> FEATURE:
<221> NAME/KEY: misc_feature
<222> LOCATION: (6)..(18)
<223> OTHER INFORMATION: Nucleotides 6, 9, 12, 15, and 18 are n wherein
      n = i.

<400> SEQUENCE: 7
tgggtnsynw sngcngcnca ttg                                              23

<210> SEQ ID NO 8
<211> LENGTH: 20
<212> TYPE: DNA
<213> ORGANISM: Mus musculus
<220> FEATURE:
<221> NAME/KEY: misc_feature
<222> LOCATION: (9)..(18)
<223> OTHER INFORMATION: Nucleotides 9, 15, and 18 are n wherein n = i.

<400> SEQUENCE: 8
acrbtyccnc trwsnccncc                                                  20

<210> SEQ ID NO 9
<211> LENGTH: 14
<212> TYPE: PRT
<213> ORGANISM: Mus musculus
```

```
<400> SEQUENCE: 9

Ser Ser Cys Trp Val Leu Ser Ala Ala His Cys Phe Leu Glu
 1               5                  10

<210> SEQ ID NO 10
<211> LENGTH: 13
<212> TYPE: PRT
<213> ORGANISM: Mus musculus

<400> SEQUENCE: 10

His Asp Ala Cys Gln Gly Asp Ser Gly Gly Pro Leu Val
 1               5                  10

<210> SEQ ID NO 11
<211> LENGTH: 14
<212> TYPE: PRT
<213> ORGANISM: Mus musculus

<400> SEQUENCE: 11

Ser Pro Cys Trp Val Ala Ser Ala Ala His Cys Phe Ile Gln
 1               5                  10

<210> SEQ ID NO 12
<211> LENGTH: 13
<212> TYPE: PRT
<213> ORGANISM: Mus musculus

<400> SEQUENCE: 12

Thr Asp Ser Cys Lys Gly Asp Ser Gly Gly Pro Leu Ile
 1               5                  10

<210> SEQ ID NO 13
<211> LENGTH: 14
<212> TYPE: PRT
<213> ORGANISM: Mus musculus

<400> SEQUENCE: 13

Ser Asp Arg Trp Val Leu Thr Ala Ala His Cys Ile Leu Tyr
 1               5                  10

<210> SEQ ID NO 14
<211> LENGTH: 13
<212> TYPE: PRT
<213> ORGANISM: Mus musculus

<400> SEQUENCE: 14

Gly Asp Ala Cys Glu Gly Asp Ser Gly Gly Pro Phe Val
 1               5                  10

<210> SEQ ID NO 15
<211> LENGTH: 14
<212> TYPE: PRT
<213> ORGANISM: Mus musculus

<400> SEQUENCE: 15

Ala Pro Glu Trp Val Leu Thr Ala Ala His Cys Leu Lys Ser
 1               5                  10

<210> SEQ ID NO 16
<211> LENGTH: 13
<212> TYPE: PRT
<213> ORGANISM: Mus musculus
```

-continued

```
<400> SEQUENCE: 16

Val Asp Ser Cys Gln Gly Asp Ser Gly Gly Pro Leu Val
1               5                   10

<210> SEQ ID NO 17
<211> LENGTH: 14
<212> TYPE: PRT
<213> ORGANISM: Mus musculus

<400> SEQUENCE: 17

Asn Asp Gln Trp Val Val Ser Ala Ala His Cys Tyr Lys Tyr
1               5                   10

<210> SEQ ID NO 18
<211> LENGTH: 13
<212> TYPE: PRT
<213> ORGANISM: Mus musculus

<400> SEQUENCE: 18

Lys Asp Ser Cys Gln Gly Asp Ser Gly Gly Pro Val Val
1               5                   10

<210> SEQ ID NO 19
<211> LENGTH: 14
<212> TYPE: PRT
<213> ORGANISM: Mus musculus

<400> SEQUENCE: 19

Ser Glu Asp Trp Val Val Thr Ala Ala His Cys Gly Val Lys
1               5                   10

<210> SEQ ID NO 20
<211> LENGTH: 13
<212> TYPE: PRT
<213> ORGANISM: Mus musculus

<400> SEQUENCE: 20

Val Ser Ser Cys Met Gly Asp Ser Gly Gly Pro Leu Val
1               5                   10

<210> SEQ ID NO 21
<211> LENGTH: 14
<212> TYPE: PRT
<213> ORGANISM: Mus musculus

<400> SEQUENCE: 21

Ala Asn Asn Trp Val Leu Thr Ala Ala His Cys Leu Ser Asn
1               5                   10

<210> SEQ ID NO 22
<211> LENGTH: 13
<212> TYPE: PRT
<213> ORGANISM: Mus musculus

<400> SEQUENCE: 22

Thr Ser Ser Cys Asn Gly Asp Ser Gly Gly Pro Leu Asn
1               5                   10

<210> SEQ ID NO 23
<211> LENGTH: 32
<212> TYPE: DNA
<213> ORGANISM: EcoRI and BamHI
```

```
<220> FEATURE:
<221> NAME/KEY: misc_feature
<222> LOCATION: (15)..(27)
<223> OTHER INFORMATION: Nucleotides 15, 18, 21, 24, and 27 are n
      wherein n = i.
<220> FEATURE:
<221> NAME/KEY: misc_feature
<222> LOCATION: (16)
<223> OTHER INFORMATION: Nucleotide 16 is n wherein n c/g.
<220> FEATURE:
<221> NAME/KEY: misc_feature
<222> LOCATION: (17)
<223> OTHER INFORMATION: Nucleotide 17 is n wherein n = t/c.
<220> FEATURE:
<221> NAME/KEY: misc_feature
<222> LOCATION: (19)
<223> OTHER INFORMATION: Nucleotide 19 is n wherein n = t/a.
<220> FEATURE:
<221> NAME/KEY: misc_feature
<222> LOCATION: (20)
<223> OTHER INFORMATION: Nucleotide 20 is n wherein n = g/c.
<220> FEATURE:
<221> NAME/KEY: misc_feature
<222> LOCATION: (30)
<223> OTHER INFORMATION: Nucleotide 30 is n wherein n = t/c.

<400> SEQUENCE: 23
ggggaattct gggtnnnnnn ngcngcncan tg                              32

<210> SEQ ID NO 24
<211> LENGTH: 29
<212> TYPE: DNA
<213> ORGANISM: EcoRI and BamHI
<220> FEATURE:
<221> NAME/KEY: misc_feature
<222> LOCATION: (12)..(21)
<223> OTHER INFORMATION: Nucleotides 12, 15, and 21 are n wherein n = i.
<220> FEATURE:
<221> NAME/KEY: misc_feature
<222> LOCATION: (16)
<223> OTHER INFORMATION: Nucleotide 16 is n wherein n = g/c.
<220> FEATURE:
<221> NAME/KEY: misc_feature
<222> LOCATION: (17)
<223> OTHER INFORMATION: Nucleotide 17 is n wherein n = a/t.
<220> FEATURE:
<221> NAME/KEY: misc_feature
<222> LOCATION: (18)
<223> OTHER INFORMATION: Nucleotide 18 is n wherein n = a/g.
<220> FEATURE:
<221> NAME/KEY: misc_feature
<222> LOCATION: (24)
<223> OTHER INFORMATION: Nucleotide 24 is n wherein n = c/t.
<220> FEATURE:
<221> NAME/KEY: misc_feature
<222> LOCATION: (26)
<223> OTHER INFORMATION: Nucleotide 26 is n wherein = g/c/t.
<220> FEATURE:
<221> NAME/KEY: misc_feature
<222> LOCATION: (27)
<223> OTHER INFORMATION: Nucleotide 27 is n wherein n = g/a.

<400> SEQUENCE: 24
gggggatccc cnccnnnntc nccntnnca                                  29

<210> SEQ ID NO 25
<211> LENGTH: 33
<212> TYPE: DNA
<213> ORGANISM: HindIII and XhoI
<220> FEATURE:
<221> NAME/KEY: misc_feature
<222> LOCATION: (12)..(27)
<223> OTHER INFORMATION: Nucleotides 12, 21, 24, and 27 are n wherein
      n = i.
```

```
<220> FEATURE:
<221> NAME/KEY: misc_feature
<222> LOCATION: (15)
<223> OTHER INFORMATION: Nucleotide 15 is n wherein n = a/g.
<220> FEATURE:
<221> NAME/KEY: misc_feature
<222> LOCATION: (25)
<223> OTHER INFORMATION: Nucleotide 25 is n wherein n = a/g.
<220> FEATURE:
<221> NAME/KEY: misc_feature
<222> LOCATION: (30)
<223> OTHER INFORMATION: Nucleotide 30 is n wherein n = c/t.
<220> FEATURE:
<221> NAME/KEY: misc_feature
<222> LOCATION: (33)
<223> OTHER INFORMATION: Nucleotide 33 is n wherein n = c/t.

<400> SEQUENCE: 25
gggaagcttg gncantgggg nacnntntgn gan                                33

<210> SEQ ID NO 26
<211> LENGTH: 33
<212> TYPE: DNA
<213> ORGANISM: HindIII and XhoI
<220> FEATURE:
<221> NAME/KEY: misc_feature
<222> LOCATION: (15)..(28)
<223> OTHER INFORMATION: Nucleotides 15 and 28 are n wherein n = i.

<400> SEQUENCE: 26
gggctcgagc cccancctgt tatgtaaanag ttg                               33

<210> SEQ ID NO 27
<211> LENGTH: 17
<212> TYPE: PRT
<213> ORGANISM: Mus musculus

<400> SEQUENCE: 27

Ser Arg Ser Pro Leu His Arg Pro His Pro Ser Pro Pro Arg Ser Gln
  1               5                  10                  15

Xaa

<210> SEQ ID NO 28
<211> LENGTH: 13
<212> TYPE: PRT
<213> ORGANISM: Mus musculus

<400> SEQUENCE: 28

Leu Pro Ser Ser Arg Arg Pro Pro Arg Thr Pro Arg Phe
  1               5                  10
```